US012319719B2

(12) United States Patent
Muro et al.

(10) Patent No.: US 12,319,719 B2
(45) Date of Patent: Jun. 3, 2025

(54) ICAM-1 TARGETED FUSION ENZYMES

(71) Applicant: University of Maryland, College Park, College Park, MD (US)

(72) Inventors: Silvia Muro, Gaithersburg, MD (US); Jing Chen, Nanjing (CN); Melani Solomon, Laurel, MD (US); Kevin Gray, Washington, DC (US)

(73) Assignee: University of Maryland, College Park, College Park, MD (US)

( * ) Notice: Subject to any disclaimer, the term of this patent is extended or adjusted under 35 U.S.C. 154(b) by 0 days.

(21) Appl. No.: 18/416,843

(22) Filed: Jan. 18, 2024

(65) Prior Publication Data
US 2024/0327475 A1    Oct. 3, 2024

Related U.S. Application Data

(63) Continuation of application No. 17/571,415, filed on Jan. 7, 2022, now Pat. No. 11,912,745, which is a continuation of application No. 16/951,774, filed on Nov. 18, 2020, now Pat. No. 11,248,029.

(60) Provisional application No. 62/936,988, filed on Nov. 18, 2019.

(51) Int. Cl.
| | |
|---|---|
| C07K 14/47 | (2006.01) |
| C07K 14/705 | (2006.01) |
| C12N 9/16 | (2006.01) |
| C12N 9/24 | (2006.01) |
| C12N 9/40 | (2006.01) |

(52) U.S. Cl.
CPC ............... *C07K 14/47* (2013.01); *C12N 9/16* (2013.01); *C12N 9/2402* (2013.01); *C12N 9/2465* (2013.01); *C12Y 302/01022* (2013.01); *C12Y 302/01045* (2013.01); *C07K 2319/055* (2013.01); *C07K 2319/21* (2013.01); *C07K 2319/33* (2013.01); *C07K 2319/50* (2013.01)

(58) Field of Classification Search
None
See application file for complete search history.

(56) References Cited

U.S. PATENT DOCUMENTS

| | | | |
|---|---|---|---|
| 8,889,127 B2 | 11/2014 | Muro Galindo et al. | |
| 8,926,946 B2 | 1/2015 | Muro Galindo et al. | |

OTHER PUBLICATIONS

Muro, S., et al., Lysosomal enzyme delivery by ICAM-1-targeted nanocarriers bypassing glycosylation- and clathrin-dependent endocytosis, Molecular Therapy, Jan. 2006, vol. 13, No. 1, pp. 135-141.
Garnacho, C., et al., Delivery of acid sphingomyelinase in normal and Niemann-Pick disease mice using ICAM-1-targeted polymer nanocarriers, JPET, Feb. 20, 2008, vol. 325, No. 2, pp. 400-408.
Hsu, J., et al., Enhanced endothelial delivery and biochemical effects of a-galactosidase by ICAM-1-targeted nanocarriers for Fabry disease, Journal of Controlled Release, Feb. 10, 2011, vol. 149, No. 3, pp. 323-331.
Muro S., et al., Design of ICAM-1-targeting strategies for brain delivery of lysosomal therapies, Molecular Genetics and Metabolism, Molecular genetics and metabolism, Feb. 2011, vol. 102, No. 2, p. S31.
Hsu, J., et al., Enhanced delivery of α-glucosidase for Pompe disease by ICAM-1-targeted nanocarriers: comparative performance of a strategy for three distinct lysosomal storage disorders, Nanomedicine: Nanotechnology, Biology and Medicine, Jul. 2012, vol. 8, No. 5, pp. 731-739.
Garnacho, C., et al., A Fibrinogen-Derived Peptide Provides Intercellular Adhesion Molecule-1-Specific Targeting and Intraendothelial Transport of Polymer Nanocarriers in Human Cell Cultures and Mice, JPET, Mar. 2012, vol. 340, No. 3, pp. 638-647.
Papademetriou, J., et al., Comparative binding, endocytosis, and biodistribution of antibodies and antibody-coated carriers for targeted delivery of lysosomal enzymes to ICAM-1 versus transferrin receptor, Journal of Inherited Metabolic Disease, Sep. 12, 2012, vol. 36, pp. 467-477.
Hsu, J., et al., Enhancing Biodistribution of Therapeutic Enzymes In Vivo by Modulating Surface Coating and Concentration of ICAM-1-Targeted Nanocarriers, Journal of Biomedical Nanotechnology, Feb. 2014, vol. 10, No. 2, pp. 345-354.
Serrano , D., et al., A fibrinogen-derived peptide induces clathrin- and caveolaeindependent endocytosis in endothelial cells, FASEB, Apr. 1, 2012, vol. 26, No. S1, p. 605.3.
Hsu, J., et al., Enhanced Kidney and Heart Delivery of α-Galactosidase by Modulating Enzyme Load and Carrier Bulk-Concentration of ICAM-1-Targeted Nanocarriers, Molecular Genetics and Metabolism, Feb. 2012, vol. 105, No. 2, p. S37.
Hsu, J., et al., Specific Binding, Uptake, and Transport of ICAM-1-Targeted Nanocarriers Across Endothelial and Subendothelial Cell Components of the Blood-Brain Barrier, Pharmaceutical Research, Feb. 21, 2014, vol. 31, pp. 1855-1866.

(Continued)

*Primary Examiner* — Suzanne M Noakes
*Assistant Examiner* — Jae W Lee
(74) *Attorney, Agent, or Firm* — Hodgson Russ LLP

(57) ABSTRACT

Proteins, nucleic acids encoding the proteins, compositions comprising the proteins, and methods are provided. The proteins have the ability to be self-targeted to ICAM-1 and, if desired, enzymatically-released at acidic pH. The ICAM-1-targeting peptides are provided as single copies or multiples repeats, and can be separated by linkers from the enzyme segment, from which the ICAM-1 targeting peptides can be released, if desired, at acidic pH. These fusion proteins enhance the activity of the enzyme segment within or liberated from the fusion protein, and provide increased recognition and targeting of diseased organs, transport from the bloodstream across the endothelium into said diseased organ, and intracellular uptake and lysosomal trafficking by cells in them, both in peripheral tissues and the central nervous system. Representative nucleotide and amino acid sequences of these fusion proteins, as well as in vitro, cellular, and in vivo animal data are provided. The described proteins can be used as a protein therapy, a gene therapy, or an implanted cell therapy.

12 Claims, 21 Drawing Sheets
(10 of 21 Drawing Sheet(s) Filed in Color)
Specification includes a Sequence Listing.

(56) References Cited

OTHER PUBLICATIONS

Rappaport, J., et al., Clathrin-Mediated Endocytosis is Impaired in Type A-B Niemann-Pick Disease Model Cells and Can Be Restored by ICAM-1-Mediated Enzyme Replacement, Molecular pharmaceutics, Jun. 20, 2014, vol. 11, No. 8, pp. 2887-2895.

Hsu, J., et al., Targeting, Endocytosis, and Lysosomal Delivery of Active Enzymes to Model Human Neurons by ICAM-1-Targeted Nanocarriers, Pharmaceutical Research, Oct. 16, 2014, vol. 32, pp. 1264-1278.

Rappaport, J., et al., Altered Clathrin-Independent Endocytosis in Type A Niemann-Pick Disease Cells and Rescue by ICAM-1-Targeted Enzyme Delivery, Molecular Pharmaceutics, Apr. 7, 2015, vol. 12, No. 5, pp. 1366-1376.

Rappaport, J., et al., A Comparative Study on the Alterations of Endocytic Pathways in Multiple Lysosomal Storage Disorders, Molecular Pharamaceutics, Dec. 24, 2015, vol. 13, No. 2, pp. 357-368.

Ghaffarian, R. et al., Intra- and trans-cellular delivery of enzymes by direct conjugation with non-multivalent anti-ICAM molecules, Journal of Controlled Release, Sep. 28, 2016, vol. 238, pp. 221-230.

Manthe, R.L., et al., ICAM-1-targeted nanocarriers attenuate endothelial release of soluble ICAM-1, an inflammatory regulator, Bioengineering and Translational Medicine, Dec. 20, 2016, vol. 2, No. 1, pp. 109-119.

Garnacho, C., et al., Enhanced Delivery and Effects of Acid Sphingomyelinase by ICAM-1-Targeted Nanocarriers in Type B Niemann-Pick Disease Mice, Molecular Therapy, Jul. 5, 2017, vol. 25, No. 7, pp. 1686-1696.

Garnacho, C., et al., ICAM-1 targeting, intracellular trafficking, and functional activity of polymer nanocarriers coated with a fibrinogen-derived peptide for lysosomal enzyme replacement, Journal of Drug Targeting, Jul. 14, 2017, vol. 25, No. 9-10, pp. 786-795.

Serrano, D., et al., Endothelial cell adhesion molecules and drug delivery applications, Mechanobiology of the Endothelium, Chapter 9, Feb. 5, 2015, p. 42.

Muro, S., Strategies for delivery of therapeutics into the central nervous system for treatment of lysosomal storage disorders, Drug Delivery and Translational Research, May 31, 2012, vol. 2, pp. 169-186.

Solomon, M., et al., Lysosomal enzyme replacement therapies: Historical development, clinical outcomes, and future perspectives, Advanced Drug Delivery Reviews, Sep. 1, 2017, vol. 118, pp. 109-134.

Kelly, J.M., et al., Emerging therapies for neuropathic lysosomal storage disorders, Progress in Neurobiology, May 2017, vol. 152, pp. 166-180.

Futerman, A.H., et al., The cell biology of lysosomal storage disorders, Nature Reviews Molecular Cell Biology, Jul. 1, 2004, vol. 5, pp. 554-565.

Schuchman, E.H., The pathogenesis and treatment of acid sphingomyelinase-deficient Niemann-Pick disease, Journal of Inherited Metabolic Disease, Jul. 12, 2007, vol. 30, No. 5, pp. 654-663.

Germain, D.P., et al., Fabry disease, Orphanet Journal of Rare Diseases, Nov. 22, 2010, vol. 5, Article 30, pp. 1-49.

Mistry, P.K., et al., Gaucher disease: Progress and ongoing challenges, Molecular Genetics and Metabolism, Jan. 2017, vol. 120, Nos. 1-2, pp. 8-21.

A 1,3 = prior to enterokinase cleavage
2,4 = after enterokinase cleavage

B

1 = prior to cathepsinB cleavage
2 = after cathepsinB cleavage

A.

| Reaction Condition | Units/mg | | |
|---|---|---|---|
| | Neutral pH No cathepsinB | Acidic pH No cathepsinB | Acidic pH + cathepsinB |
| CHO3E7- ASM control (E) | 0.8 | 4.6 | 4.8 |
| CHO3E7- Fusion B | 0.9 | 5.7 | 8.8 |
| CHO3E7- Fusion C | 1.0 | 6.5 | 7.7 |
| CHO3E7- Fusion D | 0.9 | 6.0 | 7.6 |
| 293Hek- Fusion B | 0.9 | 5.8 | |
| Expi-CHO-S- Fusion B | 1.0 | 6.3 | 8.2 |
| CHO3E7- EK cleaved Fusion B | 1.5 | 7.2 | 10.6 |
| Expi-CHO-S- EK cleaved Fusion B | 1.5 | 7.3 | 10.5 |

B.

C.

D.

A

B

A

B $$LR = \frac{\%\frac{ID}{g} tissue}{\%\frac{ID}{g} blood}$$

ICAM-1 TARGETED FUSION ENZYMES

CROSS-REFERENCE TO RELATED APPLICATIONS

This application is a continuation of U.S. patent application Ser. No. 17/571,415, filed Jan. 7, 2022, which is a continuation of U.S. patent application Ser. No. 16/951,774, filed Nov. 18, 2020, now U.S. Pat. No. 11,248,029, which claims priority to U.S. provisional patent application No. 62/936,988, filed Nov. 18, 2019, the entire disclosures of each of which are incorporated herein by reference.

SEQUENCE LISTING

The instant application contains a Sequence Listing which is submitted in .xml format and is hereby incorporated by reference in its entirety. Said .xml file is named "070919_00143_ST26.xml", was created on Jan. 18, 2024, and is 81,051 bytes in size.

FIELD

The present disclosure relates generally to compositions and methods for treating lysosomal storage diseases (LSDs) and other diseases where lysosomal enzyme activities are beneficial.

BACKGROUND

LSDs are caused by defects in one or more hydrolytic enzymes of lysosomes in cells that digest biomacromolecules for cellular housekeeping. Lack of this function results in unwanted build-up of these molecules in cells and depending on the enzyme affected, specific substrate processing is impaired, and severity ranges from life-long debilitation to death. Supplementing defective enzymes by enzyme replacement therapy (ERT) is the most accepted treatment and a "universal" approach at present. However, there is an ongoing need for compositions and methods for use as ERT treatments. In addition, the activity of these lysosomal enzymes is also applicable to the treatment of other maladies. For instance, ceramide, the product of the activity of acid sphingomyelinase which is deficient in the LSD called types A and B Niemann-Pick disease, can induce cellular apoptosis when in excess. Hence, ERT methods and compositions for treatment of types A and B Niemann-Pick disease can also be used for cancer treatment. Similarly, mutations and defects in lysosomal enzyme glucocerebrosidase, which is deficient in the LSD called Gaucher disease, constitute a main hallmark in Parkinson's disease. It has been shown that increased activity of this enzyme improves the outcome of Parkinson's in animal models. Hence, ERT methods and compositions for treatment Gaucher disease can also be used for treatment of Parkinson's, but to date there remains an ongoing need for improved compositions and methods for prophylaxis and/or treatment of such ERT conditions. The present disclosure is pertinent to these needs.

BRIEF SUMMARY

The present disclosure provides compositions and methods that are useful for treating a variety of LSDs. The compositions include fusion proteins, for use in treating one or more LSDs, or additional diseases which may benefit from these enzyme activities.

Data presented in this disclosure demonstrate that, unexpectedly and unpredictably, the described fusion proteins exhibit enhanced enzymatic activity in conditions mimicking lysosomes, such as lysosomal pH, both as such fusion proteins and also after the enzyme segment has been liberated from the fusion protein, relative to the same enzyme that is not provided in a fusion protein context. This enhanced activity cannot be explained solely by the precise enzyme segment sequence used to form the fusion protein, because when the same enzyme segment is used to produce an enzyme without fusion to ICAM-1 targeting peptides, its activity is lower than that of the fusion protein or the enzymatic segment liberated from the fusion protein.

Data presented in this disclosure also support the use of the described fusion proteins for improved effects in cellular models and in mouse organs, including but not necessarily limited to the lung and brain, the latter of which no previously described enyme replacement therapy has been able to access in a therapeutic dose. With respect to the fusion proteins provided by the disclosure, they generally comprise: i) one or more intercellular adhesion molecule-1 (ICAM-1) targeting segments; ii) an enzyme segment that is catalytically active at the pH of a lysosome; iii) optionally a first protease cleavage sequence segment between i) and ii), and optionally, one or more of: iv) a secretion signal; v) a protein purification tag; and vi) a second protease cleavage signal, such as for use in protein purification of iv) and v) from the final product. The form and content of the fusion protein can be changed depending on, for example, its method of delivery.

In embodiments, the ICAM-1 targeting segment comprises amino acid SEQ ID NO 1 NNQKIVNIKEKVAQIEA (2γ3) or respective nucleotide sequence, which are comprised in fusion proteins containing amino acid or nucleotide SEQ ID NO 2, 3, 4, 5, 7, 8, 10, 11, 13, 14, 15, 16, 18, 19, 21, 22. This is in contrast to non-targeted enzyme sequences shown as control in some embodiments, such as amino acid or nucleotide SEQ ID NO 6, 9, 12, 17, 20, and 23. In both cases, that of fusion proteins or control non-targeted enzymes, nucleotide sequences provided include codon optimization for expression in mammalian cells, but this should not limit the use of other codon sequences encoding similar amino acids to those described. In some embodiments, the ICAM-1 targeting sequence may be repeated, and thus may appear in the fusion protein more than once. In embodiments, the enzyme segment comprises at least one of Acid sphingomyelinase (ASM), Alpha galactosidase (αGal), or Glucocerebrosidase (GCase), or a catalytically active fragment of any of said enzymes. The fusion protein may be delivered to an individual in need thereof using any of a variety of delivery forms and methods. The disclosure includes administration of the described fusion proteins, and polynucleotides encoding them, such as RNA or DNA or a suitable expression vector, or cells producing said proteins or nucleic acids or vectors. Thus, expression vectors, mRNA, and cDNAs encoding the fusion proteins are included. Also included are cells, including but not limited to mammalian cells, which further include but are not limited to human cells, that produce described fusion proteins or comprise the described vectors containing said sequences, as well as said cells to which a described fusion protein has bound, and/or which have internalized the fusion protein. The described proteins can be used as a protein therapy, a gene therapy, or by way of an implanted cell therapy, wherein the implanted cells express a described fusion protein. Organelles and cellular vesicles, such as lysosomes and exosomes, which comprise an intact or cleaved fusion protein, and organs, such as the lungs, liver or brain, to which these fusion proteins have been delivered are also included within the scope of the disclosure.

BRIEF DESCRIPTION OF THE FIGURES

The patent or application file contains at least one drawing executed in color. Copies of this patent or patent application publication with color drawing(s) will be provided by the Office upon request and payment of the necessary fee.

Figure 1:
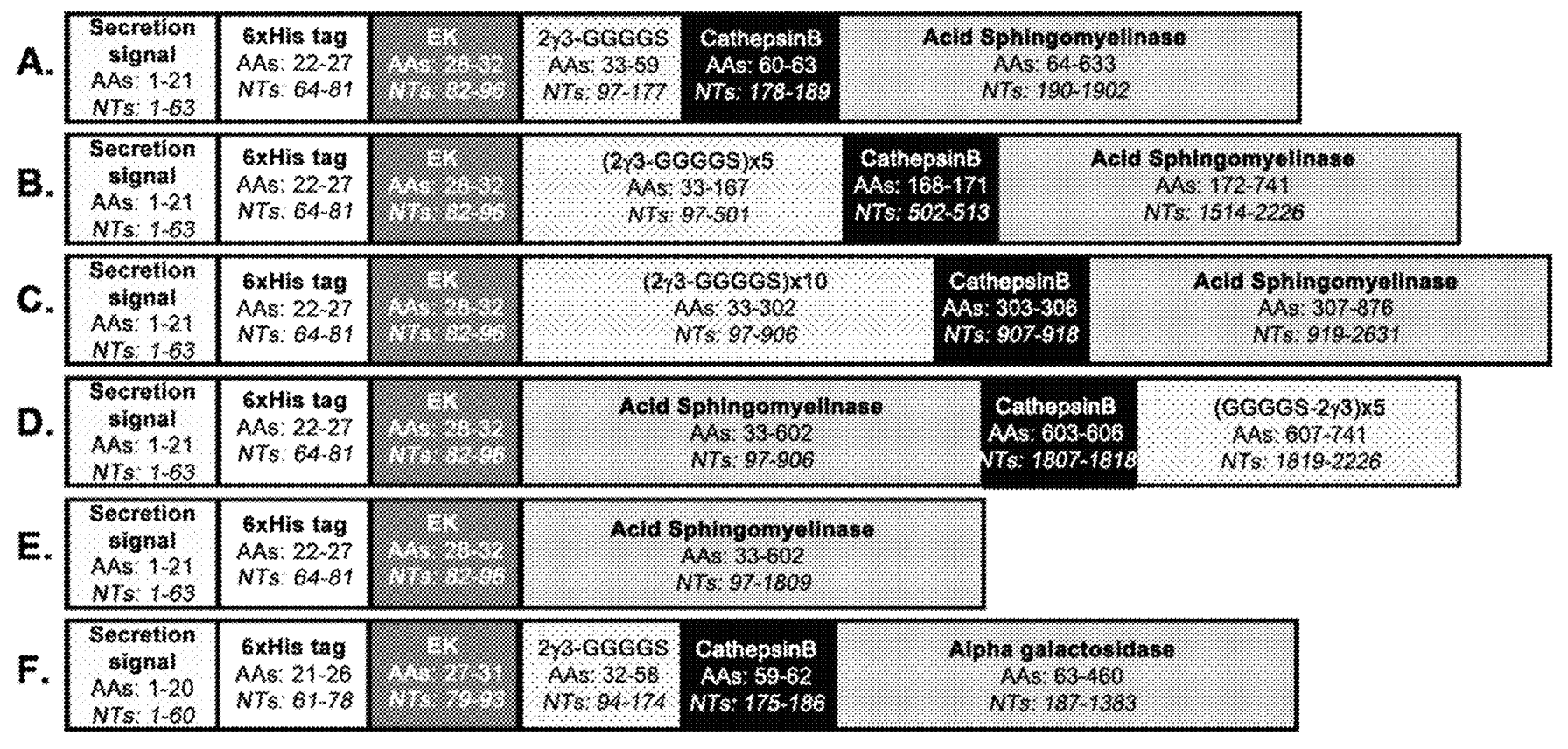
Figure 1:
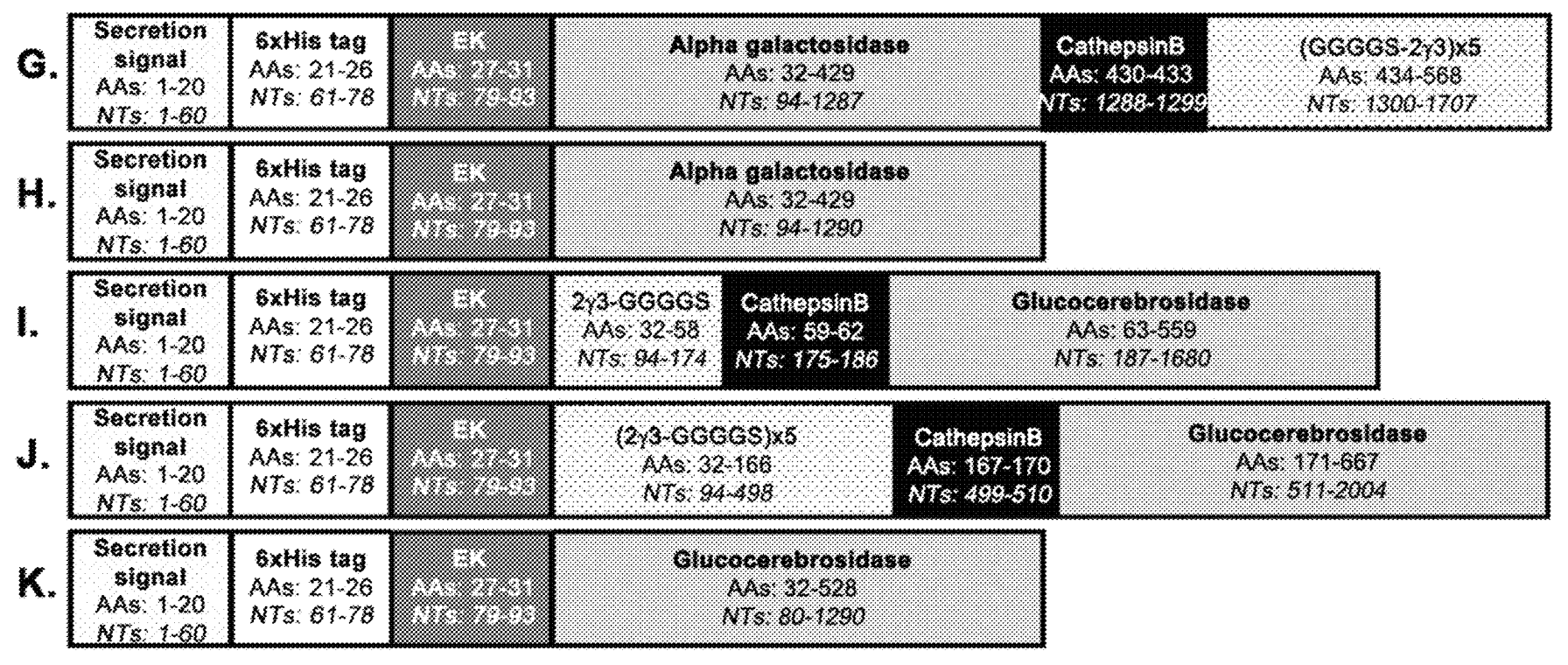

FIG. 1. Schematics of representative fusion proteins. (A.) Human acid sphingomyelinase (ASM) with one copy of the 2γ3 ICAM-1-targeting peptide at the amino terminus; (B.) human ASM with five tandem-repeats of the 2γ3 ICAM-1-targeting peptide at the amino terminus; (C.) human ASM with ten tandem-repeats of the 2γ3 ICAM-1-targeting peptide at the amino terminus; (D.) human ASM with five tandem-repeats of the 2γ3 ICAM-1-targeting peptide at the carboxyl terminus; (E.) human ASM control; (F.) human alpha galactosidase (αGal) with one copy of the 2γ3 ICAM-1-targeting peptide at the amino terminus; (G.) human αGal with five tandem-repeats of the 2γ3 ICAM-1-targeting peptide at the carboxyl terminus; (H.) human αGal control; (I.) human glucocerebrosidase (GCase) with one copy of the 2γ3 ICAM-1-targeting peptide at the amino terminus; (J.) human GCase with five tandem-repeats of the 2γ3 ICAM-1-targeting peptide at the amino terminus; and (K.) human GCase control.

FIG. 2. Cartoon depictions of in silico simulations of the structure of fusion protein from FIG. 1: (A) ASM fusion A in FIG. 1, (B) ASM fusion B in FIG. 1, (C) ASM fusion C in FIG. 1, (D) ASM fusion D in FIG. 1, (E) αGal fusion G in FIG. 1, and (F) GCase fusion J in FIG. 1.

FIG. 3. Photographs of gels after protein electrophoresis followed by western blotting of fusion proteins secreted by CHO cells. (A) prior to and (B) after fusion protein affinity purification via His-tag domain.

FIG. 4. Photographs of gels after protein electrophoresis followed by Coomassie blue after purification of (A) the same fusion enzyme from different cell sources or (B) different fusion enzymes in the same cell source. The data show reproducibility and purity of ICAM-1-targeted fusion enzymes.

FIG. 5. Photographs of gels after protein electrophoresis followed by Western blotting of ICAM-1-targeted fusion enzymes. (A) Prior to and after cleavage with enterokinase. (B) Prior to and after cleavage with cathepsin.

FIG. 6. Table (A.) showing comparative in vitro enzymatic activity of fusion proteins and respective non-fusion enzyme control and enterokinase (EK) cleaved fusion proteins, prior and after release with cathepsin B, at lysosomal versus neutral pH, and for fusions produced in different cell lines. (B., C., D.) Enzymatic activity, under lysosomal conditions of fusion proteins ((B.), fusion ASM; (C.) fusion GCase; (D.) fusion α-Gal) compared to respective control non-targeted enzymes.

FIG. 7. Graph showing cell binding and internalization of an ICAM-1-targeted fusion enzyme compared to respective control non-targeted enzyme.

FIG. 8. Graph (A.) and fluorescence microscopy images (B.) showing, respectively, uptake and lysosomal trafficking of an ICAM-1-targeted fusion enzyme by induced pluripotent stem cells (iPS)-derived Gaucher disease neurons, compared to respective control non-targeted enzyme.

FIG. 9. Results showing reduction of lysosomal storage in patient cells (fibroblasts) by ICAM-1-targeted fusion enzymes. (A) Fluorescence microscopy images, and (B) graph showing quantification of the level of a fluorescent substrate analogue degraded by fusion protein or non-fusion control delivered to cells from a type A Niemann-Pick patient. (C), (D) Graphs showing quantifications similar to (B) in the case of fusion proteins delivered to cells from Gaucher disease and Fabry disease, respectively. In all cases, graphs show increased therapeutic degradation of the respective substrate analog by the fusion protein compared to non-targeted control.

FIG. 10. Fluorescent micrographs (top) and quantification graph (bottom) showing that ICAM-1-targeted fusion enzymes normalize the size of lysosomes in Gaucher disease iPS-neurons, which are aberrantly enlarged compared to wildtype cells. Commercial Cerezyme only slightly attenuates the said lysosomal engorgement.

FIG. 11. Fluorescent micrographs showing lack of cytotoxicity of ICAM-1-targeted fusion proteins. (A) iPS-derived wildtype neurons compared to Gaucher disease neurons. (B) Gaucher neurons treated with control hydrogen peroxide, which is known to be cytotoxic, or with fusion protein.

FIG. 12. Model and graphical results showing transcytosis of ICAM-1-targeted fusion enzymes across models of the blood-brain barrier (BBB) and uptake by subjacent neurons. (A) Multi-cellular Transwell model. (B) Graph showing the concentration of fusion protein or control non-targeted enzyme in the apical or basolateral transwell chambers, demonstrating barrier function. (C) Graph showing that ICAM-1 blockage reduces the amount of fusion protein that interacted with the BBB. (D) Graph showing much higher BBB entrapment of the non-targeted enzyme compared to respective fusion protein. (E) Graph showing much higher uptake of fusion protein by Gaucher disease neurons compared to non-targeted enzyme.

FIG. 13. Graphs showing circulation of ICAM-1-targeted fusion enzymes in mice. (A) A fusion protein produced in two different cell sources compared to a non-targeted enzyme from which Olipudase® is derived. (B) Circulation of the same fusion protein from two different cell sources, before and after cleavage (Cl) of the His-tag domain.

FIG. 14. Graphs showing enhanced (A) lung and (B) brain distribution of ICAM-1-targeted fusion enzymes in mice compared to non-targeted enzyme.

FIG. 15. Graphs showing (A) higher blood levels and (B) lower lung and (C) brain levels of a fusion protein injected as such in mice compared to the same fusion protein loaded in a nanoparticle formulation.

FIG. 16. Graphs showing brain effects of ICAM-1-targeted fusion enzymes in mice following an every other day dosing schedule over a two week period. (A) Sphingomyelin (SM), the substrate of the ASM enzyme, which aberrantly accumulates in the brain of diseased mice (as in humans) was measured to be reduced upon treatment. (B) Esterified cholesterol (CE), which associates to sphingomyelin and also accumulates in the disease, was also measured to be reduced by fusion enzyme treatment. (C) Ceramide (CER), the product of the ASM catalytic reaction, which accumulates and causes side effects by Olipudase®, was determined.

FIG. 17. Graphs showing side effects of ICAM-1-targeted fusion enzymes in mice. (A.) Hematology parameters, (B.) markers of liver and kidney toxicity, (C.) body weight, and (D.) behavior, none showed signs of toxicity.

DETAILED DESCRIPTION

Unless defined otherwise herein, all technical and scientific terms used in this disclosure have the same meaning as commonly understood by one of ordinary skill in the art to which this disclosure pertains.

Figure 2:
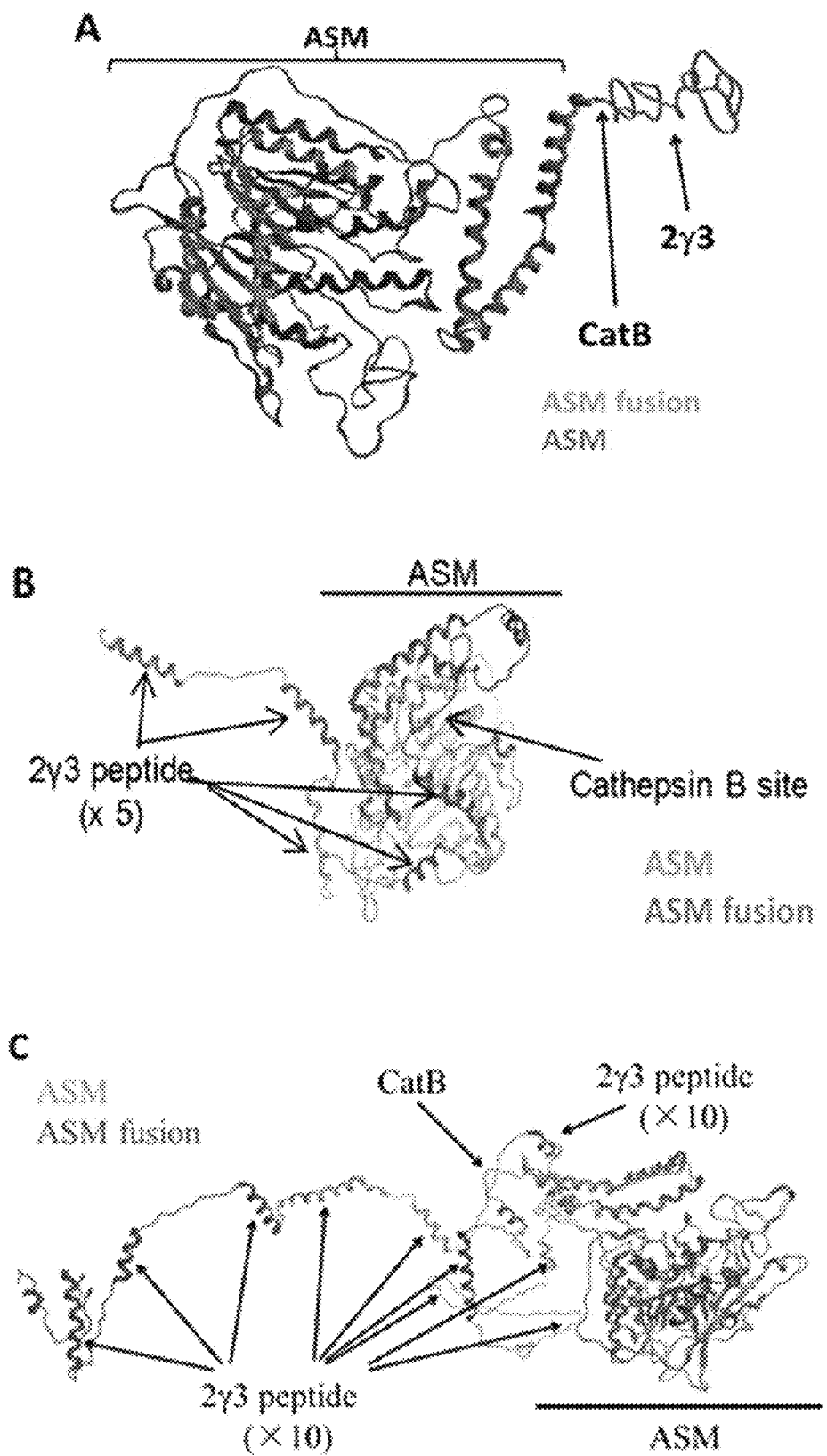
Figure 2:
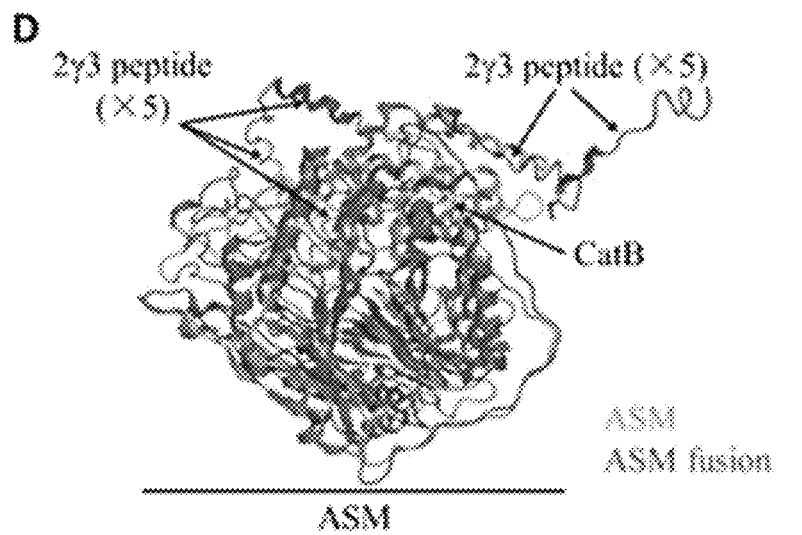
Figure 2:
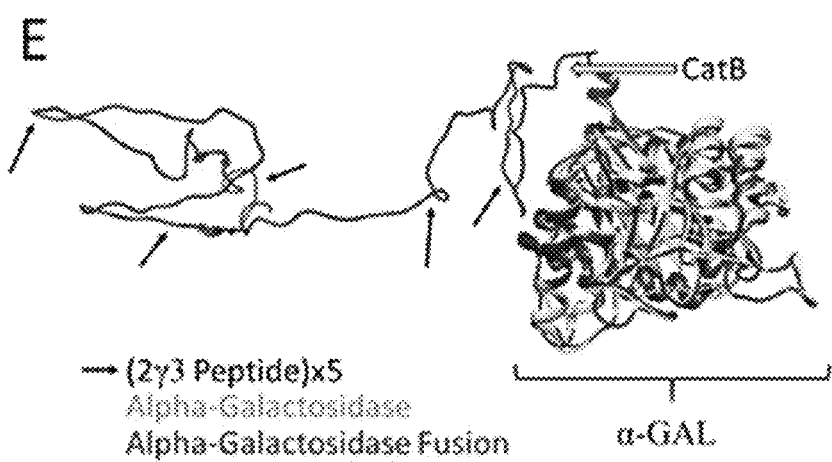
Figure 2:
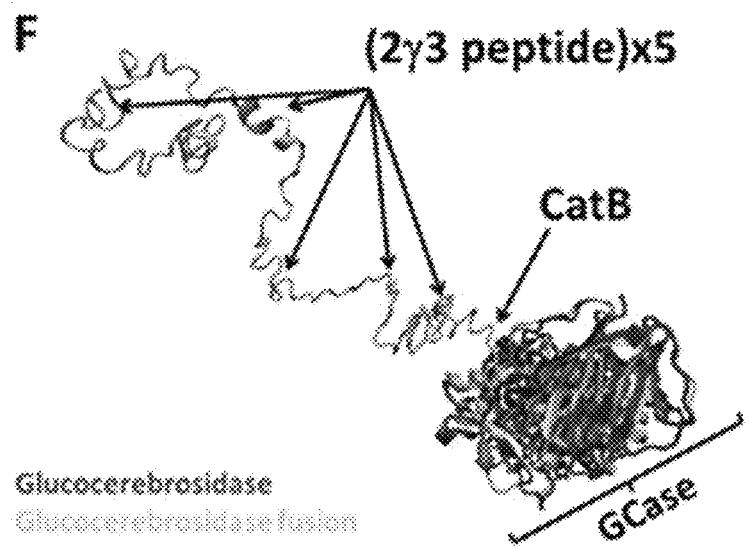

Every numerical range given throughout this specification includes its upper and lower values, as well as every narrower numerical range that falls within it, as if such narrower numerical ranges were all expressly written herein.

The disclosure includes all nucleotide and amino acid sequences described herein, and every nucleotide sequence referred to herein includes its complementary DNA sequence, and also includes the RNA equivalents thereof, and vice versa. All sequences described herein, whether nucleotide or amino acid, include sequences having 50.0-99.9% identity, inclusive, and including all numbers and ranges of numbers there between to the first decimal point. The identity may be determined across the entire sequence, or a segment thereof that retains its intended function. Homologous sequences from, for example, other enzymes, protease cleavage sites, secretion signals, and targeting moieties, are included within the scope of this disclosure, provided such homologous sequences also retain their intended function. Further, proteins of the present disclosure include functionally equivalent molecules in which amino acid residues are substituted for residues within the sequence resulting in a silent or conservative change. For example, one or more amino acid residues within the sequence can be substituted by another amino acid of a similar polarity that acts as a functional equivalent, resulting in a silent or conservative alteration. Substitutes for an amino acid within the sequence may be selected from other members of the class to which the amino acid belongs. For example, the nonpolar (hydrophobic) amino acids include, but are not limited to, alanine, leucine, isoleucine, valine, proline, phenylalanine, tryptophan, methionine, and combinations thereof. The polar neutral amino acids include, but are not limited to, glycine, serine, threonine, cysteine, tyrosine, asparagine and glutamine, and combinations thereof. The positively charged (basic) amino acids include, but are not limited to, arginine, lysine and histidine. The negatively charged (acidic) amino acids include aspartic acid, glutamic acid, and combinations thereof. Also included within the scope of the disclosure are proteins or fragments or derivatives thereof which exhibit the same or similar biological activity and derivatives which are differentially modified during or after translation, for example, by glycosylation, proteolytic cleavage, and the like.

Any result obtained using a method described herein can be compared to any suitable reference, such as a known value, or a control sample or control value, suitable examples of which will be apparent to those skilled in the art, given the benefit of this disclosure. In embodiments, any result obtained herein can be compared to a value obtained from analysis of components of the fusion proteins described herein, but wherein the components are configured differently, or are present in different copy numbers, or in a different stoichiometry, or are not present in the same, intact polypeptide. In embodiments, the disclosure provides for an improved result, relative to a result obtained using a targeting moiety and an enzyme that are present in the same composition, but are not present in the same polypeptide or were produced in the same polypeptide prior to enzyme release or liberation. In embodiments, the improved result comprises any one or combination of: improved and/or increased enzymatic activity, such as enzyme activity measured at a pH below physiological pH, such as in a lysosome, an improved pharmacokinetic property, improved bioavailability property, improved stability, improved shelf life, improved production yield, improved safety, improved duration of activity, improved biodistribution, improved incorporation into a lysosome, and/or an improved effect on any sign or symptom of a lysosomal storage disease. In embodiments, a result obtained using a composition described herein is improved, relative to a result obtained using a composition that comprises a particulate carrier. In an embodiment, a fusion protein of this disclosure displays increased targeting and/or catalytic activity than a control enzyme that is not a component of a fusion protein. In embodiments, a fusion protein of this disclosure displays a measurable improvement relative to a control enzyme that is not a component of a fusion enzyme. In embodiments, a 1-10 fold improvement is achieved. In non-limiting embodiments, a fusion protein of this disclosure displays ≥700-1000% (7-10-fold) better targeting and/or ≥300% (3-fold) better catalytic activity than a control enzyme such as acid sphingomyelinase (ASM), with ≥50% enhancement after protease cleavage of the enzyme.

Figure 6:
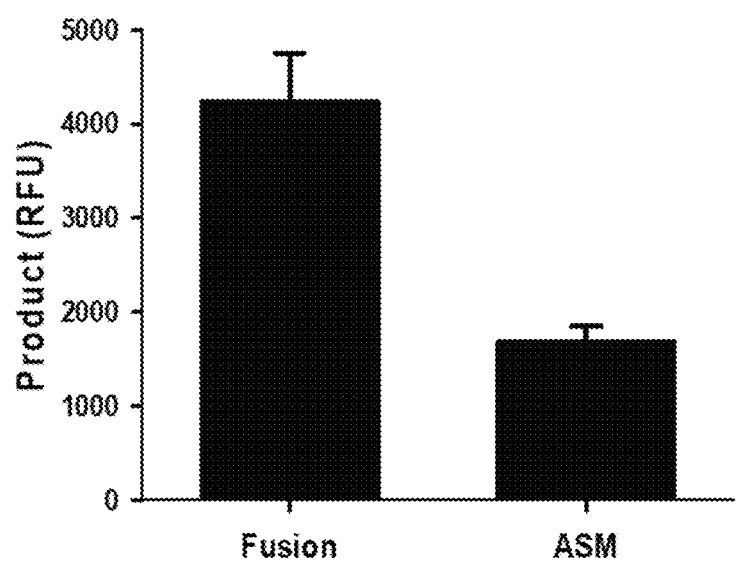
Figure 6:
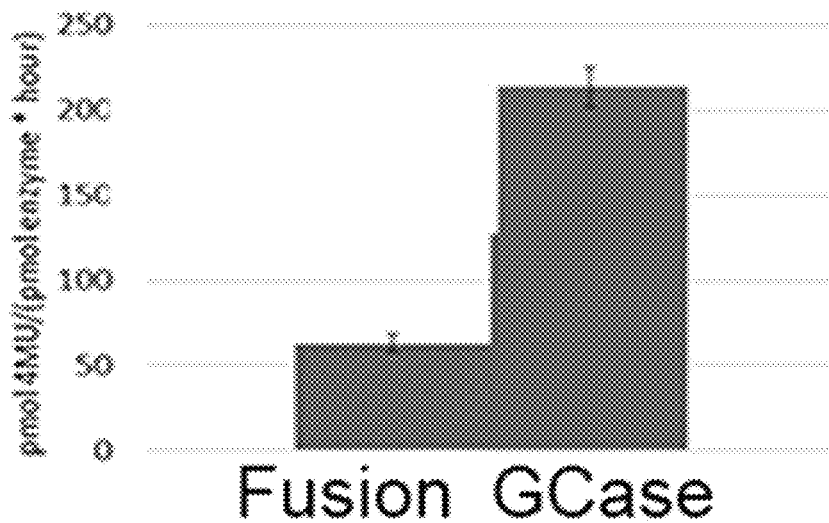
Figure 6:
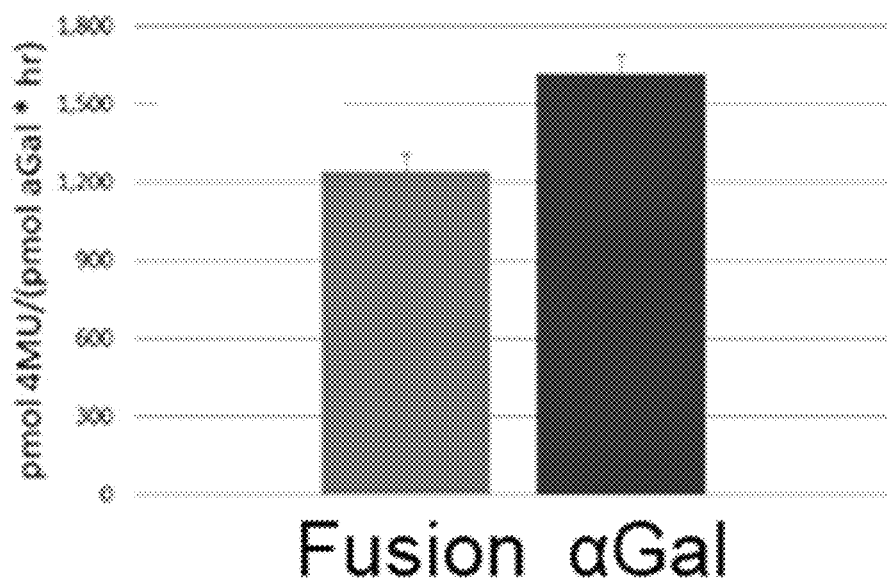

In connection with the foregoing, the present disclosure unexpectedly reveals, as in part demonstrated by Example 6 and FIG. 6 and the data in the Table referred to therein, that after cathepsin B cleavage of the fusion protein, the released enzyme, which no longer contains any other domains but the enzyme, exhibits more activity than an enzyme that was not previously part of a fusion protein. For example, both constructs sequence B and E (said constructs illustrated in FIG. 1) only differ in the targeting peptide and cathepsin B sequence. After cathepsin B cleavage, both products of sequences B and E are no different, yet after cathepsin B cleavage the product of B remains more active than the product of E. Without intending to be bound by any particular theory, it is considered that the fusion protein may have fold differently and, once liberated by protease activity, the enzyme part is more active. Hence, it is considered that the folding of the fusion protein is not the same than the non-fused enzyme. Thus, the disclosure provides for production of a fusion protein that contains a segment that is more active when freed from the fusion protein, relative to the same segment that is used in the absence of the fusion protein. In embodiments, a described fusion protein may therefore be considered to be a prodrug that is suitable for ERT, among other uses.

In one aspect, the disclosure comprises recombinant polypeptides, i.e., fusion proteins, for use in treating one or more LSDs, or additional diseases which may benefit from these enzyme activities, wherein the fusion proteins generally comprises:
  i) one or more intercellular adhesion molecule-1 (ICAM-1) targeting segments;
  ii) an enzyme segment that is catalytically active at the pH of a lysosome;
  iii) optionally a first protease cleavage sequence segment between i) and ii), and optionally, one or more of:
  iv) a secretion signal;
  v) a protein purification tag; and
  vi) a second protease cleavage signal, such as for use in protein purification, for removal of iv) and v) from the final product.

In embodiments, a fusion protein of this disclosure comprises or consists of any combination of i)-vi), provided at least i) and ii), and preferably at least i), ii) and iii) are present.

Representative and non-limiting configurations of segments of fusion proteins that are included in this disclosure are provided in Example 1 and FIG. 1. Representative amino acid sequences of each of these segments, and DNA sequences encoding them, are also provided herein, but are not intended to be limiting. Representative amino acid sequences for constructs A-K in FIG. 1 are provided below as amino acid sequences 13-23, respectively. Numbering in FIG. 1 corresponds with amino acid numbers in the annotated segments of the construct maps.

Where polypeptides of this disclosure are described, expression vectors encoding the polypeptides are also included. The expression vectors can be used in production of the polypeptides, and/or as therapeutic agents, such as DNA vaccines. Representative and non-limiting DNA sequences encoding proteins are provided below.

In embodiments, the ICAM-1 targeting segment comprises or consists of the sequence NNQKIVNIKEKVAQIEA (SEQ ID NO: 1), referred to herein from time to time as 2γ3. In embodiments, the 2γ3 sequence is repeated in the fusion protein. In embodiments, the 2γ3 sequence is repeated 2 to 10 times in the fusion protein. In embodiments, one 2γ3 sequence is proximal to another sequence, such as a Gly and Ser containing sequence. e.g., a linker sequence. In embodiments, a suitable Gly Ser sequence contains GGGGS (SEQ ID NO:24). In embodiments, distinct 2γ3 segments are separated by a segment comprising the sequence GGGGSGGGGS (SEQ ID NO:25). A variety of other linkers are known in the art and can be used with embodiments of this disclosure.

As an alternative to 2γ3, other ICAM-1 targeting peptide sequences can be used. Some examples include but are not necessarily limited to:

```
                              (SEQ ID NO: 26)
NNQKIVNLKEKVAQLEA;

(SEQ ID NO: 27)
NNQKLVNIKEKVAQIEA;

(SEQ ID NO: 28)
YPASYQR;

(SEQ ID NO: 29)
YQATPLP;

(SEQ ID NO: 30)
GSLLSAA;

(SEQ ID NO: 31)
FSPHSRT;

(SEQ ID NO: 32)
YPFLPTA
and (SEQ ID NO: 33)
GCKLCAQ.
```

In embodiments, a fusion protein described herein comprises a targeting segment and/or a lysosomal enzyme segment described in U.S. Pat. No. 8,778,307, from which the description of targeting moieties and lysosomal enzymes are incorporated herein by reference.

The enzyme segment of the fusion proteins described herein can comprise any enzyme or catalytic fragment thereof that is also described herein. In non-limiting embodiments, the enzyme or catalytic fragment thereof can function in a lysosome. In one embodiment, the enzyme is Acid sphingomyelinase (ASM). In another embodiment, the enzyme is Alpha galactosidase. In another embodiment the enzyme is Glucocerebrosidase (GCase). The amino acid sequences of each of these enzymes are known in the art. As noted above, representative and non-limiting sequences are provided in the examples below, and representative configurations on the enzyme segment in relation to the other components of the fusion proteins are shown in Example 1 and FIG. 1. Any fusion protein of this disclosure may comprise or consist of the sequence of functional fusion proteins depicted in FIG. 1.

In embodiments, the fusion proteins provided by this disclosure comprise a first and second protease cleavage sequence. In general, the first and second protease cleavage sites are distinct from one another, and do not appear elsewhere in the fusion proteins.

In embodiments, the first cleavage sequence comprises a sequence that is cleaved by any protease originally located in a lysosome, which may be located within endosomes or lysosomes, or secreted extracellularly by cells. In embodiments, the protease cleavage signal is cleaved by any endosomal cysteine proteases, such cysteine proteases known in the art as Cathepsins. In embodiments, the protease recognition sequence is recognized by cathepsin L or cathepsin B. In an embodiment, a protease cleavage site used in fusion proteins of this disclosure comprises the sequence GFLG (SEQ ID NO:34). In this regard, representative and non-limiting examples of first protease cleavage site configurations in relation to fusion proteins of this disclosure are shown in Example 1 and FIG. 1, and by way of the sequences provided with this disclosure. In FIG. 1, the represented protease cleavage site is designated as Cathepsin B. The first protease recognition cleavage sequence is configured such that it can liberate the enzyme segment from the remainder of the fusion protein upon cleavage in a suitable physiological solution, such as within a lysosome. In embodiments the protease is thus sequestered to a lysosome, and therefore the enzyme is only liberated subsequent to being taken up by the lysosome. In embodiments, the disclosure thus provides a prodrug that is only activated in the lysosome, or another environment with a sufficiently low pH level such that the protease is active. In embodiments, the prodrug itself has enzymatic activity.

In embodiments, a fusion protein of this disclosure comprises a second protease cleavage signal which is intended to be used in protein isolation and/or purification. In embodiments, the second protease cleavage site is distinct from the first protease cleavage site. In specific but non-limiting embodiments, second protease cleavage sites that can be used in embodiments of this disclosure include the EK cleavage sequence DDDDK (SEQ ID NO: 35), Tobacco etch virus (ENLYFQ (SEQ ID NO:36)), Factor Xa site IEGR (SEQ ID NO: 37), matrix metalloproteinase 9 (MMP-9) PXXXX, where X in position 2 and 3 is any residue, position 3 is a hydrophobic residue, and the X in position 5 is S or T (SEQ ID NO: 38), papain XXXXZRUXXX (SEQ ID NO:39) (where U is any residue but V), and Thrombin LVPRGS (SEQ ID NO:40).

In embodiments, a fusion protein of this disclosure comprises a secretion signal that is used for protein production and/or purification. Any suitable secretion signal can be used and many are known in the art. In one non-limiting embodiments, the secretion signal comprises METDTLLLWVLLLWVPGSTG (SEQ ID NO:41) or MGWSCIILFLVATATGVHSD (SEQ ID NO: 42).

In embodiments, fusion proteins provided in this disclosure may include protein purification tags. Any suitable protein purification tag can be used. In a non-limiting embodiment, a poly-histidine tag is used. A His-tag as used herein is a linear sequence of n histidine residues where n is typically 6-8.

In embodiments, the disclosure comprises administering therapeutically effective amounts of a described fusion protein to an individual in need thereof. In embodiments, the fusion protein to be used in a therapeutic method will have been produced and processed such that the secretion signal and the protein purification tag are removed from a portion of the fusion protein comprising the ICAM-1 targeting and enzyme segments by cleavage at the second protease cleavage sequence. In other embodiments, the purification tag is not removed.

Therapeutically effective amount means that amount of a recombinant polypeptide of this disclosure that will elicit the biological or medical response of a subject that is being sought. A “therapeutically effective amount” in certain implementations means an amount sufficient to prevent or reduce signs and/or symptoms of any disorder wherein an enzyme described herein could have a prophylactic and/or therapeutic benefit.

In embodiments, a therapeutically effective amount rescues an LSD disorder caused by a deficiency of one or more lysosomal enzymes. Effective amounts of polypeptides of this disclosure will depend in part on the particular LSD, the size and weight of the individual, etc. For any recombinant polypeptide disclosed herein, an effective dose can be estimated initially either in cell culture assays or in animal models, usually mice, rabbits, dogs, pigs, or non-human primates. The animal model is also used to achieve a desirable concentration range and route of administration. Such information can then be used to determine useful doses and routes for administration in humans. In embodiments, a fusion protein of this disclosure is administered such that it reaches the lungs and/or brain of an individual. Prophylactic dosing and uses are also included in this disclosure. Prophylactic or therapeutic doses can encompass a broad range of concentration including, but limited to, 0.01 mg/Kg to 20 mg/Kg.

In embodiments, the disclosure provides compositions comprising the described polypeptides, such as pharmaceutical formulations. In embodiments, the non-limiting compositions are free of particulate carriers. In embodiments, compositions are free of any one or combination of polystyrene nanocarriers, poly-lactic co-glycolic acid (PLGA) nanocarriers, polyethylene glycol (PEG), poly-lactic acid (PLA) nanocarriers, and biopolymeric dendrimers. In embodiments, a protein or polynucleotide encoding the protein as provided herein is not covalently or ionically coupled to a particle.

In embodiments, a pharmaceutical composition comprises a pharmaceutically acceptable carrier. Suitable carriers include, for example, diluents, adjuvants, excipients, or other vehicles with which the present complexes may be administered to an individual. Non-limiting examples of materials which can serve as pharmaceutical carriers include: sugars, such as lactose, glucose and sucrose; starches, such as corn starch and potato starch; cellulose, including sodium carboxymethyl cellulose, ethyl cellulose and cellulose acetate; powdered tragacanth; malt; gelatin; talc; excipients, such as cocoa butter; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer’s solution; ethyl alcohol; phosphate buffer solutions; and other non-toxic compatible substances employed in pharmaceutical formulations. The composition, if desired, can also contain minor amounts of wetting or emulsifying agents, or pH buffering agents. Some examples of compositions suitable for mixing a composition of this disclosure can be found in: Remington: The Science and Practice of Pharmacy (2005) 21st Edition, Philadelphia, Pa. Lippincott Williams & Wilkins.

Methods of using the therapeutic compositions include administration by any acceptable approaches including but not limited orally and parenterally. For example, the recombinant polypeptides can be administered intramuscularly, subdermally, subcutaneously, topically, intracranially, intratracheally, by instillation, intravenously, and intra-arterial. In embodiments, the fusion protein is loaded on or in cells for release in the body, e.g., cells such as erythrocytes can be loaded with proteins, injected in circulation, and release the protein over time which then target the intended organs. In embodiments, a fusion protein of the disclosure is administered in combination with any suitable nanoparticles. In embodiments, a composition comprising a fusion protein may be administered by a device, such as a medical pump, implant, patch, or chip.

In embodiments, a polypeptide or polynucleotide encoding such polypeptide is administered to an individual in need thereof. In embodiments, the individual in need thereof has been diagnosed with or is suspected of having any disorder that is correlated with a lysosomal storage disease, non-limiting examples of which include Pompe Disease, GM1 gangliosidosis, Tay-Sachs disease, GM2 gangliosidosis, Sandhoff disease, Fabry disease, Gaucher disease, metachromatic leukodystrophy, Krabbe disease, Niemann-Pick disease type A, Niemann-Pick disease type B, Niemann-Pick disease type C, Niemann-Pick disease type D, Farber disease, Wolman disease, Hurler Syndrome, Scheie Syndrome, Hurler-Scheie Syndrome, Hunter Syndrome, Sanfilippo A Syndrome, Sanfilippo B Syndrome, Sanfilippo C Syndrome, Sanfilippo D Syndrome, Morquio A disease, Morquio B disease, Maroteaux-Lamy disease, Sly Syndrome, α-mannosidosis, β-mannosidosis, fucosidosis, aspartylglucosaminuria, sialidosis, mucolipidosis II, mucolipidosis III, mucolipidosis IV, Goldberg Syndrome, Schindler disease, cystinosis, Salla disease, infantile sialic acid storage disease, Batten disease, infantile neuronal ceroid lipofuscinosis, or prosaposin.

In alternative embodiments, the individual has any type of cancer, or Parkinson’s disease. In embodiments, the cancer is a blood cancer or a solid tumor, either primary or metastatic, that affects any part of the body.

The disclosure includes expression vectors encoding the fusion proteins, and methods of making the fusion protein using the expression vectors. In general, a method of making the fusion proteins comprises allowing expression of an expression vector encoding the fusion proteins in a cell culture, and separating the protein from the cell culture using any suitable approach. The proteins can be separated and purified to any desired degree of purity. In certain embodiments, the disclosure includes cell cultures that contain the expression vectors. In certain embodiments, the cell cultures are eukaryotic cell cultures.

In embodiments, the disclosure includes administering to an individual an expression vector encoding a fusion protein described herein, or otherwise configured to result in expression of the fusion protein once the expression vector is introduced into a cell. In embodiments, any of a variety of retroviral vectors, such as lentiviral vectors, or adenoviruses, adeno-associated viruses, herpes, and vaccinia viruses can be used. In embodiments, RNA encoding the fusion protein can be directly injected into the cells or otherwise introduced to the individual. Polynucleotide vectors can include modified nucleotides or phosphate backbone moieties, many suitable examples of which are known in the art. CRISPR/

Cas technology can also be used to introduce in the genome the coding sequence of the described fusion proteins.

In one representative approach, which is further illustrated by the Examples presented below, 5 tandem repeats of 2γ3 were cloned for enhanced ICAM-1 affinity, each repeat separated from the next by a short peptide linker to enable their independent folding (targeting domain=135 amino acids). At the carboxyl-terminus of the targeting domain, a 4 amino acid cathepsin B sequence was placed to enable lysosomal cleavage and release of human ASM, which was cloned at the carboxyl-terminus of the release domain. This catalytic domain is 570 amino acids-long and encompasses human ASM mRNA sequence starting at His62, which lacks the enzyme's natural secretion sequence. The targeting+cleavage+catalytic cassette ("functional domains") was preceded at the amino-terminus by "production domains", consisting of a 21 amino acid signal peptide for secretion of the fusion protein from transfected cells into the culture medium, a 6 amino acid His-tag for affinity purification, and a 5 amino acid enterokinase cleavage site to separate the production domains from the functional domains which constitute the intended fusion protein. The full sequence was cloned into a plasmid vector to enable transient and stable expression in mammalian cells. In addition, computer predictions were pursued to examine the resulting conformation of the targeted fusion proteins. Results suggested that the designed fusion protein would match the folding of respective human wild-type enzymes which endogenously reside in lysosomes of our bodies.

To produce data described in the Examples below, a plasmid vector containing the expression cassette for an ASM fusion protein was transfected in CHO-3E7, Expi-CHO-S and 293-6E cells. In all cases, collection of the cell medium 5-7 days post-transfection, followed by affinity purification using the His-tag domain and electrophoresis under reducing conditions, showed a protein band of ≈80 KDa (expected size), quantified as ≈90% purity. Similar cells were transfected with plasmids containing the expression cassettes for GCase and αGal fusion proteins, respectively, which also resulted in the production of proteins of expected size and purity ranging from 39 to 90%. Subsequent optimization of the purification protocol raised purity to ≥90% in all cases. Electrophoresis under non-reducing conditions revealed monomeric, dimeric, and tetrameric protein at ≈25%, 25%, 50% for 293 cells and 30%, 15%, 55% for CHO cells in the case of ASM fusion protein. This was because natural ASM assembles into monomeric and oligomeric forms in the body, all of which are functional. Three independent production rounds in CHO cells showed high reproducibility. The production yield was high, e.g. ≈5-8 mg/L of culture for CHO-3E7 and ≈35-40 mg/mL for Expi-CHO-S. Western blot (WB) validated that the fusion protein contained His-tag and enzyme modules, for which antibodies are available. It also validated that the His-tag was cleaved off the fusion protein by enterokinase, which was then removed by size exclusion chromatography for a final purity of ≈85%. In the case of an ASM fusion protein, WB also showed that cathepsin B cleavage released a protein band of ≈70 KDa recognized by anti-ASM, as expected. Similar results were obtained for GCase fusion protein and αGal fusion protein.

When hundreds of copies of γ3 peptides are coupled on the surface of polymer nanoparticles, particles target human and mouse ICAM-1 (Garnacho et al., J Pharm Exp Ther, 340:638 & Garnacho et al., J Drug Targeting. 25:786). However, these peptides were never tested outside the context of these high affinity nanoparticles. We observed that, in CHO cells that expressed 2γ3-ASM fusion protein, ASM was stained using anti-ASM+FITC−secondary antibody, abundant label associated with the cells. This was in contrast to non-transfected CHO cells, despite the fact that CHO cells express natural ASM, which we verified by Western blotting (WB). Fluorescence detection could have been enabled by enhanced expression of fusion protein over natural ASM, yet we had demonstrated that fusion protein is secreted to the cell medium. In fact, WB validated the almost absence of fusion protein in cell lysates vs. the cell medium. Therefore, the fluorescence signal may be due to binding of secreted fusion protein on cells, indicating ICAM-1 binding, as WB verified the presence of ICAM-1 expression in these CHO cells. In addition, incubation of purified fusion protein with HUVEC cells (known to express ICAM-1) for 3 h at 37° C., followed by cell fixation, permeabilization and staining using anti-ASM+FITC-secondary antibody, showed bright green-FITC dots indicative of endo-lysosomal uptake of the fusion protein by cells. This was not observed when HUVECs were incubated with control non-targeted ASM (Olipudase), demonstrating the targeting ability of the fusion protein.

After demonstrating the presence of an ASM enzyme sequence in the fusion protein, its catalytic function was assessed. For this purpose, a commercial kit was used, which is based on catalytic hydrolysis of sphingomyelin and final production of fluorescent Resorufin, which can be quantified by spectrofluorometry. As further demonstrated in the Examples below, in the absence of cathepsin B or low cathepsin B concentration, some ASM activity was found over negative control levels, indicating that the fusion protein is active. More importantly, ASM activity doubled upon raising cathepsin B concentration, indicating that a fully active enzyme results upon release by cathepsin B. Furthermore, ASM activity increased by several fold at pH 4.5, which is reflective of lysosomal conditions, vs. neutral pH 7.4. These results suggest that maximal ASM activity will be obtained upon lysosomal delivery of the fusion protein, which would prevent any undesirable ASM activity in circulation, observed for Olipudase. Similar results were found for GCase and αGal fusion proteins, indicating that all fusion proteins have prevalent activity under lysosomal conditions. In addition, the catalytic activity of the fusion protein under lysosomal conditions was 2-3-fold enhanced compared to the control ASM. The activity of GCase and αGal fusion proteins was also enhanced compared to their respective controls.

Next, both the targeting and trafficking of fusion proteins were compared against similar control non-targeted enzymes. For example, in a pharmacological model of ASM deficiency, cell association of control ASM was much lower (7-10 fold by immunofluorescence detection and 3-4 fold by radioisotopic tracing) compared to ASM fusion protein. Similarly, association of GCase fusion protein to induced pluripotent stem cell (iPS)-derived neurons from a Gaucher patient was about 3 fold enhanced compared to respective control non-targeted enzyme. In the latter case, GCase fusion was visualized to traffic to lysosomes in neurons, while control Cerezyme® used at similar activity units was not visible.

Skin fibroblasts from patients diagnosed for ASM deficiency (NPD) and skin fibroblasts from healthy individuals were tested as a part of this disclosure. No personal data was associated with them. First, both healthy and diseased cells were incubated overnight with a commercial fluorescent sphingomyelin (BODIPY-FL-C12-sphingomyelin), a substrate analogue for ASM, which fluoresces green. Microscopy examination of said cells showed that diseased cells accumulated increased levels of sphingomyelin compared to healthy cells. Incubation of diseased cells for 5 h with control, non-targeted ASM (from which Olipudase was derived) vs. similar concentration of fusion protein resulted in differential degradation of the stored sphingomyelin. Control ASM only degraded 4% of the sphingomyelin stored in diseased cell vs. 27% degradation for the fusion protein, which represents a 6-7-fold improvement in the intracellular activity after only 5 h incubation. Similar results were found for GCase fusion protein and αGal fusion proteins when compared to respective control enzymes in skin fibroblasts from patient with Gaucher disease and Fabry disease, respectively.

Apart from enhanced enzymatic activity and substrate reduction observed by fusion proteins, additional effects were studied. For instance, fluorescence microscopy showed that acidic compartments such as lysosomes were aberrantly engorged in iPS-derived neurons from Gaucher patients compared to healthy wildtype counterparts. Incubation with GCase fusion protein normalized the size of said compartments while control Cerezyme exerted only a partial reduction. In addition, GCase fusion protein did not cause cytotoxicity after 48 incubation with iPS-derived neurons compared to a positive control, $H_2O_2$, which is known to cause cell death.

Next, the capacity of fusion proteins to be transported across the BBB was tested in a multicellular model consisting of human brain endothelial cells, human astrocytes and iPS-derived neurons from a Gaucher patient. After validating the barrier function of this model, GCase fusion protein was demonstrated to cross this BBB model and accumulate in the subjacent neurons, while control non-targeted enzyme was trapped in the BBB and did not significantly accumulate in neurons after 24 h incubation. Additionally, pre-incubation of this model with anti-ICAM antibody blocked the interaction of GCase fusion with cells, while pre-incubation with anti-mannose-6-phosphate receptor antibody did not. This demonstrated an ICAM-1, not mannose-6-phosphate receptor, mediated process.

The ASM knock-out mouse mimics both type A (neurological) and type B (peripheral) NPD. We radiolabeled samples and injected i.v. 0.13 mg/Kg of $^{125}$I-ASM-fusion protein or $^{125}$I-ASM in mice. Measurement of the radiotracer in blood and tissues showed that both proteins disappeared fast from the circulation: by 1 h, 20% of the injected dose (% ID) was in blood for ASM and only 8.5% ID for the ASM-fusion protein. Since Olipudase has shown systemic toxicity, a reduction in circulation time for ASM-fusion protein may improve this. ASM-fusion protein was detected in the brain, lung, liver, spleen, heart, and kidneys, all of which need treatment. The localization ratio, which is the tissue-to-blood accumulation (% ID per gram in an organ over % ID per gram in the blood), was increased for the ASM-fusion protein over control ASM even after only 1 h after one single dose: e.g., 35% increase in the brain (main target in type A NPD) and 80% increase in the lung, 3.3-fold in the liver, and 3-fold in the spleen (main targets in type B NPD). Hence, the fusion protein had enhanced in vivo delivery. In addition, this fusion protein was loaded on nanoparticles, which showed enhanced removal from the circulation and enhanced targeting to peripheral organs (e.g. the lungs) and the central nervous system (e.g. the brain) compared to fusion protein not loaded in nanoparticles. Next, mice were injected i.v. with 0.6 mg/kg of ASM-fusion protein without nanoparticles, every two days for a total of 6 injections, vs. mice injected with control buffer. At the end of the experiment, blood and organs were measured for sphingomyelin and cholesterol, disease hallmarks. Multiple sphingomyelin and cholesterol species were reduced, which is needed for therapy. Ceramide product (associated to Olipudase side effects) was not significantly increased. An example is shown below for the brain, the organ where Olipudase has no effect. As seen, in the Examples below, 10 sphingomyelin species and 16 cholesterol species were lowered upon treatment with ASM-fusion protein. Instead, only a ceramide species was slightly increased upon treatment which suggest lack of any major ceramide burst which may lead to relevant side effects.

Mice were monitored each day during the study. The mice showed no statistical changes in the body weight for ASM-fusion protein vs. control buffer, or for parameters such as grooming and general activity. Hematological (RBCs, all types of leukocytes, platelets) and biochemical (glucose) tests showed no statistically significant changes between mice injected with fusion protein vs. control buffer, and this was also true for renal toxicity markers (BUN, creatinine) and hepatic toxicity markers (alkaline phosphatase). This, together with no overt increase in ceramide, the ASM product which is burst-produced and leads to toxicity of current ASM-Olipudase ERT, shows relative safety of the presently provided fusion strategy.

It will be apparent to those skilled in the art that the foregoing description illustrates: 1) fusion proteins of this disclosure have been generated and encompass various configurations of a 2γ3 ICAM-1 targeting module and ASM, GCase, or αGal catalytic modules, separated by a cathepsin B cleavable peptide which leads to the release of functional enzyme within the lysosomes; (2) these fusion protein possess enhanced targeting, trans-BBB transport, cellular uptake, and lysosomal trafficking in pharmacological cell models and patient cells; and (3) fusion proteins provide enhanced catalytic activity under lysosomal conditions in vitro and in cell cultures, in comparison to control non-targeted enzymes and commercial enzymes; (4) they provide enhanced substrate reduction and lysosomal size reduction; and (5) these fusion proteins surpassed both the targeting and functional performance, with respect to control enzyme, in mouse models (particularly the brain), with no appreciable side effects.

The foregoing results are reiterated and expanded upon by the following Examples, which are presented in order to more fully illustrate the preferred embodiments of the invention and should in no way be construed as limiting the scope of the invention. Unless indicated otherwise, for representative demonstrations described in these Examples, controls correspond to the cDNA or amino acid sequence of non-targeted enzymes, while all other cases represent the cDNA or amino acid sequence of fusion proteins consisting of an ICAM-1 targeting domain and an enzyme domain, separated by a cleavage domain to release the enzyme domain from the targeting domain in the lysosome. In all cases, control and others, the cDNA or amino acid sequences may contain at the amino terminus of the proteins a signal peptide domain for secretion, followed by a tag domain for purification, followed by a domain for cleavage of said signal and tag domains.

EXAMPLES

Example 1, illustrated by FIG. 1, Expression cassette of ICAM-1-targeted fusion enzymes. Schematics of the domain design for: (A) Human acid sphingomyelinase (ASM) with one copy of the 2γ3 ICAM-1-targeting peptide at the amino terminus; (B) human ASM with five tandem-repeats of the 2γ3 ICAM-1-targeting peptide at the amino terminus; (C) human ASM with ten tandem-repeats of the 2γ3 ICAM-1-targeting peptide at the amino terminus; (D) human ASM with five tandem-repeats of the 2γ3 ICAM-1-targeting peptide at the carboxyl terminus; (E) human ASM control; (F) human alpha galactosidase (αGal) with one copy of the 2γ3 ICAM-1-targeting peptide at the amino terminus; (G) human αGal with five tandem-repeats of the 2γ3 ICAM-1-targeting peptide at the carboxyl terminus; (H) human αGal control; (I) human glucocerebrosidase (GCase) with one copy of the 2γ3 ICAM-1-targeting peptide at the amino terminus; (J) human GCase with five tandem-repeats of the 2γ3 ICAM-1-targeting peptide at the amino terminus; and (K) human GCase control. Controls correspond to the non-targeted enzymes, while all other cases represent fusion proteins consisting of a targeting domain and an enzyme domain, separated by a cathepsin B cleavage domain to release enzyme domain from the targeting domain in the lysosome. In all cases, control and others, the expression cassettes contain at the amino terminus of the fusion proteins a signal peptide domain for secretion, followed by a His-tag domain for purification, followed by an enterokinase domain (EK) for cleavage of said signal and tag domains. Also, in all cases, human enzymes are truncated at their amino termini to eliminate endogenous signal peptides. From these amino acid (AAs) designs, the corresponding nucleotide (NTs) designs were made using codon optimization for the intended expression in mammalian cells.

Example 2, illustrated by FIG. 2. Predicted structure of ICAM-1-targeted fusion enzymes. A) Fusion protein containing one copy of the 2γ3 ICAM-1-targeting peptide at the amino terminus, followed by a cathepsin B (CatB) cleavage site for lysosomal release of truncated human acid sphingomyelinase (ASM). (B) Fusion protein containing five tandem-repeats of the 2γ3 ICAM-1-targeting peptide at the amino terminus, followed by CatB cleavage site for lysosomal release of truncated human ASM. (C) Fusion protein containing ten tandem-repeats of the 2γ3 ICAM-1-targeting peptide at the amino terminus, followed by CatB cleavage site for lysosomal release of truncated human ASM. (D) Fusion protein containing truncated human ASM at the amino terminus, followed by CatB cleavage site for lysosomal release, followed by five tandem-repeats of the 2γ3 ICAM-1-targeting peptide at the carboxy terminus. (E) Fusion protein containing truncated human alpha galactosidase (αGal) at the amino terminus, followed by CatB cleavage site for lysosomal release, followed by five tandem-repeats of the 2γ3 ICAM-1-targeting peptide at the carboxy terminus. (F) Fusion protein containing five tandem-repeats of the 2γ3 ICAM-1-targeting peptide at the amino terminus, followed by CatB cleavage site for lysosomal release of truncated human glucocerebrosidase (GCase).

Figure 3:
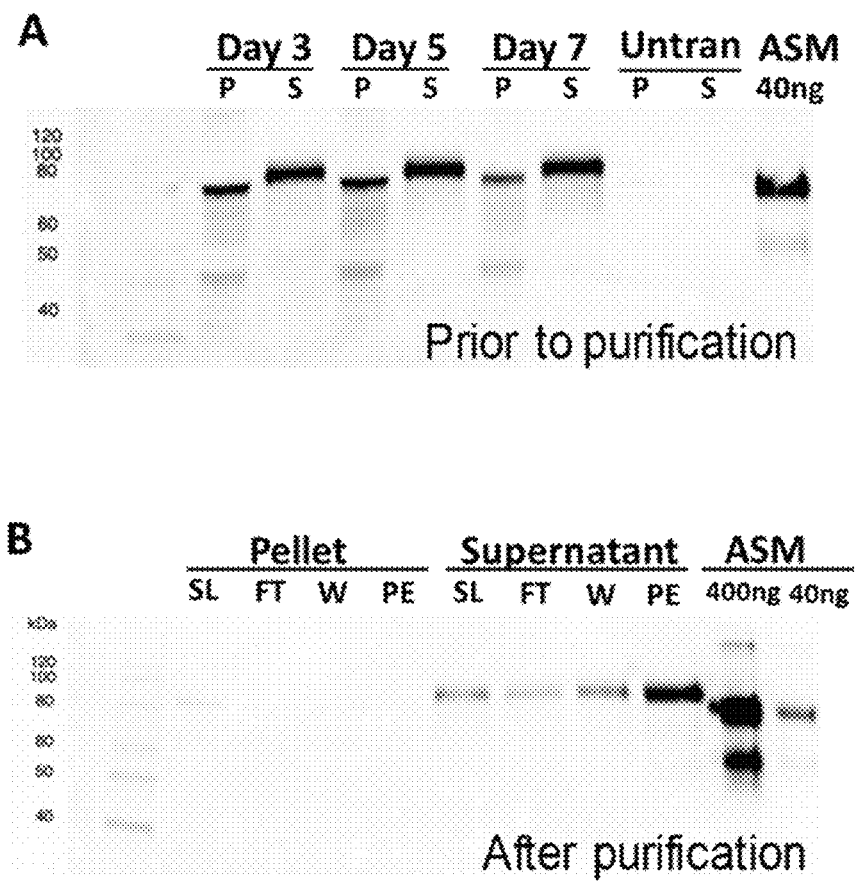

Example 3, illustrated by FIG. 3. Production and purification of ICAM-1-targeted fusion enzymes. Protein electrophoresis followed by western blotting of fusion proteins secreted by CHO cells, shown (A) prior and (B) after fusion protein affinity purification via His-tag domain. Fusion protein is that shown in panel (B) in Example 2 above. (A) Higher molecular weight band in the cell medium supernatant(S) corresponds to the fusion protein, versus the low molecular weight band in the cell pellet (P), which corresponds to the cell endogenous enzyme. ASM=control purified recombinant enzyme has lower molecular weight than fusion protein and similar to endogenous ASM in cells. Different production days are shown. (B) No fusion protein is purified from the cell pellet fractions (Sample (SL), Flow-through after passing through an anti-his tag affinity column (FT), wash fraction (W), and pooled elution from the affinity column (PE)), since endogenous ASM does not have a His-tag. Fusion protein is present in the corresponding fractions from the cell medium supernatant, verifying its secretion. The pooled eluted fraction of the cell medium supernatant is enriched for the fusion protein. Untran=untransfected control cells.

Figure 4:
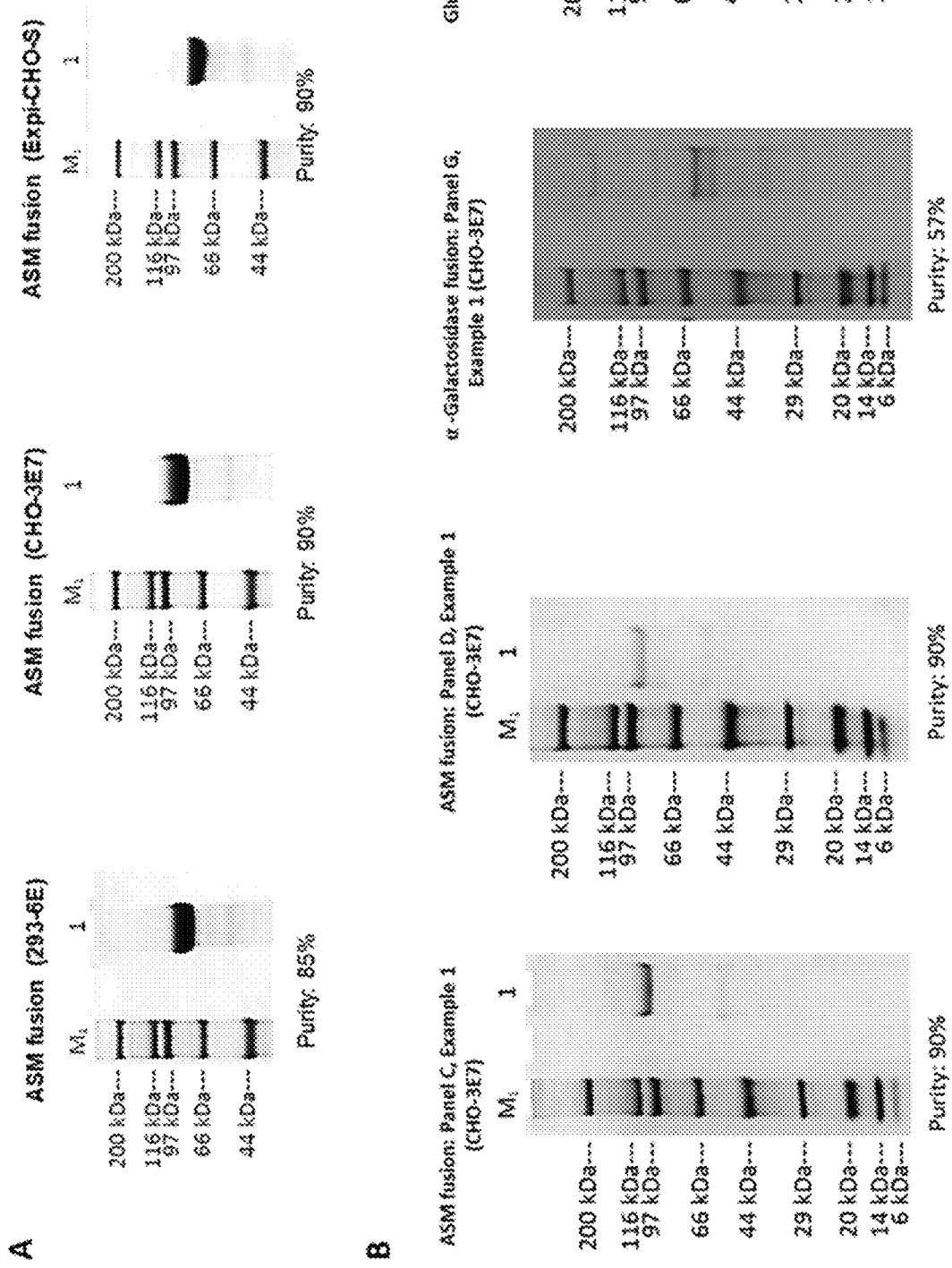

Example 4, illustrated by FIG. 4. Reproducibility and purity of ICAM-1-targeted fusion enzymes. (A) Electrophoresis followed by Coomassie blue staining demonstrate that the fusion protein in panel (B) in Example 2 above was independently produced in and purified from three mammalian cell lines (293-6E, CHO-3E7, and Expi-CHO-S), showing great reproducibility and purity. (B) Other fusion proteins are shown, including fusion proteins in panels C, D, G and J (Example 1 above) all produced in the CHO-3E7 cell line.

Figure 5:
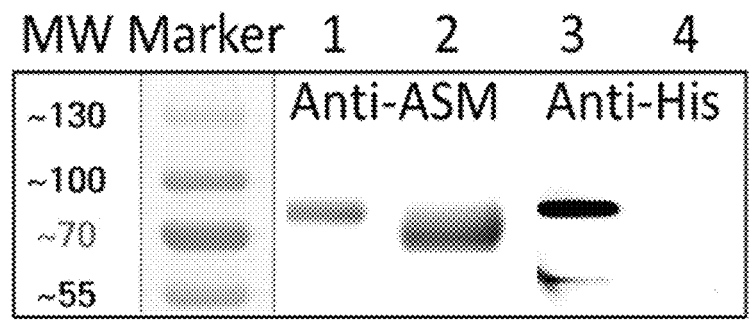
Figure 5:
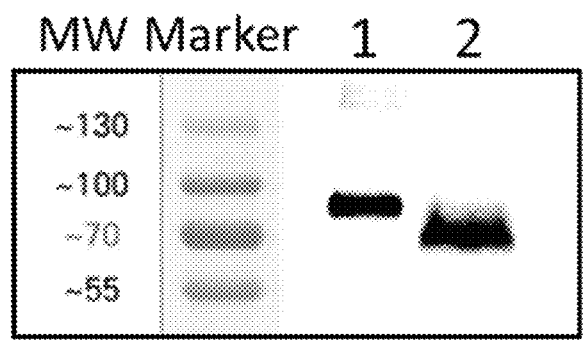

Example 5, illustrated by FIG. 5. Western blotting of ICAM-1-targeted fusion enzymes. (A) After purification of the fusion protein shown in panel (B) in Example 2 above, Western blotting was conducted using antibody to detect the enzyme domain (ASM) and the His-tag domain used for purification, both prior and after enterokinase cleavage to remove the His-tag from the fusion protein. (B) Similarly, the purified fusion protein shown in panel (B) in Example 2 above was cleaved with cathepsin B to remove the targeting group from the enzyme and western blotting was conducted to determine the enzyme domain (ASM). The lower molecular weight band corresponds to that of the ASM portion of the fusion protein.

Example 6, illustrated by FIG. 6. Enzymatic activity of ICAM-1-targeted fusion enzymes. (A) The table shows the comparative in vitro enzymatic activity of fusion proteins and respective non-fusion enzyme control as well as some enterokinase (EK) cleaved fusion proteins, prior and after release with cathepsin B, at lysosomal versus neutral pH, and for fusions produced in different cell lines where B, C, D and E are as in Example 1. (B) Enzymatic activity, under lysosomal conditions, of fusion protein B in Example 1 was additionally compared to full recombinant ASM produced by He et al. (He, Miranda et al. 1999), which served as basis for Genzyme Olipudase®. The fusion enzymes are more active in lysosomal conditions (acidic) compared to circulation conditions (neutral) and are even more active after removal of the His tag, as expected. (C) Enzymatic activity, under lysosomal conditions, of GCase fusion protein J in Example 1 compared to control non-targeted GCase protein K in Example 1. (D) Enzymatic activity, under lysosomal conditions, of α-Gal fusion protein G in Example 1 compared to control non-targeted α-Gal protein H in Example 1.

Figure 7:
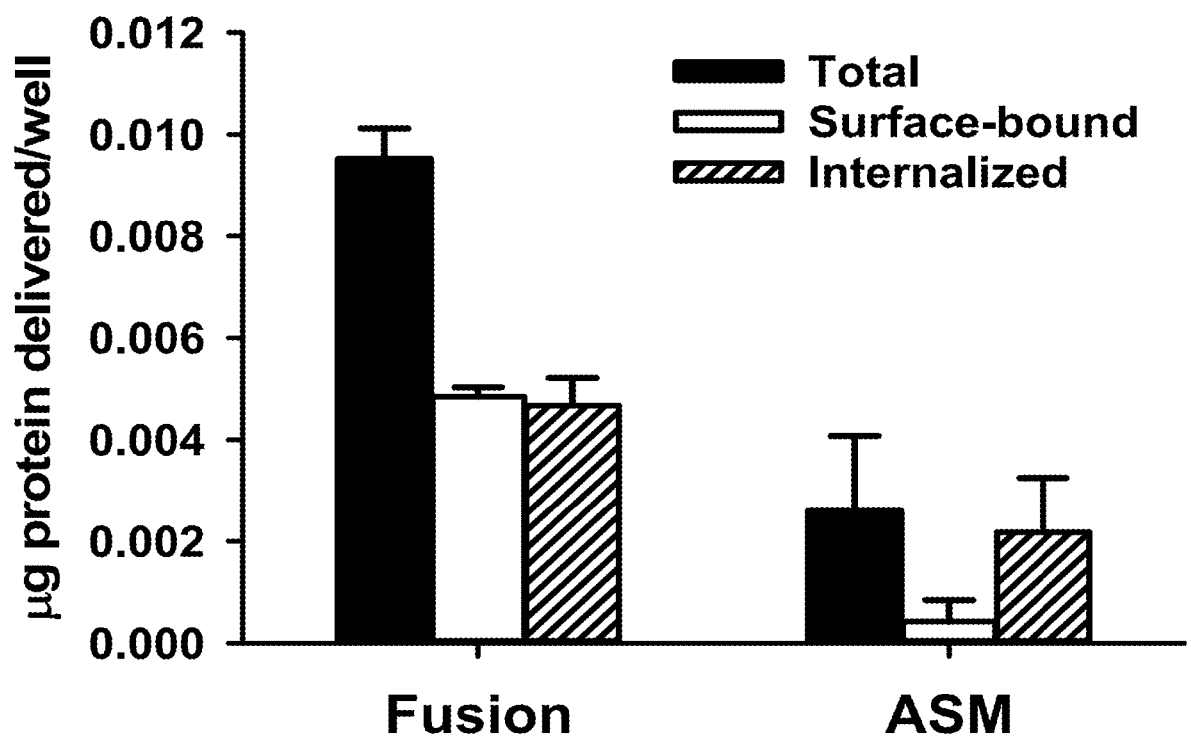

Example 7, illustrated by FIG. 7. Cell binding and internalization of ICAM-1-targeted fusion enzymes. A pharmacological model of Niemann-Pick disease types A and B was used, which consists of treating cells with imipramine, a small molecule known to degrade endogenous ASM. Cells were additionally treated with TNFα to mimic an inflammatory status, as it pertains to Niemann-Pick disease. Cells were then incubated for 3 hours at 37° C. with either fusion protein B in Example 1 (after enterokinase cleavage), or full recombinant ASM produced by He et al. (He, Miranda et al. 1999), which served as basis for Genzyme Olipudase®. In both cases, proteins were labeled with $^{125}$Iodine to allow tracing of their association with cells. Surface-bound fraction was eluted with a glycine solution and the remaining, non-eluted fraction corresponds to internalized protein. The sum of both fractions represents the total cell association.

Figure 8:
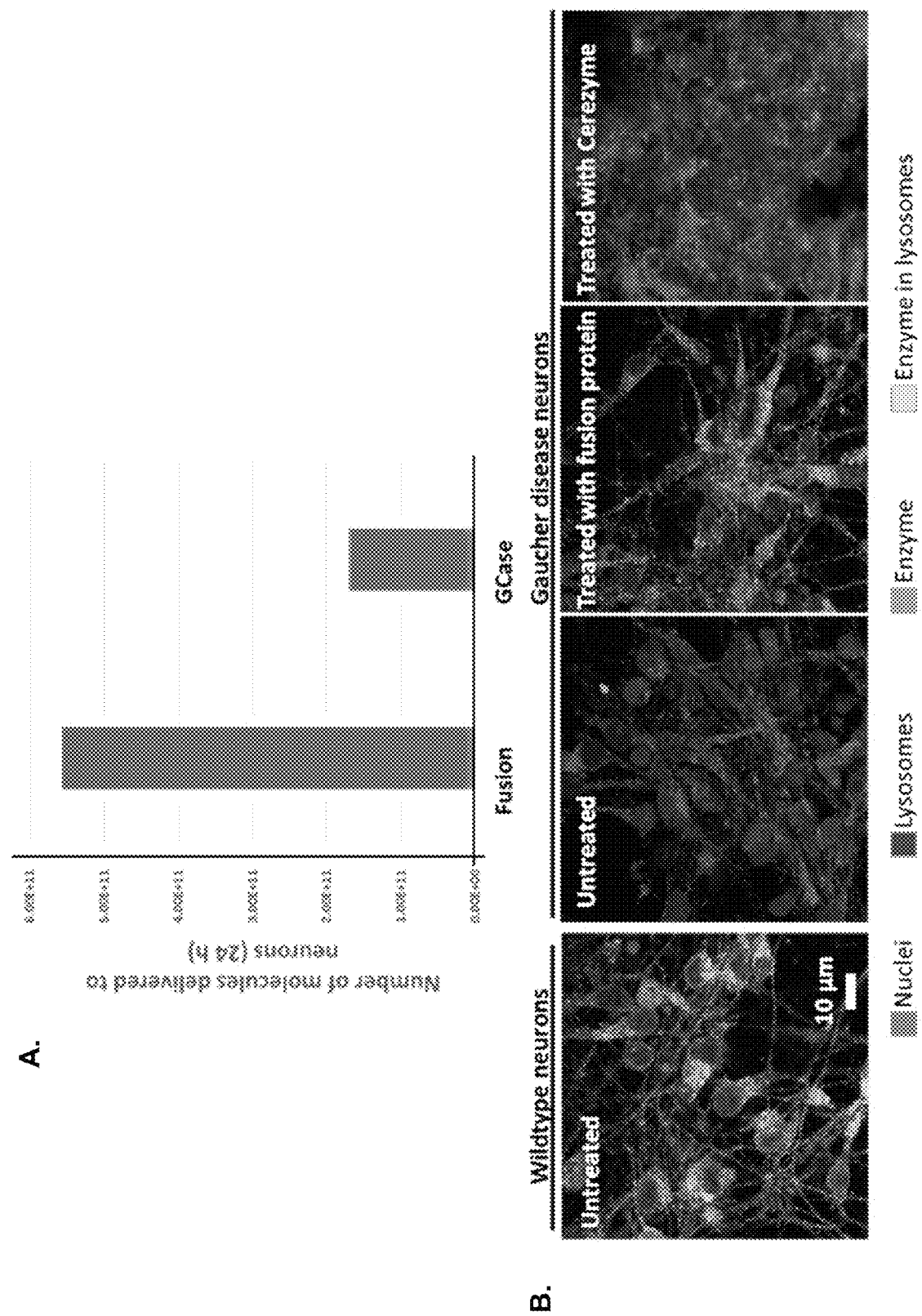

Example 8, Illustrated by FIG. 8. Uptake and lysosomal trafficking of ICAM-1-targeted fusion enzymes by neurons. (A) Induced pluripotent stem cells (iPS)-derived neurons bearing mutations from a Gaucher disease patient and treated with TNFα to mimic an inflammatory status, were incubated for 24 h at 37° C. with either targeted fusion GCase protein J in Example 1 or with control non-targeted GCase protein K in Example 1 (both after enterokinase cleavage). In both cases, these proteins had been pre-labeled with $^{125}$Iodine to trace them. The number of molecules associated to cells was quantified using a gamma counter to measure the radioactive label. (B) iPS-derived neurons bearing the wildtype GCase sequence, or, bearing Gaucher disease mutations and treated with TNFα to mimic an inflammatory status, were fixed, permeabilized and stained using fluorescently-labeled antibodies to detect lysosomes (anti-Lamp1) in red color and GCase enzyme (anti-GCase) in green color. Lysosomal trafficking of these proteins appears in green+red=yellow-orange color. Cell nuclei was stained in blue using DAPI. The same procedure was used for mutant neurons after 24 h treatment with either targeted fusion GCase protein or control non-targeted Cerezyme, a commercial recombinant GCase. Scale bar=10 μm.

Figure 9:
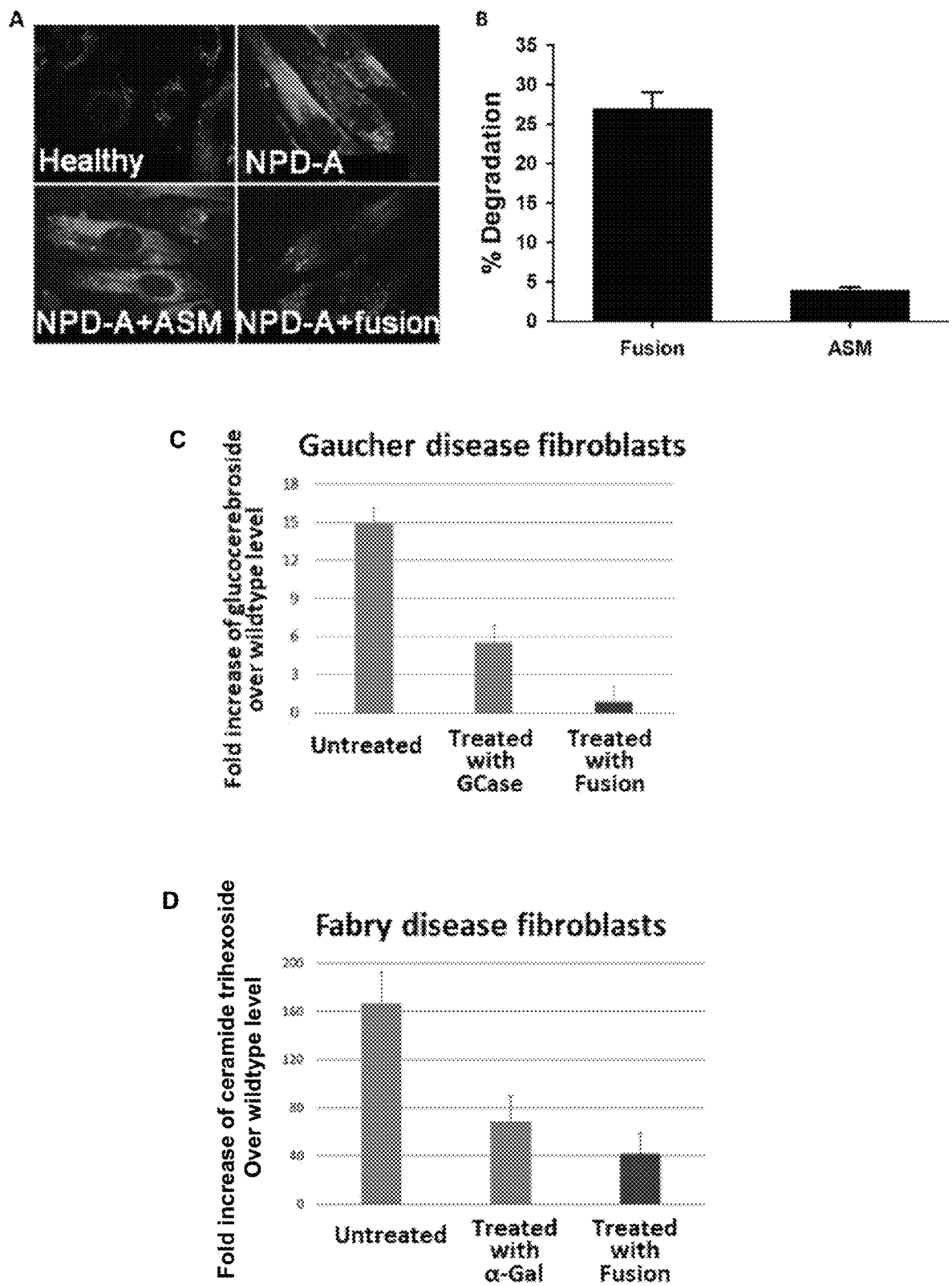

Example 9, illustrated by FIG. 9. Reduction of lysosomal storage in patient cells by ICAM-1-targeted fusion enzymes. (A) Sphingomyelin labeling with BODIPY-FL-C12-sphingomyelin in cultured fibroblasts from healthy versus Niemann-Pick type A patient cells, prior to or after incubation with the same dose (16.7 g/mL) of fusion ASM or non-fusion control. Sphingomyelin aberrantly accumulated in patient cells, since this is the substrate of ASM, which is deficient in these patients. (B) Quantification of the level of BODIPY-FL-C12-sphingomyelin degraded by fusion protein or non-fusion control delivered to patient cells, showing increased therapeutic degradation of the substrate by the fusion protein. (C) Fibroblasts from a Gaucher disease patient were incubated with fluorescent N-hexanoyl-NBD-glucosylceramide to visualize the accumulation of this lipid due to disease, and then left untreated or treated for 5 h with either targeted GCase fusion protein J from Example 1 or control non-targeted GCase protein K from Example 1 (both after enterokinase cleavage). The level of fluorescent N-hexanoyl-NBD-glucosylceramide in wildtype fibroblasts was also visualized and normalized to 1, so that the lipid level in untreated or treated diseased cells was compared to wild-type levels (fold increase). (D) A similar experiment to (C) is shown, yet this time tracing the accumulation of fluorescent N-Dodecanoyl-NBD-ceramide trihexoside in wildtype fibroblasts and fibroblasts from a Fabry disease patient that were either not treated or treated with α-Gal fusion protein G from Example 1 or control non-targeted α-Gal protein H from Example 1 (both after enterokinase cleavage).

Figure 10:
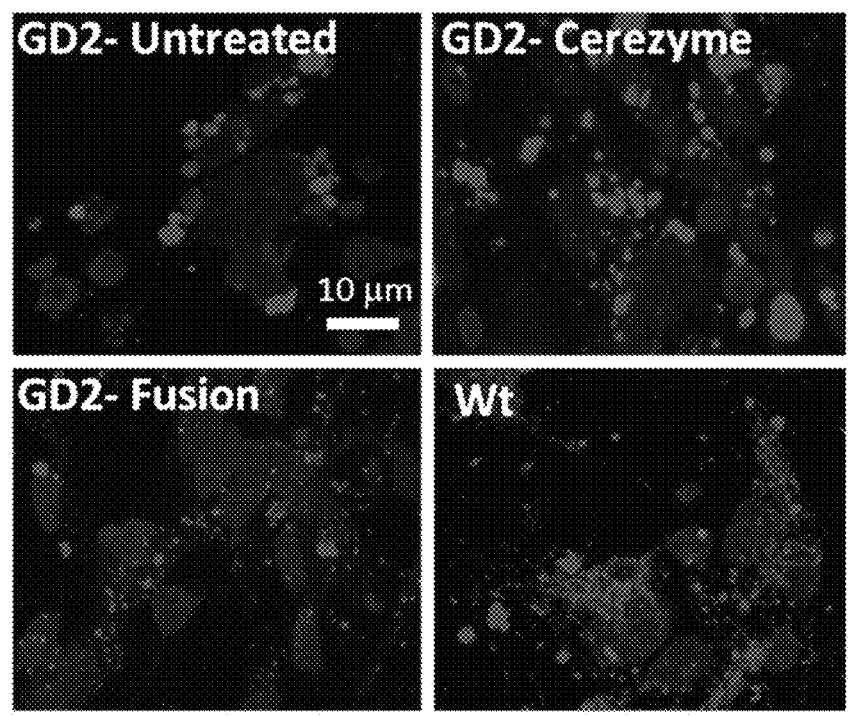
Figure 10:
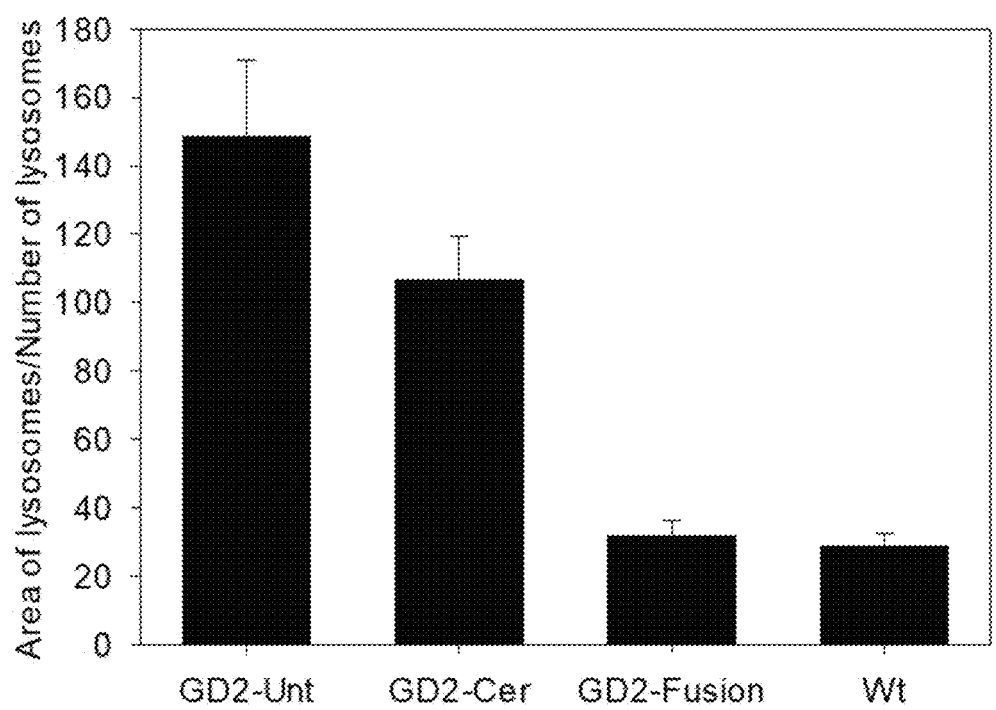

Example 10, illustrated by FIG. 10. Attenuation of the enlargement of lysosomes in diseased neurons by ICAM-1-targeted fusion enzymes. (A) Induced pluripotent stem cells (iPS)-derived neurons bearing wildtype GCase sequence (Wt) or bearing mutations from a Gaucher disease patient (GD2) were treated with TNFα to mimic an inflammatory status. Then, cells were left untreated (GD2-Unt) or were incubated for 24 h at 37° C. with ether targeted fusion GCase protein J in Example 1 (after enterokinase cleavage) or with commercially available Cerezyme. Lysotracker was used to label lysosomes with red fluorescence and cells were fixed. Microscopy was finally used to image lysosomes and quantify their average size (area they occupy per cell/number of lysosomal vesicles per cell).

Figure 11:
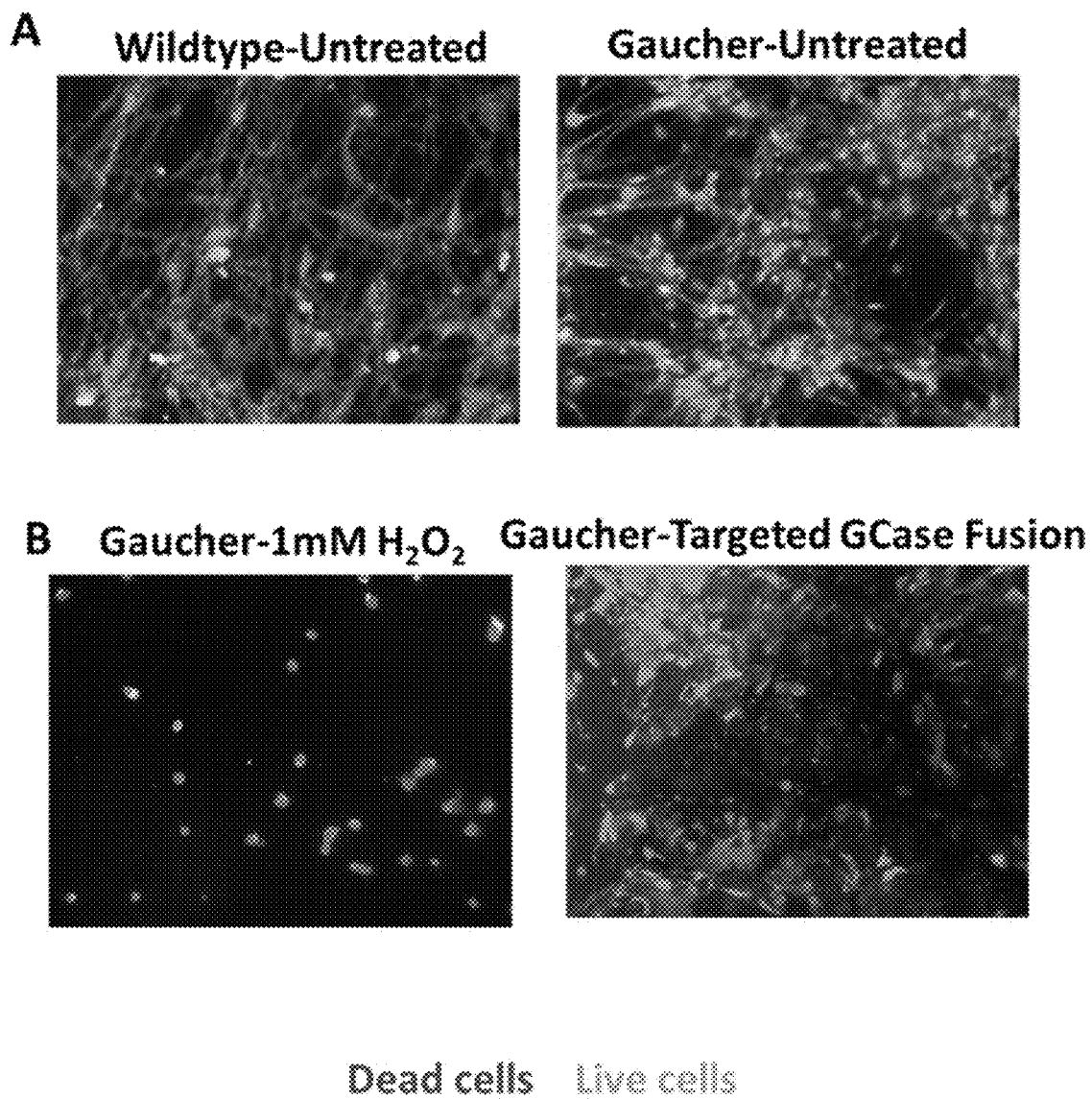

Example 11, illustrated by FIG. 11. Lack of cytotoxicity of ICAM-1-targeted fusion proteins. (A) Induced pluripotent stem cells (iPS)-derived neurons bearing wildtype GCase sequence or bearing Gaucher patient mutations were treated with TNFα overnight to mimic an inflammatory status. The number of live cells or dead cells were visualized using a live/dead viability assay where calcein stains the cytoplasm of live cells green while ethidium homodimer stains dead cell nuclei red, respectively. (B) Similarly, neurons bearing Gaucher patient mutations were incubated with 1 mM $H_2O_2$ for 1 h to induce cell death as a control or for 48 h with targeted GCase fusion protein J in example 1 (after enterokinase cleavage), then the same live/dead assay was used.

Figure 12:
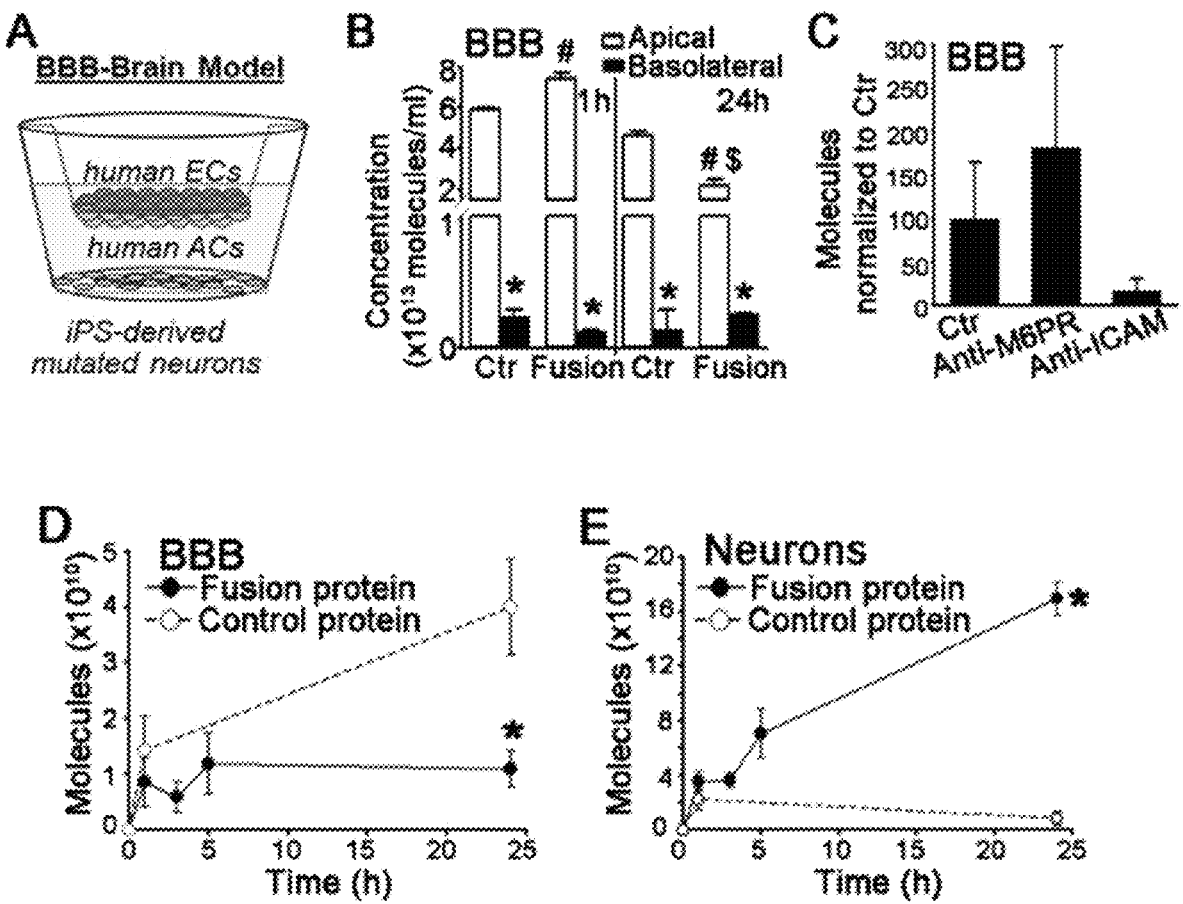

Example 12, illustrated by FIG. 12. Transcytosis of ICAM-1-targeted fusion enzymes across models of the blood-brain barrier and uptake by subjacent neurons. (A) Transwell model of the blood-brain barrier formed by human brain endothelial cells growing on the apical side of a porous filter, astrocytes growing on the basolateral side of the same filter, and these two cellular monolayers separating an apical chamber (mimicking the blood vessel side) from a basolateral chamber (mimicking the brain tissue side). These cells were treated with conduritol-β-epoxide to mimic a Gaucher disease phenotype. Induced pluripotent stem cells (iPS)-derived neurons bearing mutations from a Gaucher disease patient were grown on the bottom of the basolateral chamber. Cells were additionally treated with TNFα to mimic an inflammatory status typical of this disease. (B) ICAM-1 targeted fusion GCase protein J (example 1; after enterokinase cleavage) or control (Ctr) non-targeted GCase protein K (example 1; after enterokinase cleavage) were pre-labeled with $^{125}$Iodine for tracing purposes and added to the apical chamber above the BBB for 1 h or 24 h. After this time, the amount of proteins in the apical or in the basolateral chambers was quantified. The graph shows the concentration of protein molecules left in either chamber, demonstrating the lack of free diffusion or leakage across this BBB model, which can thus be considered a good barrier model. (C) The amount of targeted fusion GCase that interacted with the BBB was quantified after 3 h and compared to the amount of targeted fusion GCase interacting the BBB when cells had been pre-incubated with anti-mannose-6-phosphate receptor or anti-ICAM receptor to block the respective receptor. (D) Presence of fusion GCase protein or control GCase in the BBB or (E) basolateral iPS-neurons over time. Data are average±SEM, * $p<0.05$ (Student's t-test).

Figure 13:
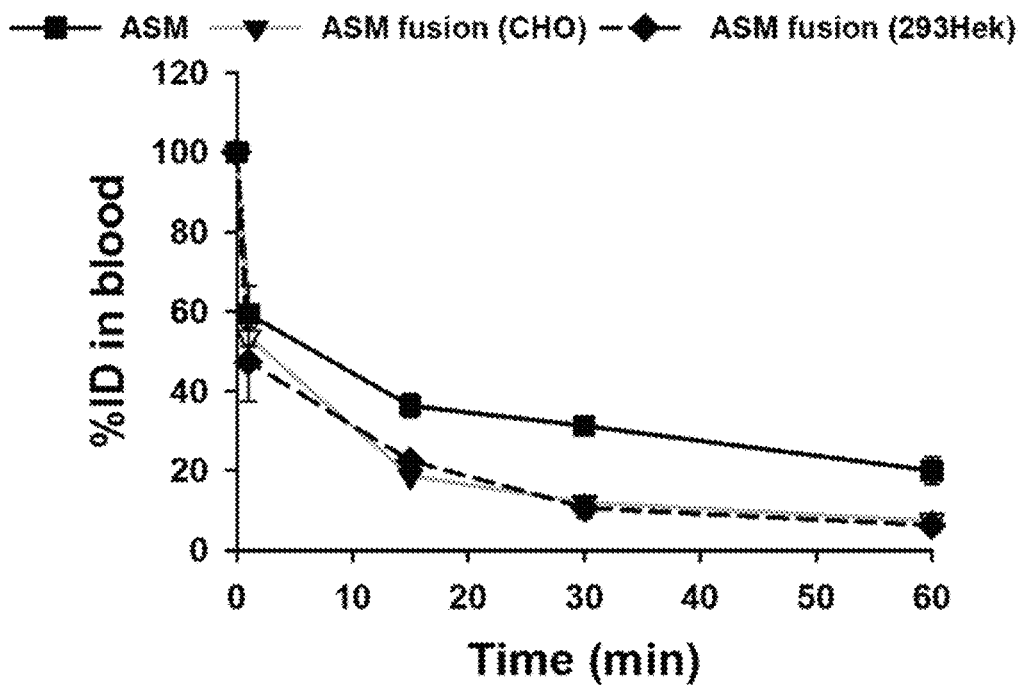
Figure 13:
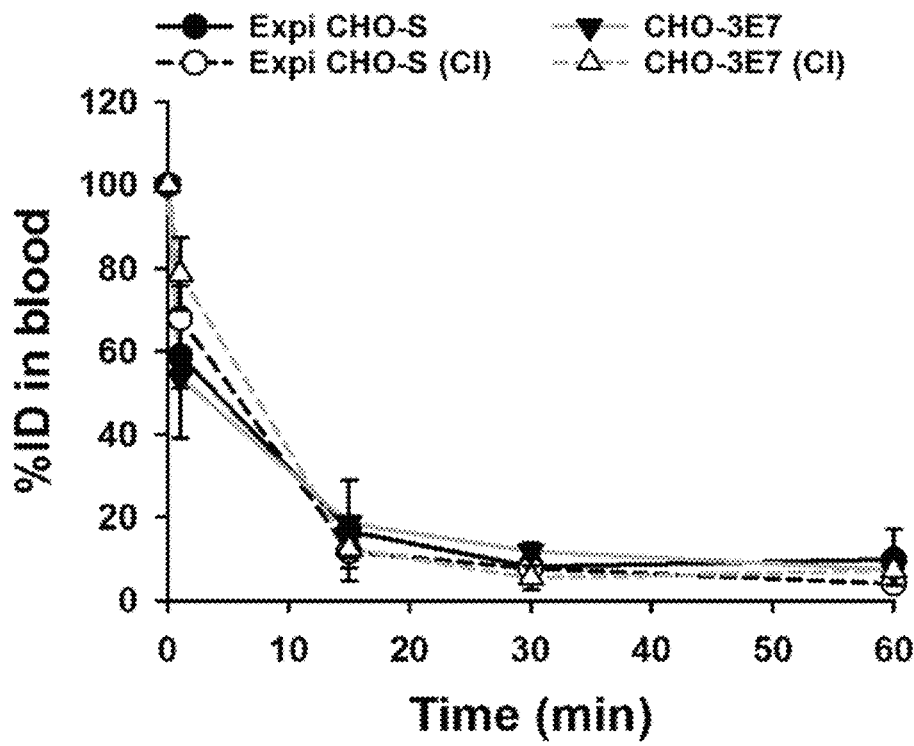

Example 13, illustrated by FIG. 13. Circulation of ICAM-1-targeted fusion enzymes in mice. Blood levels of proteins labeled with $^{125}$Iodine, expressed as a percentage of the injected dose (0.13 mg/Kg), determined at the indicated times after their intravenous injection in ASM knockout mice, the model for Niemann-Pick disease type A and B. (A) Fusion protein B in Example 1, produced from two different cell sources (CHO-3E7 versus Hek 293 cells) is compared to full recombinant ASM produced by He et al. (He, Miranda et al. 1999), which served as basis for Genzyme's Olipudase®. Faster disappearance of fusion proteins is expected due to targeting to tissues, and should be beneficial in lowering systemic side effects and resistance due to immunorecognition. (B) Circulation of the same fusion in two different CHO cell lines, before and after cleavage (Cl) of the His-tag domain by enterokinase.

Figure 14:
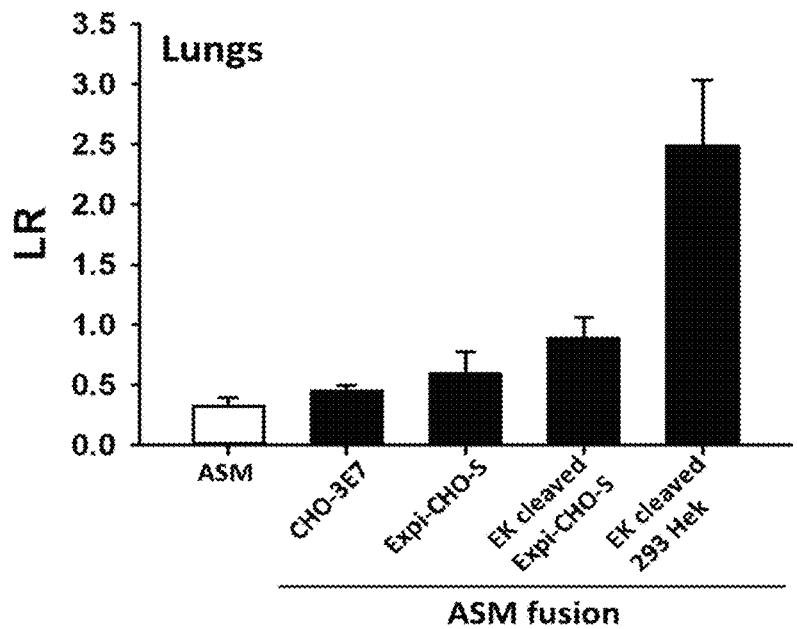
Figure 14:
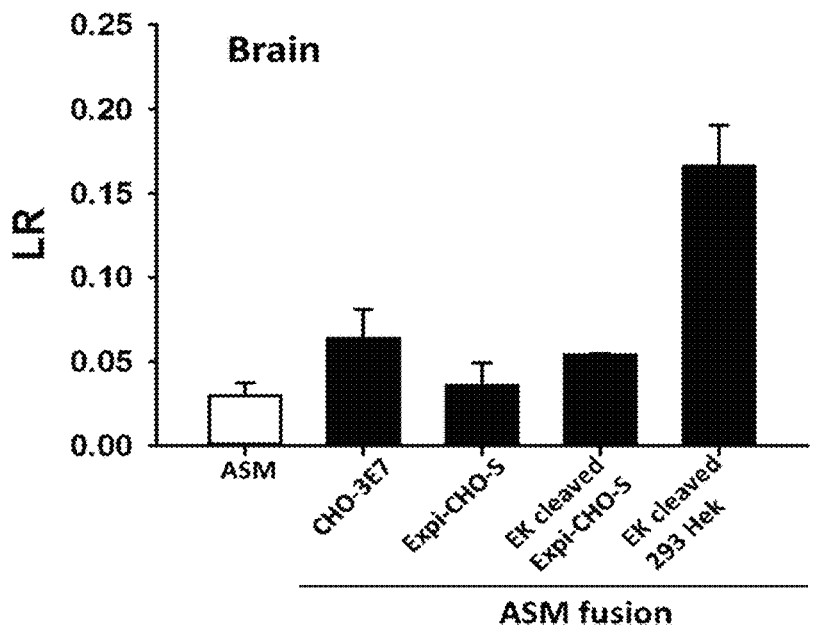

Example 14, illustrated by FIG. 14. Lung and brain distribution of ICAM-1-targeted fusion enzymes in mice.

(A) Lung and (B) brain levels of proteins labeled with $^{125}$Iodine, expressed as the localization ratio (LR), 60 minutes after intravenous injection of 0.13 mg/Kg in mice (lung and brain are main targets for Niemann-Pick disease type B and A, respectively). Fusion protein B in Example 1, produced from three cell sources (CHO-3E7, Expi-CHO-S versus Hek 293 cells), prior or after cleavage with enterokinase (EK) to remove His-tag, is compared to full recombinant ASM produced by He et al. (He, Miranda et al. 1999), which served as basis for Genzyme's Olipudase®. Enhanced targeting is shown for all fusion protein.

Figure 15:
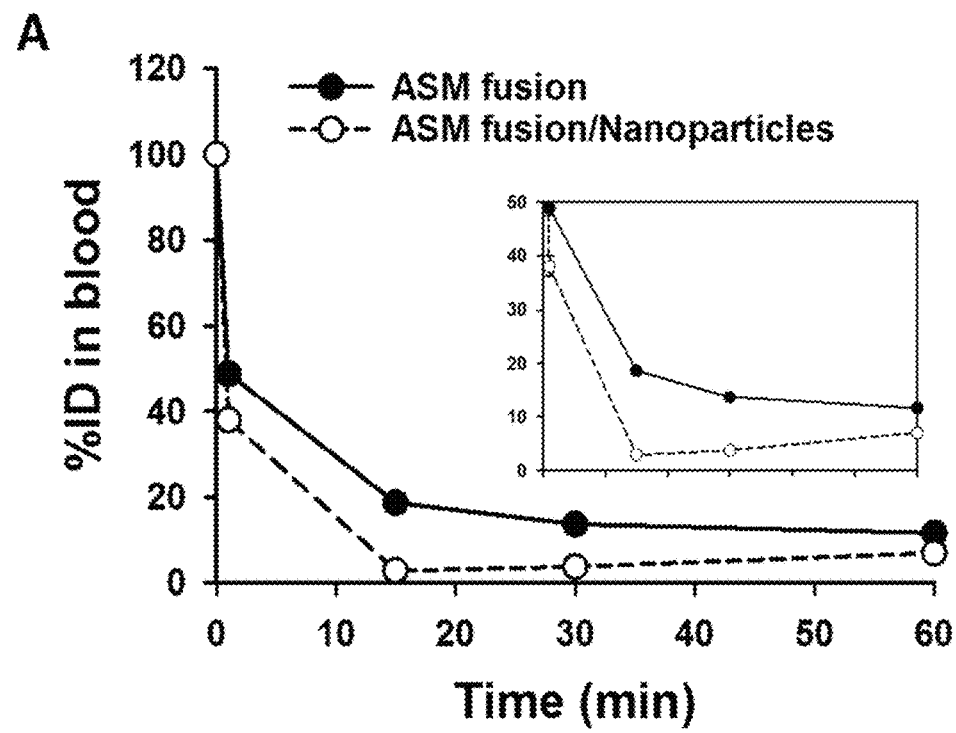
Figure 15:
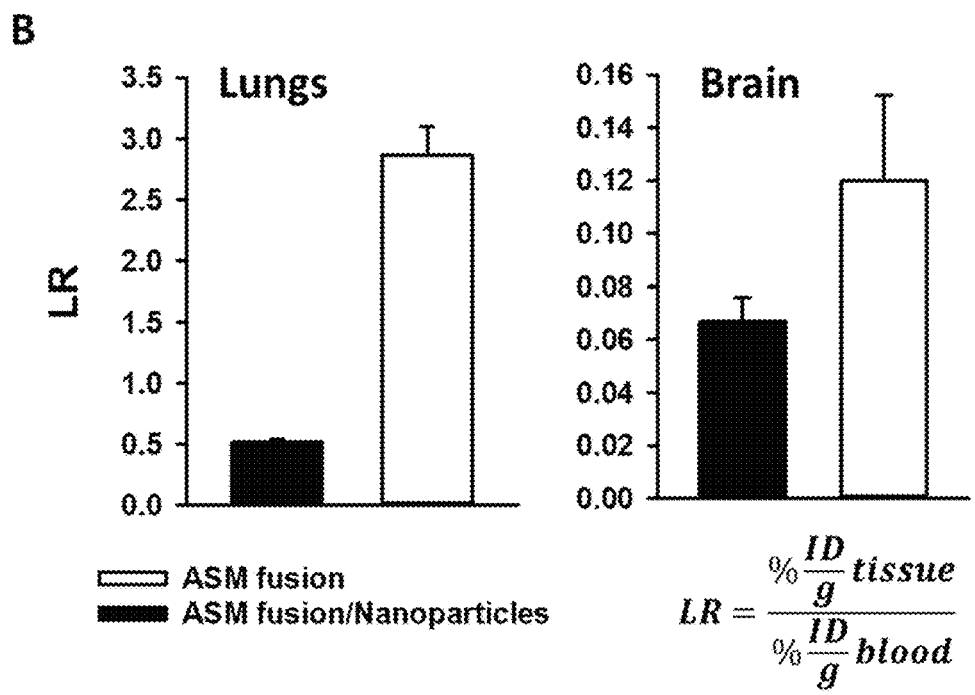
Figure 16:
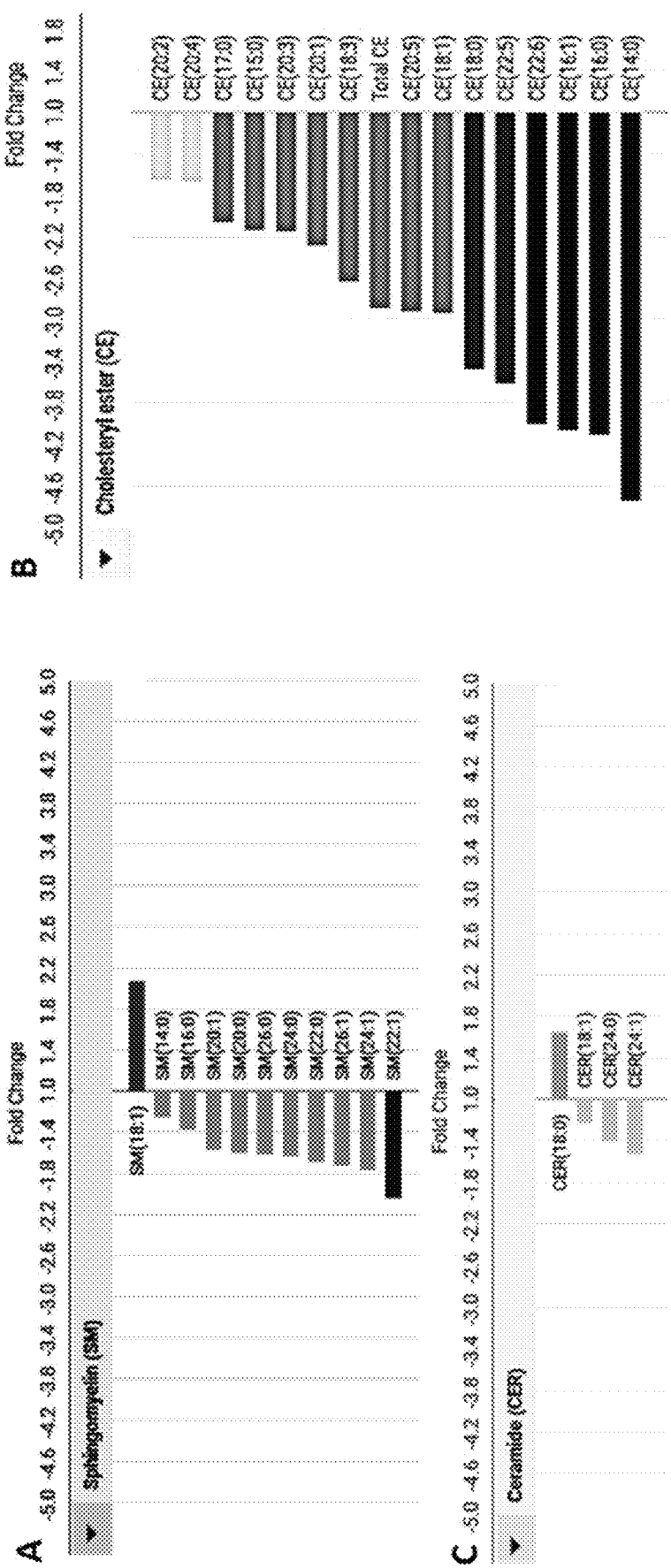
Figure 17:
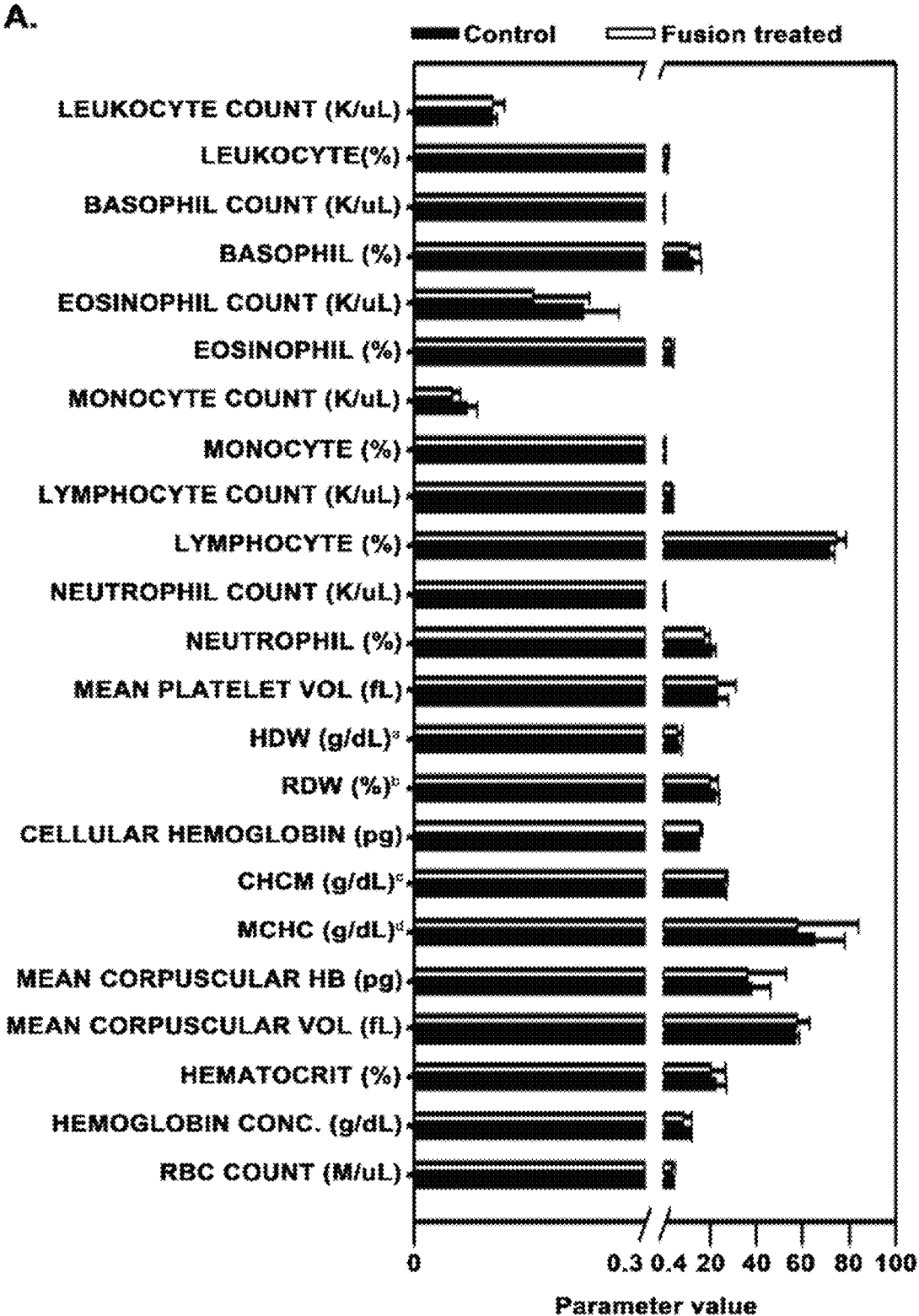
Figure 17:
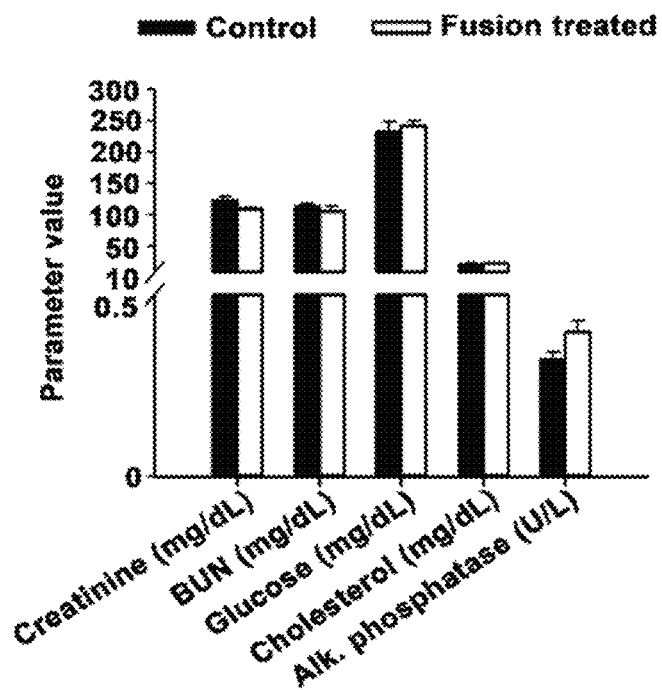
Figure 17:
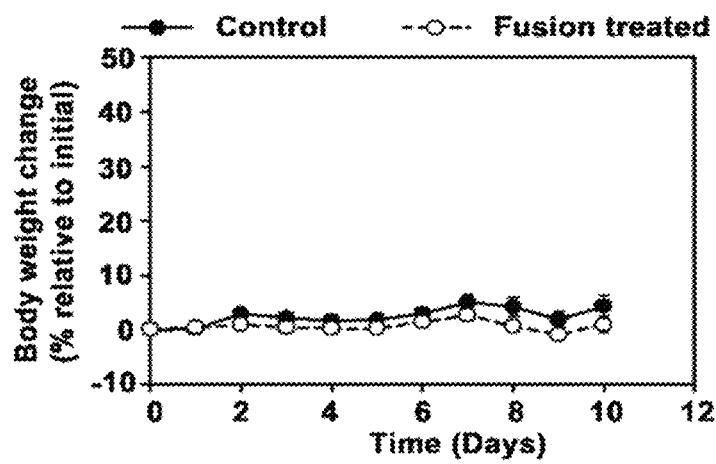

Example 15, illustrated by FIG. 15. Lung and brain distribution of ICAM-1-targeted fusion enzymes administered in mice as nanoparticle formulations. (A) Blood levels of a "naked" fusion protein compared to a fusion protein loaded in a nanoparticle formulation, determined at the indicated times after their intravenous injection and expressed as a percentage of the injected dose (% ID) in blood. The nanoparticle formulation had faster disappearance (the inset shows a close up of the large graph for additional detail), which is expected due to the increase targeting to tissues (see B) and should be beneficial in lowering any potential systemic side effects of the fusion protein. and resistance due to immunorecognition. (B) Lung and brain levels of "naked" versus nanoparticle-loaded fusion protein, expressed as the localization ratio (LR) found 60 min after injection (lung and brain are main targets for Niemann-Pick disease type B and A, respectively). The nanoparticle formulation showed 5-6 fold enhanced lung accumulation and 2-fold enhanced brain accumulation.

Example 16, illustrated by FIG. 16. Brain effects of ICAM-1-targeted fusion enzymes in mice. ASM knockout mice were injected with 0.6 mg/Kg of enterokinasc cleaved fusion protein B in Example 1 every two days, for a total of 6 injections, and were compared to mice injected with vehicle buffer but no fusion protein (sham control). At the end of the experiment, (A) sphingomyelin (SM), the substrate of the ASM enzyme, which aberrantly accumulates in the brain of diseased mice (as in humans) was measured. (B) Cholesterol (CE), which associates to sphingomyelin and also accumulates in the disease, was also measured. (C) Ceramide (CER), the product of the ASM catalytic reaction, which accumulates and causes side effects by Olipudase®, was determined. In all cases, increases of SM, CE, or CER are marked as a positive fold change (bar on the right of the middle line), while decreases are marked as a negative fold change (bars on the left of the middle line). Middle lines are non-treated diseased controls. Both SM and CE were significantly lowered, without dangerous.

Example 17, illustrated by FIG. 17. Side effects of ICAM-1-targeted fusion enzymes in mice. The same animals shown in example 16 were examined for side effects, including: (A) hematology parameters, (B) markers of liver and kidney toxicity, (C) body weight, and (D) behavior. In terms of all the parameters tested, treatment with the fusion protein did not induce toxicity compared to the sham treated group (control). It will be recognized from the foregoing description and figures that the strategy described herein provides improved results in peripheral organs, which are the main target for type B NPD and many other LSDs. This is expected to help lower the dose required for therapeutic activity in these organs with concomitant decrease in cost and side effects, which benefits both drug manufacturers and patients, and can be extended from NPD to all current lysosomal ERTs used for peripheral organ treatment. In addition, the present fusion protein strategy exhibits enhanced targeting and measurable functional effects in the brain, a non-peripheral organ of the central nervous system where no current lysosomal ERT can reach. Thus, this strategy represents a breakthough in the treatment of type A NPD and is applicable to ≈40 additional LSDs with neurological syndromes. Lastly, unlike previous nanoparticulate formulations, which involved polymeric materials that have never been approved for chronic use in pediatric patients, the fusion protein platform described herein can be produced by classical biotechnological means, as done for current ERTs approved by FDA. Reproducibility, high yield and purity, and versatility of production in different cells supports manufacturing and reduces regulatory hurdles for implementing embodiments of the disclosure.

The following sequences are representative and non-limiting examples of embodiments of the disclosure, and relate to the constructs depicted in FIG. 1, and to the results described herein.

Sequence 1. Amino Acid Sequence of the ICAM-1 Targeting Segment, 2γ3.

(SEQ ID NO: 1)

NNQKIVNIKEKVAQIEA

Sequence 2. cDNA sequence of the expression cassette for human acid sphingomyelinase (ASM) with one copy of the 2γ3 ICAM-1-targeting peptide at the amino terminus (SEQ ID NO: 2)

ATGGAGACCGACACACTGCTCCTGTGGGTCCTGCTCCTCTGGGTGCCAGG

AAGTACAGGAGATCACCATCACCATCACCACGACGACGACGACAAGAATA

ACCAAAAGATTGTGAATATCAAAGAGAAAGTGGCTCAGATTGAGGCTGGA

GGCGGAGGAAGCGGCGGCGGAGGAAGCGGATTTCTGGGACACCCTCTTTC

TCCCCAAGGCCATCCTGCCAGGTTACATCGCATAGTGCCCCGGCTCCGAG

ATGTCTTTGGGTGGGGGAACCTCACCTGCCCAATCTGCAAAGGTCTATTC

ACCGCCATCAACCTCGGGCTGAAGAAGGAACCCAATGTGGCTCGCGTGGG

CTCCGTGGCCATCAAGCTGTGCAATCTGCTGAAGATAGCACCACCTGCCG

TGTGCCAATCCATTGTCCACCTCTTTGAGGATGACATGGTGGAGGTGTGG

AGACGCTCAGTGCTGAGCCCATCTGAGGCCTGTGGCCTGCTCCTGGGCTC

CACCTGTGGGCACTGGGACATTTTCTCATCTTGGAACATCTCTTTGCCTA

CTGTGCCGAAGCCGCCCCCCAAACCCCCTAGCCCCCCAGCCCCAGGTGCC

CCTGTCAGCCGCATCCTCTTCCTCACTGACCTGCACTGGGATCATGACTA

CCTGGAGGGCACGGACCCTGACTGTGCAGACCCACTGTGCTGCCGCCGGG

GTTCTGGCCTGCCGCCCGCATCCCGGCCAGGTGCCGGATACTGGGGCGAA

TACAGCAAGTGTGACCTGCCCCTGAGGACCCTGGAGAGCCTGTTGAGTGG

GCTGGGCCCAGCCGGCCCTTTTGATATGGTGTACTGGACAGGAGACATCC

CCGCACATGATGTCTGGCACCAGACTCGTCAGGACCAACTGCGGGCCCTG

ACCACCGTCACAGCACTTGTGAGGAAGTTCCTGGGGCCAGTGCCAGTGTA

CCCTGCTGTGGGTAACCATGAAAGCACACCTGTCAATAGCTTCCCTCCCC

CCTTCATTGAGGGCAACCACTCCTCCCGCTGGCTCTATGAAGCGATGGCC

AAGGCTTGGGAGCCCTGGCTGCCTGCCGAAGCCCTGCGCACCCTCAGAAT

TGGGGGGTTCTATGCTCTTTCCCCATACCCCGGTCTCCGCCTCATCTCTC

TCAATATGAATTTTTGTTCCCGTGAGAACTTCTGGCTCTTGATCAACTCC

ACGGATCCCGCAGGACAGCTCCAGTGGCTGGTGGGGAGCTTCAGGCTGC

TGAGGATCGAGGAGACAAAGTGCATATAATTGGCCACATTCCCCCAGGGC

ACTGTCTGAAGAGCTGGAGCTGGAATTATTACCGAATTGTAGCCAGGTAT

GAGAACACCCTGGCTGCTCAGTTCTTTGGCCACACTCATGTGGATGAATT

TGAGGTCTTCTATGATGAAGAGACTCTGAGCCGGCCGCTGGCTGTAGCCT

TCCTGGCACCCAGTGCAACTACCTACATCGGCCTTAATCCTGGTTACCGT

GTGTACCAAATAGATGGAAACTACTCCGGGAGCTCTCACGTGGTCCTGGA

CCATGAGACCTACATCCTGAATCTGACCCAGGCAAACATACCGGGAGCCA

TACCGCACTGGCAGCTTCTCTACAGGGCTCGAGAAACCTATGGGCTGCCC

AACACACTGCCTACCGCCTGGCACAACCTGGTATATCGCATGCGGGCGA

CATGCAACTTTTCCAGACCTTCTGGTTTCTCTACCATAAGGGCCACCCAC

CCTCGGAGCCCTGTGGCACGCCCTGCCGTCTGGCTACTCTTTGTGCCCAG

CTCTCTGCCCGTGCTGACAGCCCTGCTCTGTGCCGCCACCTGATGCCAGA

TGGGAGCCTCCCAGAGGCCCAGAGCCTGTGGCCAAGGCCACTGTTTTGC

TAG

Sequence 3. cDNA sequence of the expression cassette for human ASM with five tandem-repeats of the 2γ3 ICAM-1-targeting peptide at the amino terminus.

(SEQ ID NO: 3)
ATGGAGACCGACACACTGCTCCTGTGGGTCCTGCTCCTCTGGGTGCCAGG

AAGTACAGGAGATCACCATCACCATCACCACGACGACGACGACAAGAATA

ACCAAAAGATTGTGAATATCAAAGAGAAAGTGGCTCAGATTGAGGCTGGA

GGCGGAGGAAGCGGCGGCGGAGGAAGCAATAATCAGAAAATCGTCAACAT

TAAGGAAAAGGTCGCCCAGATTGAAGCAGGAGGCGGCGGCAGCGGCGGAG

GCGGAAGCAATAATCAGAAGATTGTTAACATCAAAGAAAAGGTGGCCCAA

ATTGAAGCAGGAGGAGGAGGATCTGGAGGCGGAGGCAGCAATAACCAGAA

GATCGTCAACATCAAGGAAAAGGTGGCTCAGATCGAGGCAGGAGGCGGAG

GAAGCGGAGGGGCGGCTCTAACAACCAGAAAATCGTGAACATCAAAGAG

AAAGTGGCTCAGATCGAAGCCGGCGGAGGAGGATCCGGAGGAGGAGGAAG

CGGATTTCTGGGACACCCTCTTTCTCCCCAAGGCCATCCTGCCAGGTTAC

ATCGCATAGTGCCCCGGCTCCGAGATGTCTTTGGTGGGGAACCTCACC

TGCCCAATCTGCAAAGGTCTATTCACCGCCATCAACCTCGGGCTGAAGAA

GGAACCCAATGTGGCTCGCGTGGGCTCCGTGGCCATCAAGCTGTGCAATC

TGCTGAAGATAGCACCACCTGCCGTGTGCCAATCCATTGTCCACCTCTTT

GAGGATGACATGGTGGAGGTGTGGAGACGCTCAGTGCTGAGCCCATCTGA

GGCCTGTGGCCTGCTCCTGGGCTCCACCTGTGGGCACTGGGACATTTTCT

CATCTTGGAACATCTCTTTGCCTACTGTGCCGAAGCCGCCCCCCAAACCC

CCTAGCCCCCAGCCCCAGGTGCCCCTGTCAGCCGCATCCTCTTCCTCAC

TGACCTGCACTGGGATCATGACTACCTGGAGGGCACGGACCCTGACTGTG

CAGACCCACTGTGCTGCCGCCGGGGTTCTGGCCTGCCGCCCGCATCCCGG

CCAGGTGCCGGATACTGGGGCGAATACAGCAAGTGTGACCTGCCCCTGAG

GACCCTGGAGAGCCTGTTGAGTGGGCTGGGCCCAGCCGGCCCTTTTGATA

TGGTGTACTGGACAGGAGACATCCCCGCACATGATGTCTGGCACCAGACT

CGTCAGGACCAACTGCGGGCCCTGACCACCGTCACAGCACTTGTGAGGAA

GTTCCTGGGGCCAGTGCCAGTGTACCCTGCTGTGGGTAACCATGAAAGCA

CACCTGTCAATAGCTTCCCTCCCCCCTTCATTGAGGGCAACCACTCCTCC

CGCTGGCTCTATGAAGCGATGGCCAAGGCTTGGGAGCCCTGGCTGCCTGC

CGAAGCCCTGCGCACCCTCAGAATTGGGGGGTTCTATGCTCTTTCCCCAT

ACCCCGGTCTCCGCCTCATCTCTCTCAATATGAATTTTTGTTCCCGTGAG

AACTTCTGGCTCTTGATCAACTCCACGGATCCCGCAGGACAGCTCCAGTG

GCTGGTGGGGAGCTTCAGGCTGCTGAGGATCGAGGAGACAAAGTGCATA

TAATTGGCCACATTCCCCCAGGGCACTGTCTGAAGAGCTGGAGCTGGAAT

TATTACCGAATTGTAGCCAGGTATGAGAACACCCTGGCTGCTCAGTTCTT

TGGCCACACTCATGTGGATGAATTTGAGGTCTTCTATGATGAAGAGACTC

TGAGCCGGCCGCTGGCTGTAGCCTTCCTGGCACCCAGTGCAACTACCTAC

ATCGGCCTTAATCCTGGTTACCGTGTGTACCAAATAGATGGAAACTACTC

CGGGAGCTCTCACGTGGTCCTGGACCATGAGACCTACATCCTGAATCTGA

CCCAGGCAAACATACCGGGAGCCATACCGCACTGGCAGCTTCTCTACAGG

GCTCGAGAAACCTATGGGCTGCCCAACACACTGCCTACCGCCTGGCACAA

CCTGGTATATCGCATGCGGGGCGACATGCAACTTTTCCAGACCTTCTGGT

TTCTCTACCATAAGGGCCACCCACCCTCGGAGCCCTGTGGCACGCCCTGC

CGTCTGGCTACTCTTTGTGCCCAGCTCTCTGCCCGTGCTGACAGCCCTGC

TCTGTGCCGCCACCTGATGCCAGATGGGAGCCTCCCAGAGGCCCAGAGCC

TGTGGCCAAGGCCACTGTTTTGCTAG

Sequence 4. cDNA sequence of the expression cassette for human ASM with ten tandem-repeats of the 2γ3 ICAM-1-targeting peptide at the amino terminus.

(SEQ ID NO: 4)
ATGGAGACCGACACACTGCTCCTGTGGGTCCTGCTCCTCTGGGTGCCAGG

AAGTACAGGAGATCACCATCACCATCACCACGACGACGACGACAAGAATA

ACCAAAAGATTGTGAATATCAAAGAGAAAGTGGCTCAGATTGAGGCTGGA

GGCGGAGGAAGCGGCGGCGGAGGAAGCAATAATCAGAAAATCGTCAACAT

TAAGGAAAAGGTCGCCCAGATTGAAGCAGGAGGCGGCGGCAGCGGCGGAG

GCGGAAGCAATAATCAGAAGATTGTTAACATCAAAGAAAAGGTGGCCCAA

ATTGAAGCAGGAGGAGGAGGATCTGGAGGCGGAGGCAGCAATAACCAGAA

GATCGTCAACATCAAGGAAAAGGTGGCTCAGATCGAGGCAGGAGGCGGAG

GAAGCGGAGGGGCGGCTCTAACAACCAGAAAATCGTGAACATCAAAGAG

AAAGTGGCTCAGATCGAAGCCGGCGGAGGAGGATCCGGAGGAGGAGGAAG

CAATAACCAAAAGATTGTGAATATCAAAGAGAAAGTGGCTCAGATTGAGG

CTGGAGGCGGAGGAAGCGGCGGCGGAGGAAGCAATAATCAGAAAATCGTC

-continued

AACATTAAGGAAAAGGTCGCCCAGATTGAAGCAGGAGGCGGCGGCAGCGG
CGGAGGCGGAAGCAATAATCAGAAGATTGTTAACATCAAAGAAAAGGTGG
CCCAAATTGAAGCAGGAGGAGGAGGATCTGGAGGCGGAGGCAGCAATAAC
CAGAAGATCGTCAACATCAAGGAAAAGGTGGCTCAGATCGAGGCAGGAGG
CGGAGGAAGCGGAGGGGGCGGCTCTAACAACCAGAAAATCGTGAACATCA
AAGAGAAAGTGGCTCAGATCGAAGCCGGCGGAGGAGGATCCGGAGGAGGA
GGAAGCGGATTTCTGGGACACCCTCTTTCTCCCCAAGGCCATCCTGCCAG
GTTACATCGCATAGTGCCCCGGCTCCGAGATGTCTTTGGGTGGGGGAACC
TCACCTGCCCAATCTGCAAAGGTCTATTCACCGCCATCAACCTCGGGCTG
AAGAAGGAACCCAATGTGGCTCGCGTGGGCTCCGTGGCCATCAAGCTGTG
CAATCTGCTGAAGATAGCACCACCTGCCGTGTGCCAATCCATTGTCCACC
TCTTTGAGGATGACATGGTGGAGGTGTGGAGACGCTCAGTGCTGAGCCCA
TCTGAGGCCTGTGGCCTGCTCCTGGGCTCCACCTGTGGGCACTGGGACAT
TTTCTCATCTTGGAACATCTCTTTGCCTACTGTGCCGAAGCCGCCCCCCA

AACCCCCTAGCCCCCCAGCCCCAGGTGCCCCTGTCAGCCGCATCCTCTTC

CTCACTGACCTGCACTGGGATCATGACTACCTGGAGGGCACGGACCCTGA

CTGTGCAGACCCACTGTGCTGCCGCCGGGGTTCTGGCCTGCCGCCCGCAT

CCCGGCCAGGTGCCGGATACTGGGGCGAATACAGCAAGTGTGACCTGCCC

CTGAGGACCCTGGAGAGCCTGTTGAGTGGGCTGGGCCCAGCCGGCCCTTT

TGATATGGTGTACTGGACAGGAGACATCCCCGCACATGATGTCTGGCACC

AGACTCGTCAGGACCAACTGCGGGCCCTGACCACCGTCACAGCACTTGTG

AGGAAGTTCCTGGGGCCAGTGCCAGTGTACCCTGCTGTGGGTAACCATGA

AAGCACACCTGTCAATAGCTTCCCTCCCCCCTTCATTGAGGGCAACCACT

CCTCCCGCTGGCTCTATGAAGCGATGGCCAAGGCTTGGGAGCCCTGGCTG

CCTGCCGAAGCCCTGCGCACCCTCAGAATTGGGGGGTTCTATGCTCTTTC

CCCATACCCCGGTCTCCGCCTCATCTCTCTCAATATGAATTTTTGTTCCC

GTGAGAACTTCTGGCTCTTGATCAACTCCACGGATCCCGCAGGACAGCTC

CAGTGGCTGGTGGGGGAGCTTCAGGCTGCTGAGGATCGAGGAGACAAAGT

GCATATAATTGGCCACATTCCCCCAGGGCACTGTCTGAAGAGCTGGAGCT

GGAATTATTACCGAATTGTAGCCAGGTATGAGAACACCCTGGCTGCTCAG

TTCTTTGGCCACACTCATGTGGATGAATTTGAGGTCTTCTATGATGAAGA

GACTCTGAGCCGGCCGCTGGCTGTAGCCTTCCTGGCACCCAGTGCAACTA

CCTACATCGGCCTTAATCCTGGTTACCGTGTGTACCAAATAGATGGAAAC

TACTCCGGGAGCTCTCACGTGGTCCTGGACCATGAGACCTACATCCTGAA

TCTGACCCAGGCAAACATACCGGGAGCCATACCGCACTGGCAGCTTCTCT

ACAGGGCTCGAGAAACCTATGGGCTGCCCAACACACTGCCTACCGCCTGG

CACAACCTGGTATATCGCATGCGGGGCGACATGCAACTTTTCCAGACCTT

CTGGTTTCTCTACCATAAGGGCCACCCACCCTCGGAGCCCTGTGGCACGC

-continued

CCTGCCGTCTGGCTACTCTTTGTGCCCAGCTCTCTGCCCGTGCTGACAGC

CCTGCTCTGTGCCGCCACCTGATGCCAGATGGGAGCCTCCCAGAGGCCCA

GAGCCTGTGGCCAAGGCCACTGTTTTGCTAG

Sequence 5. cDNA sequence of the expression cassette for human ASM with five tandem-repeats of the 2γ3 ICAM-1-targeting peptide at the carboxyl terminus.

(SEQ ID NO: 5)

ATGGAGACCGACACACTGCTCCTGTGGGTCCTGCTCCTCTGGGTGCCAGG

AAGTACAGGAGATCACCATCACCATCACCACGACGACGACGACAAGCACC

CTCTTTCTCCCCAAGGCCATCCTGCCAGGTTACATCGCATAGTGCCCCGG

CTCCGAGATGTCTTTGGGTGGGGGAACCTCACCTGCCCAATCTGCAAAGG

TCTATTCACCGCCATCAACCTCGGGCTGAAGAAGGAACCCAATGTGGCTC

GCGTGGGCTCCGTGGCCATCAAGCTGTGCAATCTGCTGAAGATAGCACCA

CCTGCCGTGTGCCAATCCATTGTCCACCTCTTTGAGGATGACATGGTGGA

GGTGTGGAGACGCTCAGTGCTGAGCCCATCTGAGGCCTGTGGCCTGCTCC

TGGGCTCCACCTGTGGGCACTGGGACATTTTCTCATCTTGGAACATCTCT

TTGCCTACTGTGCCGAAGCCGCCCCCCAAACCCCCTAGCCCCCCAGCCCC

AGGTGCCCCTGTCAGCCGCATCCTCTTCCTCACTGACCTGCACTGGGATC

ATGACTACCTGGAGGGCACGGACCCTGACTGTGCAGACCCACTGTGCTGC

CGCCGGGGTTCTGGCCTGCCGCCCGCATCCCGGCCAGGTGCCGGATACTG

GGGCGAATACAGCAAGTGTGACCTGCCCCTGAGGACCCTGGAGAGCCTGT

TGAGTGGGCTGGGCCCAGCCGGCCCTTTTGATATGGTGTACTGGACAGGA

GACATCCCCGCACATGATGTCTGGCACCAGACTCGTCAGGACCAACTGCG

GGCCCTGACCACCGTCACAGCACTTGTGAGGAAGTTCCTGGGGCCAGTGC

CAGTGTACCCTGCTGTGGGTAACCATGAAAGCACACCTGTCAATAGCTTC

CCTCCCCCCTTCATTGAGGGCAACCACTCCTCCCGCTGGCTCTATGAAGC

GATGGCCAAGGCTTGGGAGCCCTGGCTGCCTGCCGAAGCCCTGCGCACCC

TCAGAATTGGGGGGTTCTATGCTCTTTCCCCATACCCCGGTCTCCGCCTC

ATCTCTCTCAATATGAATTTTTGTTCCCGTGAGAACTTCTGGCTCTTGAT

CAACTCCACGGATCCCGCAGGACAGCTCCAGTGGCTGGTGGGGGAGCTTC

AGGCTGCTGAGGATCGAGGAGACAAAGTGCATATAATTGGCCACATTCCC

CCAGGGCACTGTCTGAAGAGCTGGAGCTGGAATTATTACCGAATTGTAGC

CAGGTATGAGAACACCCTGGCTGCTCAGTTCTTTGGCCACACTCATGTGG

ATGAATTTGAGGTCTTCTATGATGAAGAGACTCTGAGCCGGCCGCTGGCT

GTAGCCTTCCTGGCACCCAGTGCAACTACCTACATCGGCCTTAATCCTGG

TTACCGTGTGTACCAAATAGATGGAAACTACTCCGGGAGCTCTCACGTGG

TCCTGGACCATGAGACCTACATCCTGAATCTGACCCAGGCAAACATACCG

GGAGCCATACCGCACTGGCAGCTTCTCTACAGGGCTCGAGAAACCTATGG

GCTGCCCAACACACTGCCTACCGCCTGGCACAACCTGGTATATCGCATGC

GGGGCGACATGCAACTTTTCCAGACCTTCTGGTTTCTCTACCATAAGGGC

CACCCACCCTCGGAGCCCTGTGGCACGCCCTGCCGTCTGGCTACTCTTTG

-continued

TGCCCAGCTCTCTGCCCGTGCTGACAGCCCTGCTCTGTGCCGCCACCTGA

TGCCAGATGGGAGCCTCCCAGAGGCCCAGAGCCTGTGGCCAAGGCCACTG

TTTTGCGGATTTCTGGGAGGCGGAGGAGGATCCGGAGGAGGAGGAAGCAA

TAACCAAAAGATTGTGAATATCAAAGAGAAAGTGGCTCAGATTGAGGCTG

GAGGCGGAGGAAGCGGCGGCGGAGGAAGCAATAATCAGAAAATCGTCAAC

ATTAAGGAAAAGGTCGCCCAGATTGAAGCAGGAGGCGGCGGCAGCGGCGG

AGGCGGAAGCAATAATCAGAAGATTGTTAACATCAAAGAAAAGGTGGCCC

AAATTGAAGCAGGAGGAGGAGGATCTGGAGGCGGAGGCAGCAATAACCAG

AAGATCGTCAACATCAAGGAAAAGGTGGCTCAGATCGAGGCAGGAGGCGG

AGGAAGCGGAGGGGCGGCTCTAACAACCAGAAAATCGTGAACATCAAAG

AGAAAGTGGCTCAGATCGAAGCCTAG

Sequence 6. cDNA sequence of the expression cassette for human ASM control.

(SEQ ID NO: 6)
ATGGAGACCGACACACTGCTCCTGTGGGTCCTGCTCCTCTGGGTGCCAGG

AAGTACAGGAGATCACCATCACCATCACCACGACGACGACGACAAGCACC

CTCTTTCTCCCCAAGGCCATCCTGCCAGGTTACATCGCATAGTGCCCCGG

CTCCGAGATGTCTTTGGGTGGGGAACCTCACCTGCCCAATCTGCAAAGG

TCTATTCACCGCCATCAACCTCGGGCTGAAGAAGGAACCCAATGTGGCTC

GCGTGGGCTCCGTGGCCATCAAGCTGTGCAATCTGCTGAAGATAGCACCA

CCTGCCGTGTGCCAATCCATTGTCCACCTCTTTGAGGATGACATGGTGGA

GGTGTGGAGACGCTCAGTGCTGAGCCCATCTGAGGCCTGTGGCCTGCTCC

TGGGCTCCACCTGTGGGCACTGGGACATTTTCTCATCTTGGAACATCTCT

TTGCCTACTGTGCCGAAGCCGCCCCCCAAACCCCCTAGCCCCCCAGCCCC

AGGTGCCCCTGTCAGCCGCATCCTCTTCCTCACTGACCTGCACTGGGATC

ATGACTACCTGGAGGGCACGGACCCTGACTGTGCAGACCCACTGTGCTGC

CGCCGGGGTTCTGGCCTGCCGCCCGCATCCCGGCCAGGTGCCGGATACTG

GGGCGAATACAGCAAGTGTGACCTGCCCCTGAGGACCCTGGAGAGCCTGT

TGAGTGGGCTGGGCCCAGCCGGCCCTTTTGATATGGTGTACTGGACAGGA

GACATCCCCGCACATGATGTCTGGCACCAGACTCGTCAGGACCAACTGCG

GGCCCTGACCACCGTCACAGCACTTGTGAGGAAGTTCCTGGGGCCAGTGC

CAGTGTACCCTGCTGTGGGTAACCATGAAAGCACACCTGTCAATAGCTTC

CCTCCCCCCTTCATTGAGGGCAACCACTCCTCCCGCTGGCTCTATGAAGC

GATGGCCAAGGCTTGGGAGCCCTGGCTGCCTGCCGAAGCCCTGCGCACCC

TCAGAATTGGGGGGTTCTATGCTCTTTCCCCATACCCCGGTCTCCGCCTC

ATCTCTCTCAATATGAATTTTGTTCCCGTGAGAACTTCTGGCTCTTGAT

CAACTCCACGGATCCCGCAGGACAGCTCCAGTGGCTGGTGGGGAGCTTC

AGGCTGCTGAGGATCGAGGAGACAAAGTGCATATAATTGGCCACATTCCC

CCAGGGCACTGTCTGAAGAGCTGGAGCTGGAATTATTACCGAATTGTAGC

CAGGTATGAGAACACCCTGGCTGCTCAGTTCTTTGGCCACACTCATGTGG

-continued

ATGAATTTGAGGTCTTCTATGATGAAGAGACTCTGAGCCGGCCGCTGGCT

GTAGCCTTCCTGGCACCCAGTGCAACTACCTACATCGGCCTTAATCCTGG

TTACCGTGTGTACCAAATAGATGGAAACTACTCCGGGAGCTCTCACGTGG

TCCTGGACCATGAGACCTACATCCTGAATCTGACCCAGGCAAACATACCG

GGAGCCATACCGCACTGGCAGCTTCTCTACAGGGCTCGAGAAACCTATGG

GCTGCCCAACACACTGCCTACCGCCTGGCACAACCTGGTATATCGCATGC

GGGGCGACATGCAACTTTTCCAGACCTTCTGGTTTCTCTACCATAAGGGC

CACCCACCCTCGGAGCCCTGTGGCACGCCCTGCCGTCTGGCTACTCTTTG

TGCCCAGCTCTCTGCCCGTGCTGACAGCCCTGCTCTGTGCCGCCACCTGA

TGCCAGATGGGAGCCTCCCAGAGGCCCAGAGCCTGTGGCCAAGGCCACTG

TTTTGCTAG

Sequence 7. cDNA sequence of the expression cassette for human alpha galactosidase (αGal) with one copy of the 2γ3 ICAM-1-targeting peptide at the amino terminus.

(SEQ ID NO: 7)
ATGGGCTGGTCCTGCATCATTCTGTTTCTGGTGGCTACCGCCACCGGCGT

GCACTCTGATCACCACCACCATCACCACGACGATGACGACAAGAACAACC

AGAAGATCGTCAACATCAAAGAGAAGGTCGCCCAGATCGAGGCTGGAGGC

GGAGGATCTGGTGGTGGCGGATCTGGATTCCTTGGCCTGGACAACGGCCT

GGCTAGAACCCCTACCATGGGATGGCTGCACTGGGAGAGATTCATGTGCA

ACCTGGACTGCCAAGAGGAACCCGACTCCTGCATCTCCGAGAAGCTGTTC

ATGGAAATGGCCGAGCTGATGGTGTCCGAAGGCTGGAAGGATGCCGGCTA

CGAGTACCTGTGCATCGACGACTGTTGGATGGCCCCTCAGAGAGACTCTG

AGGGCAGACTGCAGGCCGATCCTCAGAGATTTCCCCACGGCATCAGACAG

CTGGCCAACTACGTGCACTCCAAGGGCCTGAAGCTGGGCATCTATGCCGA

CGTGGGCAACAAGACCTGTGCCGGCTTTCCTGGCTCCTTCGGCTACTACG

ATATCGACGCCCAGACCTTCGCTGACTGGGGAGTCGATCTGCTGAAGTTC

GACGGCTGCTACTGCGACTCCCTGGAAAATCTGGCCGACGGCTACAAGCA

CATGTCTCTGGCCCTGAACCGGACCGGCAGATCCATCGTGTATAGCTGCG

AGTGGCCCCTGTACATGTGGCCCTTCCAGAAGCCTAACTACACCGAGATC

AGACAGTACTGCAACCACTGGCGGAACTTCGCCGACATCGACGATAGCTG

GAAGTCCATCAAGTCTATCCTGGACTGGACCTCCTTCAATCAAGAGCGGA

TCGTGGATGTGGCTGGCCCTGGCGGATGGAACGATCCTGATATGCTGGTC

ATCGGCAACTTCGGCCTGTCCTGGAACCAGCAAGTGACCCAGATGGCCCT

GTGGGCCATTATGGCCGCTCCTCTGTTCATGTCCAACGACCTGAGACACA

TCAGCCCTCAGGCCAAGGCTCTGCTGCAGGACAAGGATGTGATCGCTATC

AACCAGGATCCTCTGGGCAAGCAGGGCTACCAGTTGAGACAGGGCGACAA

CTTTGAAGTGTGGGAAAGACCCCTGTCCGGCCTGGCATGGGCTGTCGCCA

TGATCAACAGACAAGAGATCGGCGGACCCCGGTCCTACACAATCGCTGTT

GCTTCTCTCGGCAAAGGCGTGGCCTGCAATCCTGCCTGTTTCATCACACA

GCTGCTGCCCGTGAAGAGAAAGCTGGGCTTTTACGAGTGGACCTCTCGGC

-continued
TGCGGTCCCACATCAATCCTACCGGAACAGTGCTGCTGCAGCTGGAAAAC

ACCATGCAGATGTCCCTGAAGGACCTGCTGTGA

Sequence 8. cDNA sequence of the expression cassette for human αGal with five tandem-repeats of the 2γ3 ICAM-1-targeting peptide at the carboxyl terminus.

(SEQ ID NO: 8)
ATGGGCTGGTCCTGCATCATTCTGTTTCTGGTGGCTACCGCCACCGGCGT

GCACTCTGATCACCACCACCATCACCACGACGATGACGACAAGCTGGACA

ACGGCCTGGCTAGAACCCCTACCATGGGATGGCTGCACTGGGAGAGATTC

ATGTGCAACCTGGACTGCCAAGAGGAACCCGACTCCTGCATCTCCGAGAA

GCTGTTCATGGAAATGGCCGAGCTGATGGTGTCCGAAGGCTGGAAGGATG

CCGGCTACGAGTACCTGTGCATCGACGACTGTTGGATGGCCCCTCAGAGA

GACTCTGAGGGCAGACTGCAGGCCGATCCTCAGAGATTTCCCCACGGCAT

CAGACAGCTGGCCAACTACGTGCACTCCAAGGGCCTGAAGCTGGGCATCT

ATGCCGACGTGGGCAACAAGACCTGTGCCGGCTTTCCTGGCTCCTTCGGC

TACTACGATATCGACGCCCAGACCTTCGCTGACTGGGGAGTCGATCTGCT

GAAGTTCGACGGCTGCTACTGCGACTCCCTGGAAAATCTGGCCGACGGCT

ACAAGCACATGTCTCTGGCCCTGAACCGGACCGGCAGATCCATCGTGTAT

AGCTGCGAGTGGCCCCTGTACATGTGGCCCTTCCAGAAGCCTAACTACAC

CGAGATCAGACAGTACTGCAACCACTGGCGGAACTTCGCCGACATCGACG

ATAGCTGGAAGTCCATCAAGTCTATCCTGGACTGGACCTCCTTCAATCAA

GAGCGGATCGTGGATGTGGCTGGCCCTGGCGGATGGAACGATCCTGATAT

GCTGGTCATCGGCAACTTCGGCCTGTCCTGGAACCAGCAAGTGACCCAGA

TGGCCCTGTGGGCCATTATGGCCGCTCCTCTGTTCATGTCCAACGACCTG

AGACACATCAGCCCTCAGGCCAAGGCTCTGCTGCAGGACAAGGATGTGAT

CGCTATCAACCAGGATCCTCTGGGCAAGCAGGGCTACCAGTTGAGACAGG

GCGACAACTTTGAAGTGTGGGAAAGACCCCTGTCCGGCCTGGCATGGGCT

GTCGCCATGATCAACAGACAAGAGATCGGCGGACCCCGGTCCTACACAAT

CGCTGTTGCTTCTCTCGGCAAAGGCGTGGCCTGCAATCCTGCCTGTTTCA

TCACACAGCTGCTGCCCGTGAAGAGAAAGCTGGGCTTTTACGAGTGGACC

TCTCGGCTGCGGTCCCACATCAATCCTACCGGAACAGTGCTGCTGCAGCT

GGAAAACACCATGCAGATGTCCCTGAAGGACCTGCTGGGATTCCTTGGCG

GAGGCGGAGGATCTGGTGGTGGCGGATCTAACAACCAGAAGATCGTCAAC

ATCAAAGAGAAGGTCGCCCAGATCGAGGCTGGCGGCGGTGGATCAGGTGG

CGGAGGAAGCAACAATCAGAAAATTGTGAATATCAAAGAAAAAGTGGCTC

AGATTGAAGCAGGCGGCGGAGGTAGCGGAGGTGGTGGCTCTAACAATCAA

AAAATCGTTAACATCAAAGAGAAAGTTGCTCAAATCGAAGCCGGCGGTGG

TGGTTCTGGCGGTGGTGGTAGTAACAATCAAAAGATCGTCAATATCAAAG

AAAAGGTGGCACAAATCGAGGCAGGCGGAGGCGGCTCTGGCGGCGGAGGA

TCAAACAATCAGAAGATCGTTAACATCAAAGAAAAAGTGGCCCAAATTGA

GGCCTGA

Sequence 9. cDNA sequence of the expression cassette for human αGal control.

(SEQ ID NO: 9)

ATGGGCTGGTCCTGCATCATTCTGTTTCTGGTGGCTACCGCCACCGGCGT

GCACTCTGATCACCACCACCATCACCACGACGATGACGACAAGCTGGACA

ACGGCCTGGCTAGAACCCCTACCATGGGATGGCTGCACTGGGAGAGATTC

ATGTGCAACCTGGACTGCCAAGAGGAACCCGACTCCTGCATCTCCGAGAA

GCTGTTCATGGAAATGGCCGAGCTGATGGTGTCCGAAGGCTGGAAGGATG

CCGGCTACGAGTACCTGTGCATCGACGACTGTTGGATGGCCCCTCAGAGA

GACTCTGAGGGCAGACTGCAGGCCGATCCTCAGAGATTTCCCCACGGCAT

CAGACAGCTGGCCAACTACGTGCACTCCAAGGGCCTGAAGCTGGGCATCT

ATGCCGACGTGGGCAACAAGACCTGTGCCGGCTTTCCTGGCTCCTTCGGC

TACTACGATATCGACGCCCAGACCTTCGCTGACTGGGGAGTCGATCTGCT

GAAGTTCGACGGCTGCTACTGCGACTCCCTGGAAAATCTGGCCGACGGCT

ACAAGCACATGTCTCTGGCCCTGAACCGGACCGGCAGATCCATCGTGTAT

AGCTGCGAGTGGCCCCTGTACATGTGGCCCTTCCAGAAGCCTAACTACAC

CGAGATCAGACAGTACTGCAACCACTGGCGGAACTTCGCCGACATCGACG

ATAGCTGGAAGTCCATCAAGTCTATCCTGGACTGGACCTCCTTCAATCAA

GAGCGGATCGTGGATGTGGCTGGCCCTGGCGGATGGAACGATCCTGATAT

GCTGGTCATCGGCAACTTCGGCCTGTCCTGGAACCAGCAAGTGACCCAGA

TGGCCCTGTGGGCCATTATGGCCGCTCCTCTGTTCATGTCCAACGACCTG

AGACACATCAGCCCTCAGGCCAAGGCTCTGCTGCAGGACAAGGATGTGAT

CGCTATCAACCAGGATCCTCTGGGCAAGCAGGGCTACCAGTTGAGACAGG

GCGACAACTTTGAAGTGTGGGAAAGACCCCTGTCCGGCCTGGCATGGGCT

GTCGCCATGATCAACAGACAAGAGATCGGCGGACCCCGGTCCTACACAAT

CGCTGTTGCTTCTCTCGGCAAAGGCGTGGCCTGCAATCCTGCCTGTTTCA

TCACACAGCTGCTGCCCGTGAAGAGAAAGCTGGGCTTTTACGAGTGGACC

TCTCGGCTGCGGTCCCACATCAATCCTACCGGAACAGTGCTGCTGCAGCT

GGAAAACACCATGCAGATGICCCTGAAGGACCTGCTGTGA

Sequence 10. cDNA sequence of the expression cassette for human glucocerebrosidase (GCasc) with one copy of the 2γ3 ICAM-1-targeting peptide at the amino terminus.

(SEQ ID NO: 10)

ATGGGCTGGTCCTGCATCATTCTGTTTCTGGTGGCTACCGCCACCGGCGT

GCACTCTGATCACCACCACCATCACCACGACGATGACGACAAGAACAACC

AGAAGATCGTCAACATCAAAGAGAAGGTCGCCCAGATCGAGGCTGGCGGC

GGAGGATCTGGCGGAGGCGGATCTGGATTTTTGGGAGCCAGACCTTGCAT

CCCCAAGTCCTTCGGCTACTCCTCTGTCGTGTGCGTGTGCAACGCCACCT

ACTGCGACAGCTTCGACCCTCCTACCTTTCCTGCTCTGGGCACATTCTCC

AGATACGAGTCCACCAGATCCGGCAGACGGATGGAACTGAGCATGGGCCC

TATCCAGGCTAACCATACCGGCACAGGACTGCTGCTGACACTGCAGCCCG

AGCAGAAATTCCAGAAAGTGAAAGGCTTCGGCGGAGCCATGACCGATGCC

-continued

GCCGCTCTGAATATTCTGGCTCTGAGCCCTCCTGCTCAGAACCTGCTGCT

CAAGTCCTACTTCTCCGAGGAAGGCATCGGCTACAACATCATCCGGGTGC

CAATGGCCTCCTGCGACTTCTCTATCCGGACCTACACCTACGCTGACACC

CCTGACGATTTCCAGCTGCACAACTTCAGCCTGCCTGAAGAGGACACCAA

GCTGAAGATCCCTCTGATCCACAGAGCCCTGCAGCTGGCTCAGAGGCCTG

TTTCTCTGCTGGCCTCTCCTTGGACCTCTCCAACCTGGCTGAAAACAAAT

GGCGCCGTGAACGGCAAGGGCTCCCTGAAAGGACAACCCGGCGATATCTA

CCACCAGACCTGGGCCAGATACTTCGTGAAGTTCCTGGACGCCTACGCCG

AGCACAAGCTGCAGTTTTGGGCTGTGACCGCCGAGAACGAGCCTTCTGCT

GGACTGCTGTCTGGCTACCCTTTCCAGTGCCTGGGCTTTACCCCTGAGCA

CCAGAGAGACTTTATCGCCAGAGATCTGGGCCCCACACTGGCCAATTCTA

CCCACCATAATGTGCGGCTGCTGATGCTGGACGACCAGAGACTGCTGTTG

CCCCACTGGGCTAAAGTGGTGCTGACCGATCCTGAGGCCGCCAAATACGT

-continued

GCACGGAATCGCCGTGCACTGGTATCTGGACTTTCTGGCCCCTGCCAAGG

CTACCCTGGGCGAGACACATAGACTGTTCCCCAACACCATGCTGTTCGCC

TCTGAGGCCTGTGTGGGCTCCAAGTTCTGGGAGCAGTCTGTGCGACTCGG

CTCTTGGGATAGAGGCATGCAGTACTCCCACTCCATCATCACCAACCTGC

TGTACCACGTCGTCGGCTGGACCGATTGGAACCTGGCACTGAATCCTGAA

GGCGGCCCTAACTGGGTCCGAAACTTCGTGGACTCCCCTATCATCGTGGA

CATCACCAAGGACACCTTCTACAAGCAGCCCATGTTCTACCATCTGGGCC

ACTTCAGCAAGTTCATCCCCGAGGGCTCTCAGAGAGTCGGCCTGGTTGCC

TCTCAGAAGAACGACCTGGACGCTGTGGCTCTGATGCACCCTGATGGATC

TGCTGTGGTGGTCGTGCTGAACCGGTCCTCCAAAGATGTGCCCCTGACCA

TCAAGGATCCCGCCGTGGGATTCCTGGAAACCATCTCTCCTGGCTACTCC

ATCCACACCTACCTGTGGCGTAGACAGTGA

Sequence 11. cDNA sequence of the expression cassette for human GCase with five tandem-repeats of the 2γ3 ICAM-1-targeting peptide at the amino terminus.

(SEQ ID NO: 11)

ATGGGCTGGTCCTGCATCATTCTGTTTCTGGTGGCTACCGCCACCGGCGTGCACTCTGATCA

CCACCACCATCACCACGACGATGACGACAAGAACAACCAGAAGATCGTCAACATCAAAGAGA

AGGTCGCCCAGATCGAGGCTGGCGGCGGAGGATCTGGCGGAGGCGGATCTAACAATCAGAAA

ATTGTGAATATCAAAGAAAAAGTGGCTCAGATTGAAGCCGGCGGTGGTGGTAGCGGTGGCGG

AGGAAGTAACAATCAAAAGATCGTGAACATCAAAGAAAAAGTTGCACAAATCGAGGCAGGCG

GTGGCGGCAGCGGAGGTGGTGGATCCAACAACCAGAAAATCGTGAACATCAAAGAAAAGGTG

GCCCAAATCGAAGCCGGCGGAGGCGGTTCAGGCGGCGGAGGTTCAAACAATCAGAAGATCGT

TAATATCAAAGAAAAGGTTGCCCAGATTGAGGCAGGCGGAGGTGGAAGCGGCGGAGGCGGCT

CTGGATTTTTGGGAGCCAGACCTTGCATCCCCAAGTCCTTCGGCTACTCCTCTGTCGTGTGC

GTGTGCAACGCCACCTACTGCGACAGCTTCGACCCTCCTACCTTTCCTGCTCTGGGCACATT

CTCCAGATACGAGTCCACCAGATCCGGCAGACGGATGGAACTGAGCATGGGCCCTATCCAGG

CTAACCATACCGGCACAGGACTGCTGCTGACACTGCAGCCCGAGCAGAAATTCCAGAAAGTG

AAAGGCTTCGGCGGAGCCATGACCGATGCCGCCGCTCTGAATATTCTGGCTCTGAGCCCTCC

TGCTCAGAACCTGCTGCTCAAGTCCTACTTCTCCGAGGAAGGCATCGGCTACAACATCATCC

GGGTGCCAATGGCCTCCTGCGACTTCTCTATCCGGACCTACACCTACGCTGACACCCCTGAC

GATTTCCAGCTGCACAACTTCAGCCTGCCTGAAGAGGACACCAAGCTGAAGATCCCTCTGAT

CCACAGAGCCCTGCAGCTGGCTCAGAGGCCTGTTTCTCTGCTGGCCTCTCCTTGGACCTCTC

CAACCTGGCTGAAAACAAATGGCGCCGTGAACGGCAAGGGCTCCCTGAAAGGACAACCCGGC

GATATCTACCACCAGACCTGGGCCAGATACTTCGTGAAGTTCCTGGACGCCTACGCCGAGCA

CAAGCTGCAGTTTTGGGCTGTGACCGCCGAGAACGAGCCTTCTGCTGGACTGCTGTCTGGCT

ACCCTTTCCAGTGCCTGGGCTTTACCCCTGAGCACCAGAGAGACTTTATCGCCAGAGATCTG

GGCCCCACACTGGCCAATTCTACCCACCATAATGTGCGGCTGCTGATGCTGGACGACCAGAG

ACTGCTGTTGCCCCACTGGGCTAAAGTGGTGCTGACCGATCCTGAGGCCGCCAAATACGTGC

ACGGAATCGCCGTGCACTGGTATCTGGACTTTCTGGCCCCTGCCAAGGCTACCCTGGGCGAG

ACACATAGACTGTTCCCCAACACCATGCTGTTCGCCTCTGAGGCCTGTGTGGGCTCCAAGTT

-continued

```
CTGGGAGCAGTCTGTGCGACTCGGCTCTTGGGATAGAGGCATGCAGTACTCCCACTCCATCA

TCACCAACCTGCTGTACCACGTCGTCGGCTGGACCGATTGGAACCTGGCACTGAATCCTGAA

GGCGGCCCTAACTGGGTCCGAAACTTCGTGGACTCCCCTATCATCGTGGACATCACCAAGGA

CACCTTCTACAAGCAGCCCATGTTCTACCATCTGGGCCACTTCAGCAAGTTCATCCCCGAGG

GCTCTCAGAGAGTCGGCCTGGTTGCCTCTCAGAAGAACGACCTGGACGCTGTGGCTCTGATG

CACCCTGATGGATCTGCTGTGGTGGTCGTGCTGAACCGGTCCTCCAAAGATGTGCCCCTGAC

CATCAAGGATCCCGCCGTGGGATTCCTGGAAACCATCTCTCCTGGCTACTCCATCCACACCT

ACCTGTGGCGTAGACAGTGA
```

Sequence 12. cDNA sequence of the expression cassette for human GCase control.

```
                                                    (SEQ ID NO: 12)
ATGGGCTGGTCCTGCATCATTCTGTTTCTGGTGGCTACCGCCACCGGCGTGCACTCTGATCA

CCACCACCATCACCACGACGATGACGACAAGCTGGACAACGGCCTGGCTAGAACCCCTACCA

TGGGATGGCTGCACTGGGAGAGATTCATGTGCAACCTGGACTGCCAAGAGGAACCCGACTCC

TGCATCTCCGAGAAGCTGTTCATGGAAATGGCCGAGCTGATGGTGTCCGAAGGCTGGAAGGA

TGCCGGCTACGAGTACCTGTGCATCGACGACTGTTGGATGGCCCCTCAGAGAGACTCTGAGG

GCAGACTGCAGGCCGATCCTCAGAGATTTCCCCACGGCATCAGACAGCTGGCCAACTACGTG

CACTCCAAGGGCCTGAAGCTGGGCATCTATGCCGACGTGGGCAACAAGACCTGTGCCGGCTT

TCCTGGCTCCTTCGGCTACTACGATATCGACGCCCAGACCTTCGCTGACTGGGGAGTCGATC

TGCTGAAGTTCGACGGCTGCTACTGCGACTCCCTGGAAAATCTGGCCGACGGCTACAAGCAC

ATGTCTCTGGCCCTGAACCGGACCGGCAGATCCATCGTGTATAGCTGCGAGTGGCCCCTGTA

CATGTGGCCCTTCCAGAAGCCTAACTACACCGAGATCAGACAGTACTGCAACCACTGGCGGA

ACTTCGCCGACATCGACGATAGCTGGAAGTCCATCAAGTCTATCCTGGACTGGACCTCCTTC

AATCAAGAGCGGATCGTGGATGTGGCTGGCCCTGGCGGATGGAACGATCCTGATATGCTGGT

CATCGGCAACTTCGGCCTGTCCTGGAACCAGCAAGTGACCCAGATGGCCCTGTGGGCCATTA

TGGCCGCTCCTCTGTTCATGTCCAACGACCTGAGACACATCAGCCCTCAGGCCAAGGCTCTG

CTGCAGGACAAGGATGTGATCGCTATCAACCAGGATCCTCTGGGCAAGCAGGGCTACCAGTT

GAGACAGGGCGACAACTTTGAAGTGTGGGAAAGACCCCTGTCCGGCCTGGCATGGGCTGTCG

CCATGATCAACAGACAAGAGATCGGCGGACCCCGGTCCTACACAATCGCTGTTGCTTCTCTC

GGCAAAGGCGTGGCCTGCAATCCTGCCTGTTTCATCACACAGCTGCTGCCCGTGAAGAGAAA

GCTGGGCTTTTACGAGTGGACCTCTCGGCTGCGGTCCCACATCATCCTACCGGAACAGTGC

TGCTGCAGCTGGAAAACACCATGCAGATGTCCCTGAAGGACCTGCTGTGA
```

Sequence 13. Amino acid sequence of the expression cassette for human acid sphingomyelinase (ASM) with one copy of the 2γ3 ICAM-1-targeting peptide at the amino terminus

```
(SEQ ID NO: 13)
METDTLLLWVLLLWVPGSTGDHHHHHHDDDDKNNQKIVNIKEKVAQIEAG

GGGSGGGGSGFLGHPLSPQGHPARLHRIVPRLRDVFGWGNLTCPICKGLF

TAINLGLKKEPNVARVGSVAIKLCNLLKIAPPAVCQSIVHLFEDDMVEVW

RRSVLSPSEACGLLLGSTCGHWDIFSSWNISLPTVPKPPPKPPSPPAPGA

PVSRILFLTDLHWDHDYLEGTDPDCADPLCCRRGSGLPPASRPGAGYWGE

YSKCDLPLRTLESLLSGLGPAGPFDMVYWTGDIPAHDVWHQTRQDQLRAL

TTVTALVRKFLGPVPVYPAVGNHESTPVNSFPPPFIEGNHSSRWLYEAMA

KAWEPWLPAEALRTLRIGGFYALSPYPGLRLISLNMNFCSRENFWLLINS

TDPAGQLQWLVGELQAAEDRGDKVHIIGHIPPGHCLKSWSWNYYRIVARY

ENTLAAQFFGHTHVDEFEVFYDEETLSRPLAVAFLAPSATTYIGLNPGYR

VYQIDGNYSGSSHVVLDHETYILNLTQANIPGAIPHWQLLYRARETYGLP

NTLPTAWHNLVYRMRGDMQLFQTFWFLYHKGHPPSEPCGTPCRLATLCAQ

LSARADSPALCHRLMPDGSLPEAQSLWPRPLFC*
```

Sequence 14. Amino acid sequence of the expression cassette for human ASM with five tandem-repeats of the 2γ3 ICAM-1-targeting peptide at the amino terminus.

```
(SEQ ID NO: 14)
METDTLLLWVLLLWVPGSTGDHHHHHHDDDDKNNQKIVNIKEKVAQIEAG

GGGSGGGGSNNQKIVNIKEKVAQIEAGGGGSGGGGSNNQKIVNIKEKVAQ

IEAGGGGSGGGGSNNQKIVNIKEKVAQIEAGGGGSGGGGSNNQKIVNIKE

KVAQIEAGGGGSGGGGSGFLGHPLSPQGHPARLHRIVPRLRDVFGWGNLT

CPICKGLFTAINLGLKKEPNVARVGSVAIKLCNLLKIAPPAVCQSIVHLF

EDDMVEVWRRSVLSPSEACGLLLGSTCGHWDIFSSWNISLPTVPKPPPKP

PSPPAPGAPVSRILFLTDLHWDHDYLEGTDPDCADPLCCRRGSGLPPASR

PGAGYWGEYSKCDLPLRTLESLLSGLGPAGPFDMVYWTGDIPAHDVWHQT

RQDQLRALTTVTALVRKFLGPVPVYPAVGNHESTPVNSFPPPFIEGNHSS

RWLYEAMAKAWEPWLPAEALRTLRIGGFYALSPYPGLRLISLNMNFCSRE

NFWLLINSTDPAGQLQWLVGELQAAEDRGDKVHIIGHIPPGHCLKSWSWN

YYRIVARYENTLAAQFFGHTHVDEFEVFYDEETLSRPLAVAFLAPSATTY

IGLNPGYRVYQIDGNYSGSSHVVLDHETYILNLTQANIPGAIPHWQLLYR

ARETYGLPNTLPTAWHNLVYRMRGDMQLFQTFWFLYHKGHPPSEPCGTPC

RLATLCAQLSARADSPALCRHLMPDGSLPEAQSLWPRPLFC*
```

Sequence 15. Amino acid sequence of the expression cassette for human ASM with ten tandem-repeats of the 2γ3 ICAM-1-targeting peptide at the amino terminus.

```
(SEQ ID NO: 15)
METDTLLLWVLLLWVPGSTGDHHHHHHDDDDKNNQKIVNIKEKVAQIEAG

GGGSGGGGSNNQKIVNIKEKVAQIEAGGGGSGGGGSNNQKIVNIKEKVAQ

IEAGGGGSGGGGSNNQKIVNIKEKVAQIEAGGGGSGGGGSNNQKIVNIKE

KVAQIEAGGGGSGGGGSNNQKIVNIKEKVAQIEAGGGGSGGGGSNNQKIV

NIKEKVAQIEAGGGGSGGGGSNNQKIVNIKEKVAQIEAGGGGSGGGGSNN

KQIVNIKEKVAQIEAGGGGSGGGGSNNQKIVNIKEKVAQIEAGGGGSGGG

GSFLGHPLSPQGHPARLHRIVPRLRDVFGWGNLTCPICKGLFTAINLGLK

KEPNVARVGSVAIKLCNLLKIAPPAVCQSIVHLFEDDMVEVWRRSVLSPS

EACGLLLGSTCGHWDIFSSWNISLPTVPKPPPKPPSPPAPGAPVSRILFL

TDLHWDHDYLEGTDPDCADPLCCRRGSGLPPASRPGAGYWGEYSKCDLPL

PLRTLESLLSGLGPAGPFDMVYWTGDIPAHDVWHQTRQDQLRALTTVTAL

VRKFLGPVPVYPAVGNHESTPVNSFPPPFIEGNHSSRWLYEAMAKAWEPW

LPAEALRTLRIGGFYALSPYPGLRLISLNMNFCSRENFWLLINSTDPAGQ

LQWLVGELQAAEDRGDKVHIIGHIPPGHCLKSWSWNYYRIVARYENTLAA

QFFGHTHVDEFEVFYDEETLSRPLAVAFLAPSATTYIGLNPGYRVYQIDG

NYSGSSHVVLDHETYILNLTQANIPGAIPHWQLLYRARETYGLPNTLPTA

WHNLVYRMRGDMQLFQTFWFLYHKGHPPSEPCGTPCRLATLCAQLSARAD

SPALCHRLMPDGSLPEAQSLWPRPLFC*
```

Sequence 16. Amino acid sequence of the expression cassette for human ASM with five tandem-repeats of the 2γ3 ICAM-1-targeting peptide at the carboxyl terminus.

```
(SEQ ID NO: 16)
METDTLLLWVLLLWVPGSTGDHHHHHHDDDDKHPLSPQGHPARLHRIVPR

LRDVFGWGNLTCPICKGLFTAINLGLKKEPNVARVGSVAIKLCNLLKIAP

PAVCQSIVHLFEDDMVEVWRRSVLSPSEACGLLLGSTCGHWDIFSSWNIS

LPTVPKPPPKPPSPPAPGAPVSRILFLTDLHWDHDYLEGTDPDCADPLCC

RRGSGLPPASRPGAGYWGEYSKCDLPLRTLESLLSGLGPAGPFDMVYWTG

DIPAHDVWHQTRQDQLRALTTVTALVRKFLGPVPVYPAVGNHESTPVNSF

PPPFIEGNHSSRWLYEAMAKAWEPWLPAEALRTLRIGGFYALSPYPGLRL

ISLNMNFCSRENFWLLINSTDPAGQLQWLVGELQAAEDRGDKVHIIGHIP

PGHCLKSWSWNYYRIVARYENTLAAQFFGHTHVDEFEVFYDEETLSRPLA

VAFLAPSATTYIGLNPGYRVYQIDGNYSGSSHVVLDHETYILNLTQANIP

GAIPHWQLLYRARETYGLPNTLPTAWHNLVYRMRGDMQLFQTFWFLYHKG

HPPSEPCGTPCRLATLCAQLSARADSPALCRHLMPDGSLPEAQSLWPRPL

FCGFLGGGGSGGGGSNNQKIVNIKEKVAQIEAGGGGSGGGGSNNQKIVN

IKEKVAQIEAGGGGSGGGGSNNQKIVNIKEKVAQIEAGGGGSGGGGSNNQ

KIVNIKEKVAQIEAGGGGSGGGGSNNQKIVNIKEKVAQIEA*
```

Sequence 17. Amino acid sequence of the expression cassette for human ASM control.

```
(SEQ ID NO: 17)
METDTLLLWVLLLWVPGSTGDHHHHHHDDDDKHPLSPQGHPARLHRIVPR

LRDVFGWGNLTCPICKGLFTAINLGLKKEPNVARVGSVAIKLCNLLKIAP

PAVCQSIVHLFEDDMVEVWRRSVLSPSEACGLLLGSTCGHWDIFSSWNIS
```

-continued

LPTVPKPPPKPPSPPAPGAPVSRILFLTDLHWDHDYLEGTDPDCADPLCC

RRGSGLPPASRPGAGYWGEYSKCDLPLRTLESLLSGLGPAGPFDMVYWTG

DIPAHDVWHQTRQDQLRALTTVTALVRKFLGPVPVYPAVGNHESTPVNSF
PPPFIEGNHSSRWLYEAMAKAWEPWLPAEALRTLRIGGFYALSPYPGLRL
ISLNMNFCSRENFWLLINSTDPAGQLQWLVGELQAAEDRGDKVHIIGHIP

PGHCLKSWSWNYYRIVARYENTLAAQFFGHTHVDEFEVFYDEETLSRPLA

VAFLAPSATTYIGLNPGYRVYQIDGNYSGSSHVVLDHETYILNLTQANIP

GAIPHWQLLYRARETYGLPNTLPTAWHNLVYRMRGDMQLFQTFWFLYHKG

HPPSEPCGTPCRLATLCAQLSARADSPALCRHLMPDGSLPEAQSLWPRPL

FC*

Sequence 18. Amino acid sequence of the expression cassette for human alpha galactosidase (αGal) with one copy of the 2γ3 ICAM-1-targeting peptide at the amino terminus.

(SEQ ID NO: 18)
MGWSCIILFLVATATGVHSDHHHHHHDDDDKNNQKIVNIKEKVAQIEAGG
GGSGGGGSGFLGLDNGLARTPTMGWLHWERFMCNLDCQEEPDSCISEKLF
MEMAELMVSEGWKDAGYEYLCIDDCWMAPQRDSEGRLQADPQRFPHGIRQ
LANYVHSKGLKLGIYADVGNKTCAGFPGSFGYYDIDAQTFADWGVDLLKF
DGCYCDSLENLADGYKHMSLALNRTGRSIVYSCEWPLYMWPFQKPNYTEI
RQYCNHWRNFADIDDSWKSIKSILDWTSFNQERIVDVAGPGGWNDPDMLV
IGNFGLSWNQQVTQMALWAIMAAPLFMSNDLRHISPQAKALLQDKDVIAI
NQDPLGKQGYQLRQGDNFEVWERPLSGLAWAVAMINRQEIGGPRSYTIAV
ASLGKGVACNPACFITQLLPVKRKLGFYEWTSRLRSHINPTGTVLLQLEN
TMQMSLKDLL*

Sequence 19. Amino acid sequence of the expression cassette for human αGal with five tandem-repeats of the 2γ3 ICAM-1-targeting peptide at the carboxyl terminus.

(SEQ ID NO: 19)
MGWSCIILFLVATATGVHSDHHHHHHDDDDKLDNGLARTPTMGWLHWERF
MCNLDCQEEPDSCISEKLFMEMAELMVSEGWKDAGYEYLCIDDCWMAPQR
DSEGRLQADPQRFPHGIRQLANYVHSKGLKLGIYADVGNKTCAGFPGSFG
MSYYDIDAQTFADWGVDLLKFDGCYCDSLENLADGYKHLALNRTGRSIVY
SCEWPLYMWPFQKPNYTEIRQYCNHWRNFADIDDSWKSIKSILDWTSFNQ
ERIVDVAGPGGWNDPDMLVIGNFGLSWNQQVTQMALWAIMAAPLFMSNDL
RHISPQAKALLQDKDVIAINQDPLGKQGYQLRQGDNFEVWERPLSGLAWA
VAMINRQEIGGPRSYTIAVASLGKGVACNPACFITQLLPVKRKLGFYEWT
SRLRSHINPTGTVLLQLENTMQMSLKDLLGFLGGGGGSGGGGSNNQKIVN
IKEKVAQIEAGGGGSGGGGSNNQKIVNIKEKVAQIEAGGGGSGGGGSNNQ
KIVNIKEKVAQIEAGGGGSGGGGSNNQKIVNIKEKVAQIEAGGGGSGGGG
SNNQKIVNIKEKVAQIEA*

Sequence 20. Amino acid sequence of the expression cassette for human αGal control.

(SEQ ID NO: 20)
MGWSCIILFLVATATGVHSDHHHHHHDDDDKLDNGLARTPTMGWLHWERF
MCNLDCQEEPDSCISEKLFMEMAELMVSEGWKDAGYEYLCIDDCWMAPQR
DSEGRLQADPQRFPHGIRQLANYVHSKGLKLGIYADVGNKTCAGFPGSFG
YYDIDAQTFADWGVDLLKFDGCYCDSLENLADGYKHMSLALNRTGRSIVY
SCEWPLYMWPFQKPNYTEIRQYCNHWRNFADIDDSWKSIKSILDWTSFNQ
ERIVDVAGPGGWNDPDMLVIGNFGLSWNQQVTQMALWAIMAAPLFMSNDL
RHISPQAKALLQDKDVIAINQDPLGKQGYQLRQGDNFEVWERPLSGLAWA
VAMINRQEIGGPRSYTIAVASLGKGVACNPACFITQLLPVKRKLGFYEWT
SRLRSHINPTGTVLLQLENTMQMSLKDLL*

Sequence 21. Amino acid sequence of the expression cassette for human glucocerebrosidase (GCase) with one copy of the 2γ3 ICAM-1-targeting peptide at the amino terminus.

(SEQ ID NO: 21)
MGWSCIILFLVATATGVHSDHHHHHHDDDDKNNQKIVNIKEKVAQIEAGG
GGSGGGGSGFLGARPCIPKSFGYSSVVCVCNATYCDSFDPPTFPALGTFS
RYESTRSGRRMELSMGPIQANHTGTGLLLTLQPEQKFQKVKGFGGAMTDA
AALNILALSPPAQNLLLKSYFSEEGIGYNIIRVPMASCDFSIRTYTYADT
PDDFQLHNFSLPEEDTKLKIPLIHRALQLAQRPVSLLASPWTSPTWLKTN
GAVNGKGSLKGQPGDIYHQTWARYFVKFLDAYAEHKLQFWAVTAENEPSA
GLLSGYPFQCLGFTPEHQRDFIARDLGPTLANSTHHNVRLLMLDDQRLLL
PHWAKVVLTDPEAAKYVHGIAVHWYLDFLAPAKATLGETHRLFPNTMLFA
SEACVGSKFWEQSVRLGSWDRGMQYSHSIITNLLYHVVGWTDWNLALNPE
GGPNWVRNFVDSPIIVDITKDTFYKQPMFYHLGHFSKFIPEGSQRVGLVA
SQKNDLDAVALMHPDGSAVVVVLNRSSKDVPLTIKDPAVGFLETISPGYS
IHTYLWRRQ*

Sequence 22. Amino acid sequence of the expression cassette for human GCase with five tandem-repeats of the 2γ3 ICAM-1-targeting peptide at the amino terminus.

(SEQ ID NO: 22)
MGWSCIILFLVATATGVHSDHHHHHHDDDDKNNQKIVNIKEKVAQIEAGG
GGSGGGGSNNQKIVNIKEKVAQIEAGGGGSGGGGSNNQKIVNIKEKVAQI
EAGGGGSGGGGSNNQKIVNIKEKVAQIEAGGGGSGGGGSNNQKIVNIKEK
VAQIEAGGGGSGGGGSGFLGARPCIPKSFGYSSVVCVCNATYCDSFDPPT
FPALGTFSRYESTRSGRRMELSMGPIQANHTGTGLLLTLQPEQKFQKVKG
FGGAMTDAAALNILALSPPAQNLLLKSYFSEEGIGYNIIRVPMASCDFSI
RTYTYADTPDDFQLHNFSLPEEDTKLKIPLIHRALQLAQRPVSLLASPWT
SPTWLKTNGAVNGKGSLKGQPGDIYHQTWARYFVKFLDAYAEHKLQFWAV
TAENEPSAGLLSGYPFQCLGFTPEHQRDFIARDLGPTLANSTHHNVRLLM

```
-continued
LDDQRLLLPHWAKVVLTDPEAAKYVHGIAVHWYLDFLAPAKATLGETHRL

FPNTMLFASEACVGSKFWEQSVRLGSWDRGMQYSHSIITNLLYHVVGWTD

WNLALNPEGGPNWVRNFVDSPIIVDITKDTFYKQPMFYHLGHFSKFIPEG

SQRVGLVASQKNDLDAVALMHPDGSAVVVVLNRSSKDVPLTIKDPAVGFL

ETISPGYSIHTYLWRRQ*
```

Sequence 23. Amino acid sequence of the expression cassette for human GCase control.

```
                                           (SEQ ID NO: 23)
MGWSCIILFLVATATGVHSDHHHHHHDDDDKARPCIPKSFGYSSVVCVCN

ATYCDSFDPPTFPALGTFSRYESTRSGRRMELSMGPIQANHTGTGLLLTL

QPEQKFQKVKGFGGAMTDAAALNILALSPPAQNLLLKSYFSEEGIGYNII

RVPMASCDFSIRTYTYADTPDDFQLHNFSLPEEDTKLKIPLIHRALQLAQ

RPVSLLASPWTSPTWLKTNGAVNGKGSLKGQPGDIYHQTWARYFVKFLDA

YAEHKLQFWAVTAENEPSAGLLSGYPFQCLGFTPEHQRDFIARDLGPTLA

NSTHHNVRLLMLDDQRLLLPHWAKVVLTDPEAAKYVHGIAVHWYLDFLAP

AKATLGETHRLFPNTMLFASEACVGSKFWEQSVRLGSWDRGMQYSHSIIT

NLLYHVVGWTDWNLALNPEGGPNWVRNFVDSPIIVDITKDTFYKQPMFYH

LGHFSKFIPEGSQRVGLVASQKNDLDAVALMHPDGSAVVVVLNRSSKDVP

LTIKDPAVGFLETISPGYSIHTYLWRRQ*
```

Sequence 24. Amino acid sequence of a glycine-serine linker.

```
                                           (SEQ ID NO: 24)
GGGGS
```

Sequence 25. Amino acid sequence of a two repeats of the glycine-serine linker.

```
                                           (SEQ ID NO: 25)
GGGGSGGGGS
```

Sequence 26. Amino acid sequence of alternative ICAM-1 targeting peptide.

```
                                           (SEQ ID NO: 26)
NNQKIVNLKEKVAQLEA
```

Sequence 27. Amino acid sequence of alternative ICAM-1 targeting peptide.

```
                                           (SEQ ID NO: 27)
NNQKLVNIKEKVAQIEA
```

Sequence 28. Amino acid sequence of alternative ICAM-1 targeting peptide.

```
                                           (SEQ ID NO: 28)
YPASYQR
```

Sequence 29. Amino acid sequence of alternative ICAM-1 targeting peptide.

```
                                           (SEQ ID NO: 29)
YQATPLP
```

Sequence 30. Amino acid sequence of alternative ICAM-1 targeting peptide.

```
                                           (SEQ ID NO: 30)
GSLLSAA
```

Sequence 31. Amino acid sequence of alternative ICAM-1 targeting peptide.

```
                                           (SEQ ID NO: 31)
FSPHSRT
```

Sequence 32. Amino acid sequence of alternative ICAM-1 targeting peptide.

```
                                           (SEQ ID NO: 32)
YPFLPTA
```

Sequence 33. Amino acid sequence of alternative ICAM-1 targeting peptide.

```
                                           (SEQ ID NO: 33)
GCKLCAQ
```

Sequence 34. Amino acid sequence of the first protease cleavage site, recognized by cathepsin L or cathepsin B, in the fusion proteins.

```
                                           (SEQ ID NO: 34)
GFLG
```

Sequence 35. Amino acid sequence of the second protease cleavage site, the enterokinase cleavage sequence, in the fusion proteins.

```
                                           (SEQ ID NO: 35)
DDDDK
```

Sequence 36. Amino acid sequence of the second protease cleavage site, the Tobacco etch virus cleavage sequence, in the fusion proteins.

```
                                           (SEQ ID NO: 36)
ENLYFQ
```

Sequence 37. Amino acid sequence of the second protease cleavage site, the Factor Xa cleavage site, in the fusion proteins.

```
                                           (SEQ ID NO: 37)
IEGR
```

Sequence 38. Amino acid sequence of the second protease cleavage site, the matrix metalloproteinase 9 (MMP-9) cleavage site, in the fusion proteins.

PXXXX, where X in position 2 and 3 is any residue, position 3 is a hydrophobic residue, and the X in position 5 is S or T (SEQ ID NO:38).

Sequence 39. Amino acid sequence of the second protease cleavage site, the papain cleavage site, in the fusion proteins.

XXXXZRUXXX, where Z is a hydrophobic residue, and U is any residue but V (SEQ ID NO:39)

Sequence 40. Amino acid sequence of the second protease cleavage site, the thrombin cleavage site, in the fusion proteins.

```
(SEQ ID NO: 40)
LVPRGS
```

Sequence 41. Amino acid sequence of a secretion signal in the fusion proteins.

```
(SEQ ID NO: 41)
METDTLLLWVLLLWVPGSTG
```

Sequence 42. Amino acid sequence of a secretion signal in the fusion proteins.

```
(SEQ ID NO: 42)
MGWSCIILFLVATATGVHSD
```

REFERENCE

He, X., et al. (1999). "Characterization of human acid sphingomyelinase purified from the media of overexpressing Chinese hamster ovary cells." Biochimica et Biophysica Acta (BBA)-Protein Structure and Molecular Enzymology 1432 (2): 251-264.

The foregoing Examples and Sequences illustrate various embodiments, but do are not intended to limit the disclosure, and those skilled in the art will recognize that various modifications to the Examples and Sequences can be made without departing from the scope of the invention.

```
                              SEQUENCE LISTING

Sequence total quantity: 42
SEQ ID NO: 1            moltype = AA  length = 17
FEATURE                 Location/Qualifiers
source                  1..17
                        mol_type = protein
                        organism = Homo sapiens
SEQUENCE: 1
NNQKIVNIKE KVAQIEA                                                 17

SEQ ID NO: 2            moltype = DNA  length = 1902
FEATURE                 Location/Qualifiers
misc_feature            1..1902
                        note = cDNA sequence of the expression cassette for human
                         acid sphingomyelinase (ASM) with one copy of the 2gamma3
                         ICAM-1-targeting peptide at the amino terminus
source                  1..1902
                        mol_type = other DNA
                        organism = synthetic construct
SEQUENCE: 2
atggagaccg acacactgct cctgtgggtc ctgctcctct gggtgccagg aagtacagga  60
gatcaccatc accatcacca cgacgacgac gacaagaata accaaaagat tgtgaatatc  120
aaagagaaag tggctcagat tgaggctgga ggcggaggaa gcggcggcgg aggaagcgga  180
tttctgggac accctctttc tccccaaggc catcctgcca ggttacatcg catagtgccc  240
cggctccgag atgtctttgg gtgggggaac ctcacctgcc caatctgcaa aggtctattc  300
accgccatca acctcgggct gaagaaggaa cccaatgtgg ctcgcgtggg ctccgtggcc  360
atcaagctgt gcaatctgct gaagatagca ccacctgccg tgtgccaatc cattgtccac  420
ctctttgagg atgacatggt ggaggtgtgg agacgctcag tgctgagccc atctgaggcc  480
tgtggcctgc tcctgggctc cacctgtggg cactgggaca ttttctcatc ttggaacatc  540
tctttgccta ctgtgccgaa gccgcccccc aaacccccta gccccccagc cccaggtgcc  600
cctgtcagcc gcatcctctt cctcactgac ctgcactggg atcatgacta cctggagggc  660
acggaccctg actgtgcaga cccactgtgc tgccgccggg gttctggcct gccgcccgca  720
tcccggccag gtgccggata ctggggcgaa tacagcaagt gtgacctgcc cctgaggacc  780
ctggagagcc tgttgagtgg gctgggccca gccggccctt ttgatatggt gtactggaca  840
ggagacatcc ccgcacatga tgtctggcac cagactcgtc aggaccaact gcgggccctg  900
accaccgtca cagcacttgt gaggaagttc ctggggccag tgccagtgta ccctgctgtg  960
ggtaaccatg aaagcacacc tgtcaatagc ttccctcccc ccttcattga gggcaaccac  1020
tcctcccgct ggctctatga agcgatggcc aaggcttggg agccctggct gcctgccgaa  1080
gccctgcgca ccctcagaat tggggggttc tatgctcttt ccccataccc cggtctccgc  1140
ctcatctctc tcaatatgaa tttttgttcc cgtgagaact tctggctctt gatcaactcc  1200
acggatcccg caggacagct ccagtggctg gtgggggagc ttcaggctgc tgaggatcga  1260
ggagacaaag tgcatataat tggccacatt cccccagggc actgtctgaa gagctggagc  1320
tggaattatt accgaattgt agccaggtat gagaacaccc tggctgctca gttctttggc  1380
cacactcatg tggatgaatt tgaggtcttc tatgatgaag agactctgag ccggccgctg  1440
gctgtagcct tcctggcacc cagtgcaact acctacatcg gccttaatcc tggttaccgt  1500
gtgtaccaaa tagatggaaa ctactccggg agctctcacg tggtcctgga ccatgagacc  1560
tacatcctga atctgaccca ggcaaacata ccgggagcca taccgcactg gcagcttctc  1620
tacagggctc gagaaaccta tgggctgccc aacacactgc ctaccgcctg gcacaacctg  1680
gtatatcgca tgcggggcga catgcaactt ttccagacct tctggtttct ctaccataag  1740
ggccacccac cctcggagcc ctgtggcacg ccctgccgtc tggctactct ttgtgcccag  1800
ctctctgccc gtgctgacag ccctgctctg tgccgccacc tgatgccaga tgggagcctc  1860
ccagaggccc agagcctgtg gccaaggcca ctgttttgct ag                    1902

SEQ ID NO: 3            moltype = DNA  length = 2226
FEATURE                 Location/Qualifiers
```

-continued

```
misc_feature           1..2226
                       note = cDNA sequence of the expression cassette for human
                        ASM with five tandem-repeats of the 2?3 ICAM-1-targeting
                        peptide at the amino terminus.
source                 1..2226
                       mol_type = other DNA
                       organism = synthetic construct
SEQUENCE: 3
atggagaccg acacactgct cctgtgggtc ctgctcctct gggtgccagg aagtacagga  60
gatcaccatc accatcacca cgacgacgac gacaagaata accaaaagat tgtgaatatc  120
aaagagaaag tggctcagat tgaggctgga ggcggaggaa gcggcggcgg aggaagcaat  180
aatcagaaaa tcgtcaacat taaggaaaag gtcgcccaga ttgaagcagg aggcggcggc  240
agcggcggag gcggaagcaa taatcagaag attgttaaca tcaaagaaaa ggtggcccaa  300
attgaagcag gaggaggagg atctggaggc ggaggcagca ataaccagaa gatcgtcaac  360
atcaaggaaa aggtggctca gatcgaggca ggaggcggag gaagcggagg gggcggctct  420
aacaaccaga aaatcgtgaa catcaaagag aaagtggctc agatcgaagc cggcggagga  480
ggatccggag gaggaggaag cggatttctg ggacaccctc tttctcccca aggccatcct  540
gccaggttac atcgcatagt gccccggctc cgagatgtct ttgggtgggg gaacctcacc  600
tgcccaatct gcaaaggtct attcaccgcc atcaacctcg ggctgaagaa ggaacccaat  660
gtggctcgcg tgggctccgt ggccatcaag ctgtgcaatc tgctgaagat agcaccacct  720
gccgtgtgcc aatccattgt ccacctcttt gaggatgaca tggtggaggt gtggagacgc  780
tcagtgctga gcccatctga ggcctgtggc ctgctcctgg gctccacctg tgggcactgg  840
gacattttct catcttggaa catctctttg cctactgtgc cgaagccgcc ccccaaaccc  900
cctagccccc cagccccagg tgcccctgtc agccgcatcc tcttcctcac tgacctgcac  960
tgggatcatg actacctgga gggcacggac cctgactgtg cagacccact gtgctgccgc  1020
cggggttctg gcctgccgcc cgcatcccgg ccaggtgccg gatactgggg cgaatacagc  1080
aagtgtgacc tgcccctgag gaccctggag agcctgttga gtgggctggg cccagccggc  1140
ccttttgata tggtgtactg gacaggagac atccccgcac atgatgtctg gcaccagact  1200
cgtcaggacc aactgcgggc cctgaccacc gtcacagcac ttgtgaggaa gttcctgggg  1260
ccagtgccag tgtaccctgc tgtgggtaac catgaaagca cacctgtcaa tagcttccct  1320
ccccccttca ttgagggcaa ccactcctcc cgctggctct atgaagcgat ggccaaggct  1380
tgggagccct ggctgcctgc cgaagccctg cgcaccctca gaattggggg gttctatgct  1440
ctttccccat accccggtct ccgcctcatc tctctcaata tgaatttttg ttcccgtgag  1500
aacttctggc tcttgatcaa ctccacggat cccgcaggac agctccagtg gctggtgggg  1560
gagcttcagg ctgctgagga tcgaggagac aaagtgcata taattggcca cattccccca  1620
gggcactgtc tgaagagctg gagctggaat tattaccgaa ttgtagccag gtatgagaac  1680
accctggctg ctcagttctt tggccacact catgtggatg aatttgaggt cttctatgat  1740
gaagagactc tgagccggcc gctggctgta gccttcctgg cacccagtgc aactacctac  1800
atcggcctta atcctggtta ccgtgtgtac caaatagatg gaaactactc cgggagctct  1860
cacgtggtcc tggaccatga gacctacatc ctgaatctga cccaggcaaa cataccggga  1920
gccataccgc actggcagct tctctacagg gctcgagaaa cctatgggct gcccaacaca  1980
ctgcctaccg cctggcacaa cctggtatat cgcatgcggg gcgacatgca acttttccag  2040
accttctggt ttctctacca taagggccac ccaccctcgg agccctgtgg cacgccctgc  2100
cgtctggcta ctctttgtgc ccagctctct gcccgtgctg acagccctgc tctgtgccgc  2160
cacctgatgc cagatgggag cctcccagag gcccagagcc tgtggccaag gccactgttt  2220
tgctag                                                             2226

SEQ ID NO: 4           moltype = DNA  length = 2631
FEATURE                Location/Qualifiers
misc_feature           1..2631
                       note = cDNA sequence of the expression cassette for human
                        ASM with ten tandem-repeats of the 2gamma3
                        ICAM-1-targeting peptide at the amino terminus
source                 1..2631
                       mol_type = other DNA
                       organism = synthetic construct
SEQUENCE: 4
atggagaccg acacactgct cctgtgggtc ctgctcctct gggtgccagg aagtacagga  60
gatcaccatc accatcacca cgacgacgac gacaagaata accaaaagat tgtgaatatc  120
aaagagaaag tggctcagat tgaggctgga ggcggaggaa gcggcggcgg aggaagcaat  180
aatcagaaaa tcgtcaacat taaggaaaag gtcgcccaga ttgaagcagg aggcggcggc  240
agcggcggag gcggaagcaa taatcagaag attgttaaca tcaaagaaaa ggtggcccaa  300
attgaagcag gaggaggagg atctggaggc ggaggcagca ataaccagaa gatcgtcaac  360
atcaaggaaa aggtggctca gatcgaggca ggaggcggag gaagcggagg gggcggctct  420
aacaaccaga aaatcgtgaa catcaaagag aaagtggctc agatcgaagc cggcggagga  480
ggatccggag gaggaggaag caataaccaa aagattgtga atatcaaaga gaaagtggct  540
cagattgagg ctggaggcgg aggaagcggc ggcggaggaa gcaataatca gaaaatcgtc  600
aacattaagg aaaaggtcgc ccagattgaa gcaggaggcg gcggcagcgg cggaggcgga  660
agcaataatc agaagattgt taacatcaaa gaaaaggtgg cccaaattga agcaggagga  720
ggaggatctg gaggcggagg cagcaataac cagaagatcg tcaacatcaa ggaaaaggtg  780
gctcagatcg aggcaggagg cggaggaagc ggagggggcg gctctaacaa ccagaaaatc  840
gtgaacatca aagagaaagt ggctcagatc gaagccggcg gaggaggatc cggaggagga  900
ggaagcggat ttctgggaca ccctctttct ccccaaggcc atcctgccag gttacatcgc  960
atagtgcccc ggctccgaga tgtctttggg tgggggaacc tcacctgccc aatctgcaaa  1020
ggtctattca ccgccatcaa cctcgggctg aagaaggaac ccaatgtggc tcgcgtgggc  1080
tccgtggcca tcaagctgtg caatctgctg aagatagcac cacctgccgt gtgccaatcc  1140
attgtccacc tctttgagga tgacatggtg gaggtgtgga gacgctcagt gctgagccca  1200
tctgaggcct gtggcctgct cctgggctcc acctgtgggc actgggacat tttctcatct  1260
tggaacatct ctttgcctac tgtgccgaag ccgcccccca aaccccctag cccccccagcc  1320
```

```
ccaggtgccc ctgtcagccg catcctcttc ctcactgacc tgcactggga tcatgactac   1380
ctggagggca cggaccctga ctgtgcagac ccactgtgct gccgcgggg ttctggcctg   1440
ccgcccgcat cccggccagg tgccggatac tggggcgaat acagcaagtg tgacctgccc   1500
ctgaggaccc tggagagcct gttgagtggg ctgggcccag ccggcccttt tgatatggtg   1560
tactggacag gagacatccc cgcacatgat gtctggcaca agactcgtca ggaccaactg   1620
cgggccctga ccaccgtcac agcacttgtg aggaagttcc tggggccagt gccagtgtac   1680
cctgctgtgg gtaaccatga aagcacacct gtcaatagct ccctcccccc cttcattgag   1740
ggcaaccact cctcccgctg gctctatgaa gcgatggcca aggcttggga gccctggctg   1800
cctgccgaag ccctgcgcac cctcagaatt gggggttct atgctctttc cccatacccc   1860
ggtctccgcc tcatctctct caatatgaat ttttgttccc gtgagaactt ctggctcttg   1920
atcaactcca cggatcccgc aggacagctc cagtggctgg tggggagct tcaggctgct   1980
gaggatcgag gagacaaagt gcatataatt ggccacattc ccagggca ctgtctgaag   2040
agctggagct ggaattatta ccgaattgta gccaggtatg agaacaccct ggctgctcag   2100
ttcttttggcc acactcatgt ggatgaattt gaggtcttct atgatgaaga gactctgagc   2160
cggccgctgg ctgtagcctt cctggcaccc agtgcaacta cctacatcgg ccttaatcct   2220
ggttaccgtg tgtaccaaat agatggaaac tactccggga gctctcacgt ggtcctggac   2280
catgagacct acatcctgaa tctgacccag gcaaacatac cggagccat accgcactgg   2340
cagcttctct acagggctcg agaaacctat gggctgccca acacactgcc taccgcctgg   2400
cacaacctgg tatatcgcat gcggggcgac atgcaacttt tccagacctt ctggtttctc   2460
taccataagg gccacccacc ctcggagccc tgtggcacgc cctgccgtct ggctactctt   2520
tgtgcccagc tctctgcccg tgctgacagc cctgctctgt gccgccacct gatgccagat   2580
gggagcctcc cagaggccca gagcctgtgg ccaaggccac tgttttgcta g           2631

SEQ ID NO: 5              moltype = DNA   length = 2226
FEATURE                   Location/Qualifiers
misc_feature              1..2226
                          note = cDNA sequence of the expression cassette for human
                          ASM with five tandem-repeats of the 2gamma3
                          ICAM-1-targeting peptide at the carboxyl terminus
source                    1..2226
                          mol_type = other DNA
                          organism = synthetic construct
SEQUENCE: 5
atggagaccg acacactgct cctgtgggtc ctgctcctct gggtgccagg aagtacagga    60
gatccaccatc accatcacca cgacgacgac gacaagcacc tctttctcc ccaaggccat   120
cctgccaggt tacatcgcat agtgccccgg ctccgagatg tctttgggtg ggggaacctc   180
acctgcccaa tctgcaaagg tctattcacc gccatcaacc tcgggctgaa gaggaaccc    240
aatgtggctc gcgtgggctc cgtggccatc aagctgtgca atctgctgaa gatagccaca   300
cctgccgtgt gccaatccat tgtccacctc tttgaggatg acatgctgga ggtgtggaga   360
cgctcagtgc tgagcccatc tgaggcctgt ggcctgctcc tgggctccac ctgtgggcac   420
tgggacattt tctcatcttg gaacatctct ttgcctactg tgccgaagcc gcccccaaa    480
cccctagcc ccccagcccc aggtgcccct gtcagccga tcctcttcct cactgacctg    540
cactggatc atgactacct ggagggcacg gaccctgact gtgcagacc actgtgctgc    600
cgccggggtt ctggcctgcc gcccgcatcc cggccaggtg ccggatactg ggcgaatac    660
agcaagtgtg acctgcccct gaggaccctg gagagcctgt tgagtgggct gggcccagcc   720
ggcccttttg atatggtgta ctggacagga gacatcccg cacatgatgt ctggcaccag    780
actcgtcagg accaactgcg ggccctgacc accgtcacag cacttgtgag gaagttcctg   840
gggccagtgc cagtgtaccc tgctgtgggt aaccatgaaa gcacacctgt caatagcttc   900
cctccccct tcattgaggg caaccactcc tcccgctggc tctatgaagc gatgccaag    960
gcttgggagc cctggctgcc tgccgaagcc ctgcgcaccc tcagaattgg ggggttctat  1020
gctctttccc catacccccgg tctccgcctc atctctctca atatgaattt tgttccccgt  1080
gagaacttct ggctcttgat caactccacg gatcccgcag gacagctcca gtggctggtg  1140
ggggagcttc aggctgctga ggatcgagga gacaaagtgc atataattgg ccacattccc  1200
cagggcact gtctgaagag ctggagctgg aattattacc gaattgtagc caggtatgag  1260
aacaccctgg ctgctcagtt cttttggcca cactcatgtg atgaatttga ggtcttctat  1320
gatgaagaga ctctgagccg gccgctggct gtagccttcc tggcacccag tgcaactacc  1380
tacatcggcc ttaatcctgg ttaccgtgtg taccaaatag atggaaacta ctccgggagc  1440
tctcacgtgt cctggaccat gagacctaca tcctgaatc tgacccaggc aaacataccg  1500
ggagccatac cgcactggca gcttctctac agggctcgag aaacctatgg gctgcccaac  1560
acactgccta ccgcctggca caacctggta tatcgcatgc ggggcgacat gcaactttc  1620
cagaccttct ggtttctcta ccataagggc cacccaccct cggagcctg tggcacgcc    1680
tgccgtctgc tactctttg tgcccagctc tctgcccgtg ctgacagccc tgctctgtgc  1740
cgccacctga tgccagatgg gagcctccca gaggcccaga gcctgtggcc aaggccactg  1800
ttttgcggat ttctgggagg cggaggagga tccggaagga taaccaaaag              1860
attgtgaata tcaaagagaa agtggctcag attgaggctg gaggcggagg aagcggcggc   1920
ggaggaagca ataatcagaa aatcgtcaac attaaggaaa aggtcgccca gattgaagca   1980
ggaggcggcg gcagcggcgg aggcggaagc aataatcaga gattgttaa catcaaagaa   2040
aaggtggccc aaattgaagc aggaggagga ggatctggag gcgaggcag caataaccag   2100
aagatcgtca acatcaagga aaaggtggct cagatcgagg caggaggcgg aggaagcgga   2160
gggggcggct ctaacaacca gaaaatcgtg aacatcaaag agaaagtggc tcagatcgaa   2220
gcctag                                                               2226

SEQ ID NO: 6              moltype = DNA   length = 1809
FEATURE                   Location/Qualifiers
misc_feature              1..1809
                          note = cDNA sequence of the expression cassette for human
                          ASM control
source                    1..1809
                          mol_type = other DNA
```

```
                        organism = synthetic construct
SEQUENCE: 6
atggagaccg acacactgct cctgtgggtc ctgctcctct gggtgccagg aagtacagga    60
gatcaccatc accatcacca cgacgacgac gacaagcacc ctctttctcc ccaaggccat   120
cctgccaggt tacatcgcat agtgcccggg ctccgagatg tctttgggtg ggggaacctc   180
acctgcccaa tctgcaaagg tctattcacc gccatcaacc tcgggctgaa gaaggaaccc   240
aatgtggctc gcgtgggctc cgtggccatc aagctgtgca atctgctgaa gatagccaca   300
cctgccgtgt gccaatccat tgtccacctc tttgaggatg acatggtgga ggtgtggaga   360
cgctcagtgc tgagcccatc tgaggcctgt ggcctgctcc tgggctccac ctgtgggcac   420
tgggacattt tctcatcttg gaacatctct ttgcctactg tgccgaagcc gccccccaaa   480
ccccctagcc ccccagcccc aggtgcccct gtcagccgca tcctcttcct cactgacctg   540
cactgggatc atgactacct ggagggcacg gaccctgact gtgcagaccc actgtgctgc   600
cgccggggtt ctggcctgcc gcccgcatcc cggccaggtc ccggatactg gggcgaatac   660
agcaagtgtg acctgcccct gaggacccty tgagtgggct gggcccagcc                720
ggcccttttg atatggtgta ctggacagga gacatccccg cacatgatgt ctggcaccag   780
actcgtcagg accaactgcg ggccctgacc accgtcacag cacttgtgag gaagttcctg   840
gggccagtgc cagtgtaccc tgctgtgggt aaccatgaaa gcacacctgt caatagcttc   900
cctcccccct tcattgaggg caaccactcc tcccgctggc tctatgaagc gatggccaag   960
gcttgggagc cctggctgcc tgccgaagcc ctgcgcaccc tcagaattgg ggggttctat  1020
gctctttccc cataccccgg tctccgcctc atctctctca atatgaattt tgttcccgt   1080
gagaacttct ggctcttgat caactccacg gatcccgcag acagctcca gtggctggt   1140
ggggacgttc aggctgctga ggatcgagga gacaaagtgc atataattgg ccacattccc  1200
ccagggcact gtctgaagag ctggagctgg aattattacc gaattgtagc caggtatgag  1260
aacaccctgg ctgctcagtt cttttggcca actcatgtgg atgaatttga ggtcttctat  1320
gatgaagaga ctctgagccg gccgctggct gtagccttcc tggcacccag tgcaactacc  1380
tacatcggcc ttaatcctgg ttaccgtgtg taccaaatag atggaaacta ctccgggagc  1440
tctcacgtgg tcctggacca tgagacctac atcctgaatc tgacccaggc aaacataccg  1500
ggagccatac cgcactggca gcttctctac agggctcgag aaacctatgg gctgcccaac  1560
acactgccta ccgcctggca aacctggta tatcgcatgc ggggcgacat gcaacttttc  1620
cagaccttct ggtttctcta ccataagggc caccacccct ccgagccctg tggcacgccc  1680
tgccgtctgg ctactctttg tgcccagctc tctgcccgtg ctgacagccc tgctctgtgc  1740
cgccacctga tgccagatgg gagcctccca gaggcccaga gcctgtggcc aaggcactg   1800
ttttgctag                                                          1809

SEQ ID NO: 7            moltype = DNA  length = 1383
FEATURE                 Location/Qualifiers
misc_feature            1..1383
                        note = cDNA sequence of the expression cassette for human
                        alpha galactosidase (?Gal) with one copy of the 2gamma3
                        ICAM-1-targeting peptide at the amino terminus
source                  1..1383
                        mol_type = other DNA
                        organism = synthetic construct
SEQUENCE: 7
atgggctggt cctgcatcat tctgtttctg gtgctaccg ccaccggcgt gcactctgat     60
caccaccacc atcaccacga cgatgacgac aagaacaacc agaagatcgt caacatcaaa   120
gagaaggtcg cccagatcga ggctggaggc ggaggatcga gtggtggcgg atctggattc   180
cttggcctgg acaacggcct ggctagaacc cctaccatgg gatggctgca ctggagagag   240
ttcatgtgca acctggactg ccaagaggaa cccgactcct gcatctccga aagctgttc    300
atggaaatgg ccgagctgat ggtgtccgaa ggctggaagg atgccggcta cgagtacctg   360
tgcatcgacg actgttggat ggcccctcag agagactctg agggcagact gcaggccgac   420
cctcagagat tccccacgg catcagacag ctggccaact acgtgcactc caagggcctg   480
aagctgggca tctatgccga cgtgggcaac aagacctgtg ccggctttcc tggctccttc   540
ggctactacg atatcgacgc ccagaccttc gctgactggg gagtcgatct gctgaagttc   600
gacggctgct actgcgactc cctggaaaat ctggccgagu gctacaagca catgtctctg   660
gccctgaacc ggaccggcag atccatcgtg tatagctgcg agtggcccct gtacatgtgg   720
cccttccaga agcctaacta caccgagatc agacagtact gcaaccactg gcggaacttc   780
gccgacatcg acgatagctg gaagtccatc aagtctatcc tggactggac ctccttcaat   840
caagagcgga tcgtggatgt ggctggccct ggcggatgga acgatcctga tatgctggtc   900
atcggcaact tcggcctgtc ctggaaccag caagtgccct gtgggccatt                960
atggccgctc ctctgttcat gtccaacgac ctgagacaca tcagccctca ggccaaggct  1020
ctgctgcagg acaaggatgt gatcgctatc aaccaggatc tctgggcaa gcagggctac   1080
cagttgagac agggcgacaa ctttgaagtg tgggaaagac cctgtccgg cctggcatgg   1140
gctgtcgtca tgatcaacag acaagagatc ggcggaccc ggtcctacaa aatcgctgh    1200
gcttctctcg gcaaaggcgt ggcctgcaat cctgcctgtt tcatcacaca gctgctgccc  1260
gtgaagagaa agctgggctt tacgagtgg acctctcggc tgcggtccca tcaatcct    1320
accggaacag tgctgctgca gctggaaaac catgcagaa tgtccctgaa ggacctgctg   1380
tga                                                                1383

SEQ ID NO: 8            moltype = DNA  length = 1707
FEATURE                 Location/Qualifiers
misc_feature            1..1707
                        note = cDNA sequence of the expression cassette for human
                        ?Gal with five tandem-repeats of the 2?3 ICAM-1-targeting
                        peptide at the carboxyl terminus
source                  1..1707
                        mol_type = other DNA
                        organism = synthetic construct
SEQUENCE: 8
```

```
atgggctggt cctgcatcat tctgtttctg gtggctaccg ccaccggcgt gcactctgat    60
caccaccacc atcaccacga cgatgacgac aagctggaca acggcctggc tagaacccct   120
accatgggat ggctgcactg ggagagattc atgtgcaacc tggactgcca agaggaaccc   180
gactcctgca tctccgagaa gctgttcatg gaaatggccg agctgatggt gtccgaaggc   240
tggaaggatg ccggctacga gtacctgtgc atcgacgact gttggatggc ccctcagaga   300
gactctgagg gcagactgca ggccgatcct cagagatttc cccacggcat cagacagctg   360
gccaactacg tgcactccaa gggcctgaag ctgggcatct atgccgacgt gggcaacaag   420
acctgtgccg gctttcctgg ctccttcggc tactacgata tcgacgccca gaccttcgct   480
gactggggag tcgatctgct gaagttcgac ggctgctact gcgactccct ggaaaatctg   540
gccgacggct acaagcacat gtctctggcc ctgaaccgga ccggcagatc catcgtgtat   600
agctgcgagt ggcccctgta catgtggccc ttccagaagc ctaactacac cgagatcaga   660
cagtactgca accactggcg gaacttcgcc gacatcgacg atagctggaa gtccatcaag   720
tctatcctgg actggacctc cttcaatcaa gagcggatcg tggatgtggc tggccctggc   780
ggatggaacg atcctgatat gctggtcatc ggcaacttcg gcctgtcctg gaaccagcaa   840
gtgacccaga tggccctgtg ggccattatg gccgctcctc tgttcatgtc caacgacctg   900
agacacatca gccctcaggc caaggctctg ctgcaggaca aggatgtgat cgctatcaac   960
caggatcctc tgggcaagca gggctaccag ttgagacagg cgacaacttt gaagtgtgg   1020
gaaagacccc tgtccggcct ggcatgggct gtcgccatga tcaacagaca agagatcggc  1080
ggaccccggt cctacacaat cgctgttgct tctctcggca aaggcgtggc ctgcaatcct  1140
gcctgtttca tcacacagct gctgcccgtg aagagaaagc tgggcttta cgagtggacc  1200
tctcggctgc ggtcccacat caatcctacc ggaacagtgc tgctgcagct ggaaaacacc  1260
atgcagatgt ccctgaagga cctgctggga ttccttgcgg gaggcggagg atctggtggt  1320
ggcggatcta acaaccagaa gatcgtcaac atcaaagaa aggtcgccca gatcgaggct  1380
ggcggcggtg atcaggtgg cggaggaagc aacaatcaga aaattgtgaa tatcaaagaa  1440
aaagtggctc agattgaagc aggcggcgga ggtagcggag tggtggctc taacaatcaa  1500
aaaatcgtta acatcaaaga gaaagttgct caaatccgga ccggcggtgg tggttctgac  1560
ggtggtggta gtaacaatca aaagatcgtc aatatcaaag aaaaggtggc acaaatcgag  1620
gcaggcggag gcggctctgg cggcggagga tcaaacaatc agaagatcgt taacatcaaa  1680
gaaaagtgg cccaaattga ggcctga                                      1707

SEQ ID NO: 9            moltype = DNA   length = 1290
FEATURE                 Location/Qualifiers
misc_feature            1..1290
                        note = cDNA sequence of the expression cassette for human
                        ?Gal control
source                  1..1290
                        mol_type = other DNA
                        organism = synthetic construct
SEQUENCE: 9
atgggctggt cctgcatcat tctgtttctg gtggctaccg ccaccggcgt gcactctgat    60
caccaccacc atcaccacga cgatgacgac aagctggaca acggcctggc tagaacccct   120
accatgggat ggctgcactg ggagagattc atgtgcaacc tggactgcca agaggaaccc   180
gactcctgca tctccgagaa gctgttcatg gaaatggccg agctgatggt gtccgaaggc   240
tggaaggatg ccggctacga gtacctgtgc atcgacgact gttggatggc ccctcagaga   300
gactctgagg gcagactgca ggccgatcct cagagatttc cccacggcat cagacagctg   360
gccaactacg tgcactccaa gggcctgaag ctgggcatct atgccgacgt gggcaacaag   420
acctgtgccg gctttcctgg ctccttcggc tactacgata tcgacgccca gaccttcgct   480
gactggggag tcgatctgct gaagttcgac ggctgctact gcgactccct ggaaaatctg   540
gccgacggct acaagcacat gtctctggcc ctgaaccgga ccggcagatc catcgtgtat   600
agctgcgagt ggcccctgta catgtggccc ttccagaagc ctaactacac cgagatcaga   660
cagtactgca accactggcg gaacttcgcc gacatcgacg atagctggaa gtccatcaag   720
tctatcctgg actggacctc cttcaatcaa gagcggatcg tggatgtggc tggccctggc   780
ggatggaacg atcctgatat gctggtcatc ggcaacttcg gcctgtcctg gaaccagcaa   840
gtgacccaga tggccctgtg ggccattatg gccgctcctc tgttcatgtc caacgacctg   900
agacacatca gccctcaggc caaggctctg ctgcaggaca aggatgtgat cgctatcaac   960
caggatcctc tgggcaagca gggctaccag ttgagacagg cgacaacttt gaagtgtgg   1020
gaaagacccc tgtccggcct ggcatgggct gtcgccatga tcaacagaca agagatcggc  1080
ggaccccggt cctacacaat cgctgttgct tctctcggca aaggcgtggc ctgcaatcct  1140
gcctgtttca tcacacagct gctgcccgtg aagagaaagc tgggcttta cgagtggacc  1200
tctcggctgc ggtcccacat caatcctacc ggaacagtgc tgctgcagct ggaaaacacc  1260
atgcagatgt ccctgaagga cctgctgtga                                   1290

SEQ ID NO: 10           moltype = DNA   length = 1680
FEATURE                 Location/Qualifiers
misc_feature            1..1680
                        note = cDNA sequence of the expression cassette for human
                        glucocerebrosidase (GCase) with one copy of the 2gamma
                        ICAM-1-targeting peptide at the amino terminus
source                  1..1680
                        mol_type = other DNA
                        organism = synthetic construct
SEQUENCE: 10
atgggctggt cctgcatcat tctgtttctg gtggctaccg ccaccggcgt gcactctgat    60
caccaccacc atcaccacga cgatgacgac aagaacagaa agaagatcgt caacatcaaa   120
gagaaggtcg cccagatcga ggctggcggc ggaggatctg gcggaggcgg atctggattt   180
ttgggagcca gccttgcat ccccaagtcc ttcggctact ctctctgtcgt gtgcgtgtgc   240
aacgccacct actgcgacag cttcgaccct ctaccttc tgctctgggg cacattctcc   300
agatacgagt ccaccagatc cggcagacgg atggaactga gcatgggccc tatccaggct   360
aaccataccg gcacaggact gctgctgaca ctgcagccg agcagaaatt ccagaaagtg   420
```

```
aaaggcttcg gcggagccat gaccgatgcc gccgctctga atattctggc tctgagccct  480
cctgctcaga acctgctgct caagtcctac ttctccgagg aaggcatcgg ctacaacatc  540
atccgggtgc caatggcctc ctgcgacttc tctatccgga cctacaccta cgctgacacc  600
cctgacgatt tccagctgca aacttcagc ctgcctgaag aggacaccaa gctgaagatc  660
cctctgatcc acagagccct gcagctggct cagaggcctg tttctctgct ggcctctcct  720
tggacctctc caacctggct gaaaacaaat ggcgccgtga acggcaaggg ctccctgaaa  780
ggacaacccg gcgatatcta ccaccagacc tgggccagat acttcgtgaa gttcctggac  840
gcctacgcca agcacaagct gcagtttgg gctgtgaccg ccgagaacga gccttctgct  900
ggactgctgt ctggctaccc tttccagtgc ctgggctta cccctgagca ccagagagac  960
tttatcgcca gagatctggg ccccacactg gccaattcta cccaccataa tgtgcggctg  1020
ctgatgctgg acgaccagag actgctgttg ccccactggg ctaaagtggt gctgaccgat  1080
cctgaggccg ccaaatacgt gcacggaatc gccgtgcact ggtatctgga ctttctggcc  1140
cctgccaagg ctaccctggg cgagacacat agactgttcc ccaacaccat gctgttcgcc  1200
tctgaggcct gtgtgggctc caagttctgg gagcagtctg tgcgactggt gcttgggat  1260
agaggcatgc agtactccca ctccatcatc accaacctgc tgtaccacgt cgtcggctgg  1320
accgattgga acctggcact gaatcctgaa ggcggcccta actgggtccg aaacttcgtg  1380
gactcccta tcatcgtgga catcaccaag gacaccttct acaagcagcc catgttctac  1440
catctgggcc acttcagcaa gttcatcccc gagggctcg agagagtcgg cctggttgcc  1500
tctcagaaga acgacctgga cgctgtggct ctgatgcacc ctgatggatc tgctgtggtg  1560
gtcgtgctga accggtcctc caaagatgtg ccctgacca tcaaggatcc cgccgtggga  1620
ttcctggaaa ccatctctcc tggctactcc atccacacct acctgtggcg tagacagtga  1680

SEQ ID NO: 11         moltype = DNA   length = 2004
FEATURE               Location/Qualifiers
misc_feature          1..2004
                      note = cDNA sequence of the expression cassette for human
                       GCase with five tandem-repeats of the 2?gamma
                       ICAM-1-targeting peptide at the amino terminus
source                1..2004
                      mol_type = other DNA
                      organism = synthetic construct
SEQUENCE: 11
atgggctggt cctgcatcat tctgtttctg gtggctaccg ccaccggcgt gcactctgat  60
caccaccacc atcaccacga cgatgacgac aagaacaacc agaagatcgt caatcatcaaa  120
gagaaggtcg cccagatcga ggctggcggc ggaggatctg gcggaggcgg atctaacaat  180
cagaaaattg tgaatatcaa agaaaaagtg gctcagattg aagccggcgg tggtggtagc  240
ggtggcggag aagtaacaa tcaaaagatc gtgaacatca agaaaaagt tgcacaaatc  300
gaggcaggcg gtggcggcag cggaggtggt ggatccaaca accagaaaat cgtgaacatc  360
aaagaaaaagg tggcccaaat cgaagccggc ggaggcggt caggcggcgg aggttcaaac  420
aatcagaaga tcgttaatat caaagaaaag gttgcccaga ttgaggcagg cggaggtgga  480
agcggcggag gcggctctgg atttttggga gccagacctt gcatcccaa gtccttcggc  540
tactcctctg tcgtgtgcgt gtgcaacgcc acctactgcg acagcttcga cctcctacc  600
tttcctgctc tgggcacatt ctccagatac gagtccacca gatcggcag acggatggaa  660
ctgagcatgg gccctatcca ggctaaccat accggcacag gactgctgct gacactgcag  720
cccgagcaga aattccagaa agtgaaaggc ttcggcggag ccatgaccga tgccgccgct  780
ctgaatattc tggctctgag ccctcctgct cagaacctgc tgtcaagtc ctacttctcc  840
gaggaaggca tcggctacaa catcatccgg gtgcaatgg cctcctgcga cttctctatc  900
cggacctaca cctacgctga cacccctgac gatttccagc tgcacaactt cagcctgcct  960
gaagaggaca ccaagctgaa gatccctctg atccacagag ccctgcagct ggctcagagg  1020
cctgtttctc tgctggcctc tccttggacc tctccaacct ggctgaaaac aaatggcgcc  1080
gtgaacggca agggctccct gaaaggacaa cccggcgata tctaccacca gacctaccaca  1140
agatacttcg tgaagttcct ggacgcctac gccgagcaca agctgcagtt tggctgtgt  1200
accgccgaga acgagccttc tgctggactg ctgtctggct accctttcca gtgcctgggc  1260
tttaccctg agcaccagag agactttatc gccagagatc tgggccccac actgccaat  1320
tctacccacc ataatgtgcg gctgctgatg ctggacgacc agagactgct gttgccccac  1380
tgggctaaag tggtgctgac cgatcctgag gccgccaaat acgtgcacgg aatcgccgtg  1440
cactggtatc tggactttct ggcccctgcc aaggctaccc tgggcgagac acatagactg  1500
ttccccaaca ccatgctgtt cgcctctgag gcctgtgtgg gctccaagtt ctgggagcag  1560
tctgtgcgac tcggtcttg gataagggc atgcagtact cccactccat catcaccaac  1620
ctgctgtacc acgtcgtcgg ctggaccgat tggaacctgg cactgaatcc tgaaggcggc  1680
cctaactggg tccgaaactt cgtggactcc ctatcatcg tggacatcac caaggacacc  1740
ttctacaagc agcccatgtt ctaccatctg gccacttca gcaagttcat ccccgagggc  1800
tctcagagag tcggcctggt tgcctctcag aagaacgacc tggacgctgt ggctctgatg  1860
caccctgatg gatctgctgt ggtggtcgtg ctgaaccggt cctccaaaga tgtgccctg  1920
accatcaagg atcccgccgt gggattcctg gaaaccatct ccctggcta ctccatccac  1980
acctacctgt ggcgtagaca gtga                                        2004

SEQ ID NO: 12         moltype = DNA   length = 1290
FEATURE               Location/Qualifiers
misc_feature          1..1290
                      note = cDNA sequence of the expression cassette for human
                       GCase control
source                1..1290
                      mol_type = other DNA
                      organism = synthetic construct
SEQUENCE: 12
atgggctggt cctgcatcat tctgtttctg gtggctaccg ccaccggcgt gcactctgat  60
caccaccacc atcaccacga cgatgacgac aagctggaca cggcctggc tagaaccct  120
accatgggat ggctgcactg ggagagattc atgtgcaacc tggactgcca agaggaaccc  180
```

-continued

```
gactcctgca tctccgagaa gctgttcatg gaaatggccg agctgatggt gtccgaaggc  240
tggaaggatg ccggctacga gtacctgtgc atcgacgact gttggatggc ccctcagaga  300
gactctgagg gcagactgca ggccgatcct cagagatttc cccacggcat cagacagctg  360
gccaactacg tgcactccaa gggcctgaag ctgggcatct atgccgacgt gggcaacaag  420
acctgtgccg gctttcctgg ctccttcggc tactacgata tcgacgccca gaccttcgct  480
gactggggag tcgatctgct gaagttcgac ggctgctact gcgactccct ggaaaatctg  540
gccgacggct acaagcacat gtctctggcc ctgaaccgga ccggcagatc catcgtgtat  600
agctgcgagt ggcccctgta catgtggccc ttccagaagc ctaactacac cgagatcaga  660
cagtactgca accactggcg gaacttcgcc gacatcgacg atagctggaa gtccatcaag  720
tctatcctgg actggacctc cttcaatcaa gagcggatcg tggatgtggc tggccctggc  780
ggatggaacg atcctgatat gctggtcatc ggcaacttcg gcctgtcctg gaaccagcaa  840
gtgacccaga tggccctgtg ggccattatg gccgctcctc tgttcatgtc caacgacctg  900
agacacatca gccctcaggc caaggctctg ctgcaggaca aggatgtgat cgctatcaac  960
caggatcctc tgggcaagca gggctaccag ttgagacagg gcgacaactt tgaagtgtgg  1020
gaaagacccc tgtccggcct ggcatgggct gtcgccatga tcaacagaca agagatcggc  1080
ggaccccggt cctacacaat cgctgttgct tctctcggca aaggcgtggc ctgcaatcct  1140
gcctgtttca tcacacagct gctgcccgtg aagagaaagc tgggctttta cgagtggacc  1200
tctcggctgc ggtcccacat caatcctacc ggaacagtgc tgctgcagct ggaaaacacc  1260
atgcagatgt ccctgaagga cctgctgtga                                  1290

SEQ ID NO: 13          moltype = AA  length = 633
FEATURE                Location/Qualifiers
REGION                 1..633
                       note = Amino acid sequence of the expression cassette for
                        human acid sphingomyelinase (ASM) with one copy of the
                        2gamma3 ICAM-1-targeting peptide at the amino terminus
source                 1..633
                       mol_type = protein
                       organism = synthetic construct
SEQUENCE: 13
METDTLLLWV LLLWVPGSTG DHHHHHHDDD DKNNQKIVNI KEKVAQIEAG GGGSGGGGSG  60
FLGHPLSPQG HPARLHRIVP RLRDVFGWGN LTCPICKGLF TAINLGLKKE PNVARVGSVA  120
IKLCNLLKIA PPAVCQSIVH LFEDDMVEVW RRSVLSPSEA CGLLLGSTCG HWDIFSSWNI  180
SLPTVPKPPP KPPSPPAPGA PVSRILFLTD LHWDHDYLEG TDPDCADPLC CRRGSGLPPA  240
SRPGAGYWGE YSKCDLPLRT LESLLSGLGP AGPFDMVYWT GDIPAHDVWH QTRQDQLRAL  300
TTVTALVRKF LGPVPVYPAV GNHESTPVNS FPPPFIEGNH SSRWLYEAMA KAWEPWLPAE  360
ALRTLRIGGF YALSPYPGLR LISLNMNFCS RENFWLLINS TDPAGQLQWL VGELQAAEDR  420
GDKVHIIGHI PPGHCLKSWS WNYYRIVARY ENTLAAQFFG HTHVDEFEVF YDEETLSRPL  480
AVAFLAPSAT TYIGLNPGYR VYQIDGNYSG SSHVVLDHET YILNLTQANI PGAIPHWQLL  540
YRARETYGLP NTLPTAWHNL VYRMRGDMQL FQTFWFLYHK GHPPSEPCGT PCRLATLCAQ  600
LSARADSPAL CRHLMPDGSL PEAQSLWPRP LFC                              633

SEQ ID NO: 14          moltype = AA  length = 741
FEATURE                Location/Qualifiers
REGION                 1..741
                       note = Amino acid sequence of the expression cassette for
                        human ASM with five tandem-repeats of the 2?gamma
                        ICAM-1-targeting peptide at the amino terminus
source                 1..741
                       mol_type = protein
                       organism = synthetic construct
SEQUENCE: 14
METDTLLLWV LLLWVPGSTG DHHHHHHDDD DKNNQKIVNI KEKVAQIEAG GGGSGGGGSN  60
NQKIVNIKEK VAQIEAGGGG SGGGGSNNQK IVNIKEKVAQ IEAGGGGSGG GGSNNQKIVN  120
IKEKVAQIEA GGGGSGGGGS NNQKIVNIKE KVAQIEAGGG GSGGGGSGFL GHPLSPQGHP  180
ARLHRIVPRL RDVFGWGNLT CPICKGLFTA INLGLKKEPN VARVGSVAIK LCNLLKIAPP  240
AVCQSIVHLF EDDMVEVWRR SVLSPSEACG LLLGSTCGHW DIFSSWNISL PTVPKPPPKP  300
PSPPAPGAPV SRILFLTDLH WDHDYLEGTD PDCADPLCCR RGSGLPPASR PGAGYWGEYS  360
KCDLPLRTLE SLLSGLGPAG PFDMVYWTGD IPAHDVWHQT RQDQLRALTT VTALVRKFLG  420
PVPVYPAVGN HESTPVNSFP PPFIEGNHSS RWLYEAMAKA WEPWLPAEAL RTLRIGGFYA  480
LSPYPGLRLI SLNMNFCSRE NFWLLINSTD PAGQLQWLVG ELQAAEDRGD KVHIIGHIPP  540
GHCLKSWSWN YYRIVARYEN TLAAQFFGHT HVDEFEVFYD EETLSRPLAV AFLAPSATTY  600
IGLNPGYRVY QIDGNYSGSS HVVLDHETYI LNLTQANIPG AIPHWQLLYR ARETYGLPNT  660
LPTAWHNLVY RMRGDMQLFQ TFWFLYHKGH PPSEPCGTPC RLATLCAQLS ARADSPALCR  720
HLMPDGSLPE AQSLWPRPLF C                                           741

SEQ ID NO: 15          moltype = AA  length = 876
FEATURE                Location/Qualifiers
REGION                 1..876
                       note = Amino acid sequence of the expression cassette for
                        human ASM with ten tandem-repeats of the 2gamma3
                        ICAM-1-targeting peptide at the amino terminus
source                 1..876
                       mol_type = protein
                       organism = synthetic construct
SEQUENCE: 15
METDTLLLWV LLLWVPGSTG DHHHHHHDDD DKNNQKIVNI KEKVAQIEAG GGGSGGGGSN  60
NQKIVNIKEK VAQIEAGGGG SGGGGSNNQK IVNIKEKVAQ IEAGGGGSGG GGSNNQKIVN  120
IKEKVAQIEA GGGGSGGGGS NNQKIVNIKE KVAQIEAGGG GSGGGGSNNQ KIVNIKEKVA  180
```

-continued

```
QIEAGGGGSG GGGSNNQKIV NIKEKVAQIE AGGGGSGGGG SNNQKIVNIK EKVAQIEAGG  240
GGSGGGGSNN QKIVNIKEKV AQIEAGGGGS GGGGSNNQKI VNIKEKVAQI EAGGGGSGGG  300
GSGFLGHPLS PQGHPARLHR IVPRLRDVFG WGNLTCPICK GLFTAINLGL KKEPNVARVG  360
SVAIKLCNLL KIAPPAVCQS IVHLFEDDMV EVWRRSVLSP SEACGLLLGS TCGHWDIFSS  420
WNISLPTVPK PPPKPPSPPA PGAPVSRILF LTDLHWDHDY LEGTDPDCAD PLCCRRGSGL  480
PPASRPGAGY WGEYSKCDLP LRTLESLLSG LGPAGPFDMV YWTGDIPAHD VWHQTRQDQL  540
RALTTVTALV RKFLGPVPVY PAVGNHESTP VNSFPPPFIE GNHSSRWLYE AMAKAWEPWL  600
PAEALRTLRI GGFYALSPYP GLRLISLNMN FCSRENFWLL INSTDPAGQL QWLVGELQAA  660
EDRGDKVHII GHIPPGHCLK SWSWNYYRIV ARYENTLAAQ FFGHTHVDEF EVFYDEETLS  720
RPLAVAFLAP SATTYIGLNP GYRVYQIDGN YSGSSHVVLD HETYILNLTQ ANIPGAIPHW  780
QLLYRARETY GLPNTLPTAW HNLVYRMRGD MQLFQTFWFL YHKGHPPSEP CGTPCRLATL  840
CAQLSARADS PALCRHLMPD GSLPEAQSLW PRPLFC                            876

SEQ ID NO: 16          moltype = AA  length = 741
FEATURE                Location/Qualifiers
REGION                 1..741
                       note = Amino acid sequence of the expression cassette for
                        human ASM with five tandem-repeats of the 2?gamma
                        ICAM-1-targeting peptide at the carboxyl terminus
source                 1..741
                       mol_type = protein
                       organism = synthetic construct
SEQUENCE: 16
METDTLLLWV LLLWVPGSTG DHHHHHHDDD DKHPLSPQGH PARLHRIVPR LRDVFGWGNL  60
TCPICKGLFT AINLGLKKEP NVARVGSVAI KLCNLLKIAP PAVCQSIVHL FEDDMVEVWR  120
RSVLSPSEAC GLLLGSTCGH WDIFSSWNIS LPTVPKPPPK PPSPPAPGAP VSRILFLTDL  180
HWDHDYLEGT DPDCADPLCC RRGSGLPPAS RPGAGYWGEY SKCDLPLRTL ESLLSGLGPA  240
GPFDMVYWTG DIPAHDVWHQ TRQDQLRALT TVTALVRKFL GPVPVYPAVG NHESTPVNSF  300
PPPFIEGNHS SRWLYEAMAK AWEPWLPAEA LRTLRIGGFY ALSPYPGLRL ISLNMNFCSR  360
ENFWLLINST DPAGQLQWLV GELQAAEDRG DKVHIIGHIP PGHCLKSWSW NYYRIVARYE  420
NTLAAQFFGH THVDEFEVFY DEETLSRPLA VAFLAPSATT YIGLNPGYRV YQIDGNYSGS  480
SHVVLDHETY ILNLTQANIP GAIPHWQLLY RARETYGLPN TLPTAWHNLV YRMRGDMQLF  540
QTFWFLYHKG HPPSEPCGTP CRLATLCAQL SARADSPALC RHLMPDGSLP EAQSLWPRPL  600
FCGFLGGGGG SGGGGSNNQK IVNIKEKVAQ IEAGGGGSGG GGSNNQKIVN IKEKVAQIEA  660
GGGGSGGGGS NNQKIVNIKE KVAQIEAGGG GSGGGGSNNQ KIVNIKEKVA QIEAGGGGSG  720
GGGSNNQKIV NIKEKVAQIE A                                            741

SEQ ID NO: 17          moltype = AA  length = 602
FEATURE                Location/Qualifiers
REGION                 1..602
                       note = Amino acid sequence of the expression cassette for
                        human ASM control
source                 1..602
                       mol_type = protein
                       organism = synthetic construct
SEQUENCE: 17
METDTLLLWV LLLWVPGSTG DHHHHHHDDD DKHPLSPQGH PARLHRIVPR LRDVFGWGNL  60
TCPICKGLFT AINLGLKKEP NVARVGSVAI KLCNLLKIAP PAVCQSIVHL FEDDMVEVWR  120
RSVLSPSEAC GLLLGSTCGH WDIFSSWNIS LPTVPKPPPK PPSPPAPGAP VSRILFLTDL  180
HWDHDYLEGT DPDCADPLCC RRGSGLPPAS RPGAGYWGEY SKCDLPLRTL ESLLSGLGPA  240
GPFDMVYWTG DIPAHDVWHQ TRQDQLRALT TVTALVRKFL GPVPVYPAVG NHESTPVNSF  300
PPPFIEGNHS SRWLYEAMAK AWEPWLPAEA LRTLRIGGFY ALSPYPGLRL ISLNMNFCSR  360
ENFWLLINST DPAGQLQWLV GELQAAEDRG DKVHIIGHIP PGHCLKSWSW NYYRIVARYE  420
NTLAAQFFGH THVDEFEVFY DEETLSRPLA VAFLAPSATT YIGLNPGYRV YQIDGNYSGS  480
SHVVLDHETY ILNLTQANIP GAIPHWQLLY RARETYGLPN TLPTAWHNLV YRMRGDMQLF  540
QTFWFLYHKG HPPSEPCGTP CRLATLCAQL SARADSPALC RHLMPDGSLP EAQSLWPRPL  600
FC                                                                 602

SEQ ID NO: 18          moltype = AA  length = 460
FEATURE                Location/Qualifiers
REGION                 1..460
                       note = Amino acid sequence of the expression cassette for
                        human alpha galactosidase with one copy of the 2gamma3
                        ICAM-1-targeting peptide at the amino terminus
source                 1..460
                       mol_type = protein
                       organism = synthetic construct
SEQUENCE: 18
MGWSCIILFL VATATGVHSD HHHHHHDDDD KNNQKIVNIK EKVAQIEAGG GGSGGGGSGF  60
LGLDNGLART PTMGWLHWER FMCNLDCQEE PDSCISEKLF MEMAELMVSE GWKDAGYEYL  120
CIDDCWMAPQ RDSEGRLQAD PQRFPHGIRQ LANYVHSKGL KLGIYADVGN KTCAGFPGSF  180
GYYDIDAQTF ADWGVDLLKF DGCYCDSLEN LADGYKHMSL ALNRTGRSIV YSCEWPLYMW  240
PFQKPNYTEI RQYCNHWRNF ADIDDSWKSI KSILDWTSFN QERIVDVAGP GGWNDPDMLV  300
IGNFGLSWNQ QVTQMALWAI MAAPLFMSND LRHISPQAKA LLQDKDVIAI NQDPLGKQGY  360
QLRQGDNFEV WERPLSGLAW AVAMINRQEI GGPRSYTIAV ASLGKGVACN PACFITQLLP  420
VKRKLGFYEW TSRLRSHINP TGTVLLQLEN TMQMSLKDLL                        460

SEQ ID NO: 19          moltype = AA  length = 568
FEATURE                Location/Qualifiers
```

```
REGION                  1..568
                        note = Amino acid sequence of the expression cassette for
                         human alphaGal with five tandem-repeats of the 2beta3
                         ICAM-1-targeting peptide at the carboxyl terminus
source                  1..568
                        mol_type = protein
                        organism = synthetic construct
SEQUENCE: 19
MGWSCIILFL VATATGVHSD HHHHHHDDDD KLDNGLARTP TMGWLHWERF MCNLDCQEEP  60
DSCISEKLFM EMAELMVSEG WKDAGYEYLC IDDCWMAPQR DSEGRLQADP QRFPHGIRQL  120
ANYVHSKGLK LGIYADVGNK TCAGFPGSFG YYDIDAQTFA DWGVDLLKFD GCYCDSLENL  180
ADGYKHMSLA LNRTGRSIVY SCEWPLYMWP FQKPNYTEIR QYCNHWRNFA DIDDSWKSIK  240
SILDWTSFNQ ERIVDVAGPG GWNDPDMLVI GNFGLSWNQQ VTQMALWAIM AAPLFMSNDL  300
RHISPQAKAL LQDKDVIAIN QDPLGKQGYQ LRQGDNFEVW ERPLSGLAWA VAMINRQEIG  360
GPRSYTIAVA SLGKGVACNP ACFITQLLPV KRKLGFYEWT SRLRSHINPT GTVLLQLENT  420
MQMSLKDLLG FLGGGGGSGG GGSNNQKIVN IKEKVAQIEA GGGGSGGGGS NNQKIVNIKE  480
KVAQIEAGGG GSGGGGSNNQ KIVNIKEKVA QIEAGGGGSG GGGSNNQKIV NIKEKVAQIE  540
AGGGGSGGGG SNNQKIVNIK EKVAQIEA                                    568

SEQ ID NO: 20           moltype = AA  length = 429
FEATURE                 Location/Qualifiers
REGION                  1..429
                        note = Amino acid sequence of the expression cassette for
                         human alphaGal control
source                  1..429
                        mol_type = protein
                        organism = synthetic construct
SEQUENCE: 20
MGWSCIILFL VATATGVHSD HHHHHHDDDD KLDNGLARTP TMGWLHWERF MCNLDCQEEP  60
DSCISEKLFM EMAELMVSEG WKDAGYEYLC IDDCWMAPQR DSEGRLQADP QRFPHGIRQL  120
ANYVHSKGLK LGIYADVGNK TCAGFPGSFG YYDIDAQTFA DWGVDLLKFD GCYCDSLENL  180
ADGYKHMSLA LNRTGRSIVY SCEWPLYMWP FQKPNYTEIR QYCNHWRNFA DIDDSWKSIK  240
SILDWTSFNQ ERIVDVAGPG GWNDPDMLVI GNFGLSWNQQ VTQMALWAIM AAPLFMSNDL  300
RHISPQAKAL LQDKDVIAIN QDPLGKQGYQ LRQGDNFEVW ERPLSGLAWA VAMINRQEIG  360
GPRSYTIAVA SLGKGVACNP ACFITQLLPV KRKLGFYEWT SRLRSHINPT GTVLLQLENT  420
MQMSLKDLL                                                         429

SEQ ID NO: 21           moltype = AA  length = 559
FEATURE                 Location/Qualifiers
REGION                  1..559
                        note = Amino acid sequence of the expression cassette for
                         human glucocerebrosidase (GCase) with one copy of the
                         2gamma3 ICAM-1-targeting peptide at the amino terminus
source                  1..559
                        mol_type = protein
                        organism = synthetic construct
SEQUENCE: 21
MGWSCIILFL VATATGVHSD HHHHHHDDDD KNNQKIVNIK EKVAQIEAGG GGSGGGGSGF  60
LGARPCIPKS FGYSSVVCVC NATYCDSFDP PTFPALGTFS RYESTRSGRR MELSMGPIQA  120
NHTGTGLLLT LQPEQKFQKV KGFGGAMTDA AALNILALSP PAQNLLLKSY FSEEGIGYNI  180
IRVPMASCDF SIRTYTYADT PDDFQLHNFS LPEEDTKLKI PLIHRALQLA QRPVSLLASP  240
WTSPTWLKTN GAVNGKGSLK GQPGDIYHQT WARYFVKFLD AYAEHKLQFW AVTAENEPSA  300
GLLSGYPFQC LGFTPEHQRD FIARDLGPTL ANSTHHNVRL LMLDDQRLLL PHWAKVVLTD  360
PEAAKYVHGI AVHWYLDFLA PAKATLGETH RLFPNTMLFA SEACVGSKFW EQSVRLGSWD  420
RGMQYSHSII TNLLYHVVGW TDWNLALNPE GGPNWVRNFV DSPIIVDITK DTFYKQPMFY  480
HLGHFSKFIP EGSQRVGLVA SQKNDLDAVA LMHPDGSAVV VVLNRSSKDV PLTIKDPAVG  540
FLETISPGYS IHTYLWRRQ                                              559

SEQ ID NO: 22           moltype = AA  length = 667
FEATURE                 Location/Qualifiers
REGION                  1..667
                        note = Amino acid sequence of the expression cassette for
                         human GCase with five tandem-repeats of the 2gamma3
                         ICAM-1-targeting peptide at the amino terminus
source                  1..667
                        mol_type = protein
                        organism = synthetic construct
SEQUENCE: 22
MGWSCIILFL VATATGVHSD HHHHHHDDDD KNNQKIVNIK EKVAQIEAGG GGSGGGGSNN  60
QKIVNIKEKV AQIEAGGGGS GGGGSNNQKI VNIKEKVAQI EAGGGGSGGG GSNNQKIVNI  120
KEKVAQIEAG GGGSGGGGSN NQKIVNIKEK VAQIEAGGGG SGGGGSGFLG ARPCIPKSFG  180
YSSVVCVCNA TYCDSFDPPT FPALGTFSRY ESTRSGRRME LSMGPIQANH TGTGLLLTLQ  240
PEQKFQKVKG FGGAMTDAAA LNILALSPPA QNLLLKSYFS EEGIGYNIIR VPMASCDFSI  300
RTYTYADTPD DFQLHNFSLP EEDTKLKIPL IHRALQLAQR PVSLLASPWT SPTWLKTNGA  360
VNGKGSLKGQ PGDIYHQTWA RYFVKFLDAY AEHKLQFWAV TAENEPSAGL LSGYPFQCLG  420
FTPEHQRDFI ARDLGPTLAN STHHNVRLLM LDDQRLLLPH WAKVVLTDPE AAKYVHGIAV  480
HWYLDFLAPA KATLGETHRL FPNTMLFASE ACVGSKFWEQ SVRLGSWDRG MQYSHSIITN  540
LLYHVVGWTD WNLALNPEGG PNWVRNFVDS PIIVDITKDT FYKQPMFYHL GHFSKFIPEG  600
SQRVGLVASQ KNDLDAVALM HPDGSAVVVV LNRSSKDVPL TIKDPAVGFL ETISPGYSIH  660
```

```
SEQ ID NO: 23          moltype = AA  length = 528
FEATURE                Location/Qualifiers
REGION                 1..528
                       note = Amino acid sequence of the expression cassette for
                        human GCase control
source                 1..528
                       mol_type = protein
                       organism = synthetic construct
SEQUENCE: 23
MGWSCIILFL VATATGVHSD HHHHHHDDDD KARPCIPKSF GYSSVVCVCN ATYCDSFDPP   60
TPPALGTFSR YESTRSGRRM ELSMGPIQAN HTGTGLLLTL QPEQKFQKVK GFGGAMTDAA  120
ALNILALSPP AQNLLLKSYF SEEGIGYNII RVPMASCDFS IRTYTYADTP DDFQLHNFSL  180
PEEDTKLKIP LIHRALQLAQ RPVSLLASPW TSPTWLKTNG AVNGKGSLKG QPGDIYHQTW  240
ARYFVKFLDA YAEHKLQFWA VTAENEPSAG LLSGYPFQCL GFTPEHQRDF IARDLGPTLA  300
NSTHHNVRLL MLDDQRLLLP HWAKVVLTDP EAAKYVHGIA VHWYLDFLAP AKATLGETHR  360
LFPNTMLFAS EACVGSKFWE QSVRLGSWDR GMQYSHSIIT NLLYHVVGWT DWNLALNPEG  420
GPNWVRNFVD SPIIVDITKD TFYKQPMFYH LGHFSKFIPE GSQRVGLVAS QKNDLDAVAL  480
MHPDGSAVVV VLNRSSKDVP LTIKDPAVGF LETISPGYSI HTYLWRRQ              528

SEQ ID NO: 24          moltype = AA  length = 5
FEATURE                Location/Qualifiers
REGION                 1..5
                       note = Amino acid sequence of a glycine-serine linker
source                 1..5
                       mol_type = protein
                       organism = synthetic construct
SEQUENCE: 24
GGGGS                                                               5

SEQ ID NO: 25          moltype = AA  length = 10
FEATURE                Location/Qualifiers
REGION                 1..10
                       note = Amino acid sequence of a two repeats of the
                        glycine-serine linker
source                 1..10
                       mol_type = protein
                       organism = synthetic construct
SEQUENCE: 25
GGGGSGGGGS                                                         10

SEQ ID NO: 26          moltype = AA  length = 17
FEATURE                Location/Qualifiers
REGION                 1..17
                       note = Amino acid sequence of alternative ICAM-1 targeting
                        peptide
source                 1..17
                       mol_type = protein
                       organism = synthetic construct
SEQUENCE: 26
NNQKIVNLKE KVAQLEA                                                 17

SEQ ID NO: 27          moltype = AA  length = 17
FEATURE                Location/Qualifiers
REGION                 1..17
                       note = Amino acid sequence of alternative ICAM-1 targeting
                        peptide
source                 1..17
                       mol_type = protein
                       organism = synthetic construct
SEQUENCE: 27
NNQKLVNIKE KVAQIEA                                                 17

SEQ ID NO: 28          moltype = AA  length = 7
FEATURE                Location/Qualifiers
REGION                 1..7
                       note = Amino acid sequence of alternative ICAM-1 targeting
                        peptide
source                 1..7
                       mol_type = protein
                       organism = synthetic construct
SEQUENCE: 28
YPASYQR                                                             7

SEQ ID NO: 29          moltype = AA  length = 7
FEATURE                Location/Qualifiers
REGION                 1..7
                       note = Amino acid sequence of alternative ICAM-1 targeting
```

```
                        peptide
source                  1..7
                        mol_type = protein
                        organism = synthetic construct
SEQUENCE: 29
YQATPLP                                                                 7

SEQ ID NO: 30           moltype = AA   length = 7
FEATURE                 Location/Qualifiers
REGION                  1..7
                        note = Amino acid sequence of alternative ICAM-1 targeting
                        peptide
source                  1..7
                        mol_type = protein
                        organism = synthetic construct
SEQUENCE: 30
GSLLSAA                                                                 7

SEQ ID NO: 31           moltype = AA   length = 7
FEATURE                 Location/Qualifiers
REGION                  1..7
                        note = Amino acid sequence of alternative ICAM-1 targeting
                        peptide
source                  1..7
                        mol_type = protein
                        organism = synthetic construct
SEQUENCE: 31
FSPHSRT                                                                 7

SEQ ID NO: 32           moltype = AA   length = 7
FEATURE                 Location/Qualifiers
REGION                  1..7
                        note = Amino acid sequence of alternative ICAM-1 targeting
                        peptide
source                  1..7
                        mol_type = protein
                        organism = synthetic construct
SEQUENCE: 32
YPFLPTA                                                                 7

SEQ ID NO: 33           moltype = AA   length = 7
FEATURE                 Location/Qualifiers
REGION                  1..7
                        note = Amino acid sequence of alternative ICAM-1 targeting
                        peptide
source                  1..7
                        mol_type = protein
                        organism = synthetic construct
SEQUENCE: 33
GCKLCAQ                                                                 7

SEQ ID NO: 34           moltype = AA   length = 4
FEATURE                 Location/Qualifiers
REGION                  1..4
                        note = Amino acid sequence of the first protease cleavage
                        site, recognized by cathepsin L or cathepsin B, in the
                        fusion proteins
source                  1..4
                        mol_type = protein
                        organism = synthetic construct
SEQUENCE: 34
GFLG                                                                    4

SEQ ID NO: 35           moltype = AA   length = 5
FEATURE                 Location/Qualifiers
REGION                  1..5
                        note = Amino acid sequence of the second protease cleavage
                        site, the enterokinase cleavage sequence, in the fusion
                        proteins
source                  1..5
                        mol_type = protein
                        organism = synthetic construct
SEQUENCE: 35
DDDDK                                                                   5

SEQ ID NO: 36           moltype = AA   length = 6
FEATURE                 Location/Qualifiers
REGION                  1..6
                        note = Amino acid sequence of the second protease cleavage
```

| | |
|---|---|
| | site, the Tobacco etch virus cleavage sequence, in the fusion proteins |
| source | 1..6<br>mol_type = protein<br>organism = synthetic construct |
| SEQUENCE: 36<br>ENLYFQ | 6 |
| SEQ ID NO: 37<br>FEATURE<br>REGION | moltype = AA  length = 4<br>Location/Qualifiers<br>1..4<br>note = Amino acid sequence of the second protease cleavage site, the Factor Xa cleavage site, in the fusion proteins |
| source | 1..4<br>mol_type = protein<br>organism = synthetic construct |
| SEQUENCE: 37<br>IEGR | 4 |
| SEQ ID NO: 38<br>SEQUENCE: 38<br>000 | moltype =   length = |
| SEQ ID NO: 39<br>SEQUENCE: 39<br>000 | moltype =   length = |
| SEQ ID NO: 40<br>FEATURE<br>REGION | moltype = AA  length = 6<br>Location/Qualifiers<br>1..6<br>note = Amino acid sequence of the second protease cleavage site, the thrombin cleavage site, in the fusion proteins |
| source | 1..6<br>mol_type = protein<br>organism = synthetic construct |
| SEQUENCE: 40<br>LVPRGS | 6 |
| SEQ ID NO: 41<br>FEATURE<br>REGION | moltype = AA  length = 20<br>Location/Qualifiers<br>1..20<br>note = Amino acid sequence of a secretion signal in the fusion protein |
| source | 1..20<br>mol_type = protein<br>organism = synthetic construct |
| SEQUENCE: 41<br>METDTLLLWV LLLWVPGSTG | 20 |
| SEQ ID NO: 42<br>FEATURE<br>REGION | moltype = AA  length = 20<br>Location/Qualifiers<br>1..20<br>note = Amino acid sequence of a secretion signal in the fusion proteins |
| source | 1..20<br>mol_type = protein<br>organism = synthetic construct |
| SEQUENCE: 42<br>MGWSCIILFL VATATGVHSD | 20 |

What is claimed is:

1. A fusion protein comprising:
   i) five to ten tandemly connected intercellular adhesion molecule-1 (ICAM-1) targeting segments, wherein each ICAM-1 targeting segment comprises SEQ ID NO: 26 (NNQKIVNLKEKVAQLEA);
   ii) an enzyme segment that can be catalytically active at the pH of a lysosome, wherein the enzyme segment comprises Acid sphingomyelin osidosis, Tay-Sachs disease, GM2 gangliosidosis, Sandhoff disease, Fabry disease, Gaucher disease, metachromatic leukodystrophy, Krabbe disease, Niemann-Pick disease type A, Niemann-Pick disease type B, Niemann-Pick disease type C, Niemann-Pick disease type D, Farber disease, Wolman disease, Hurler Syndrome, Scheie Syndrome, Hurler-Scheie Syndrome, Hunter Syndrome, Sanfilippo A Syndrome, Sanfilippo B Syndrome, Sanfilippo C Syndrome, Sanfilippo D Syndrome, Morquio A disease, Morquio B disease, Maroteaux-Lamy disease, Sly Syndrome, α-mannosidosis, β-mannosidosis, fucosidosis, aspartylglucosaminuria, sialidosis, mucolipidosis II, mucolipidosis III, mucolipidosis IV, Goldberg Syndrome, Schindler disease, cystinosis, Salla disease, infantile sialic acid storage disease, Batten disease, infantile neuronal ceroid lipofuscinosis, and prosaposin, Parkinson's Disease, or a combination thereof.

11. An expression vector encoding the fusion protein of claim 1.

12. One or more modified cells that are modified to express the fusion protein of claim 1.

* * * * *